(12) United States Patent
Miyake et al.

(10) Patent No.: US 11,059,977 B2
(45) Date of Patent: Jul. 13, 2021

(54) NEAR-INFRARED-ABSORBING DYE, OPTICAL FILTER, AND IMAGING DEVICE

(71) Applicant: AGC Inc., Chiyoda-ku (JP)

(72) Inventors: Noriaki Miyake, Chiyoda-ku (JP); Satoshi Okada, Chiyoda-ku (JP); Jun Irisawa, Chiyoda-ku (JP); Teppei Konishi, Chiyoda-ku (JP); Keigo Matsuura, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 379 days.

(21) Appl. No.: 16/052,676

(22) Filed: Aug. 2, 2018

(65) Prior Publication Data
US 2018/0346729 A1 Dec. 6, 2018

Related U.S. Application Data

(63) Continuation of application No. PCT/JP2017/003734, filed on Feb. 2, 2017.

(30) Foreign Application Priority Data

Feb. 2, 2016 (JP) .............................. JP2016-018255
Jun. 30, 2016 (JP) .............................. JP2016-130963

(51) Int. Cl.
*G02B 5/22* (2006.01)
*C09B 23/14* (2006.01)
(Continued)

(52) U.S. Cl.
CPC ............ *C09B 23/14* (2013.01); *C07D 209/08* (2013.01); *C07D 217/02* (2013.01);
(Continued)

(58) Field of Classification Search
CPC .......... G02B 5/223; G02B 5/208; G02B 5/22; G02B 5/281
See application file for complete search history.

(56) References Cited

U.S. PATENT DOCUMENTS 6,342,340 B1 6/2002 Tanaka et al.
8,159,596 B2 4/2012 Yamano
(Continued)

FOREIGN PATENT DOCUMENTS

EP 0 994 381 A1 4/2000
JP 1-228960 A 9/1989
(Continued)

OTHER PUBLICATIONS

International Search Report dated Mar. 7, 2017 in PCT/JP2017/003734, 4 pages.
(Continued)

*Primary Examiner* — Joseph P Martinez
(74) *Attorney, Agent, or Firm* — Oblon, McClelland, Maier & Neustadt, L.L.P.

(57) ABSTRACT

Provided is a near-infrared-absorbing dye increasing a visible light transmittance and having a near-infrared blocking characteristic. The near-infrared-absorbing dye has an absorption characteristic measured by dissolving the dye in dichloromethane satisfying the following requirements. •In an absorption spectrum at a wavelength of 400 to 800 nm, there is a maximum absorption wavelength $\lambda_{max}$ in a wavelength region of 670 nm or more. •The following relational expression is established between a maximum absorption constant $\varepsilon_A$ with respect to light with a wavelength of 430 to 550 nm and a maximum absorption constant $\varepsilon_B$ with respect to light with a wavelength of 670 nm or more, where $\varepsilon_B/\varepsilon_A \geq 65$. •In a spectral transmittance curve, an average transmittance of light with a wavelength of 430 to 460 nm is 94.0% or more when a transmittance at the maximum absorption wavelength $\lambda_{max}$ is set to 1%.

28 Claims, 14 Drawing Sheets

(51) Int. Cl.

| | | |
|---|---|---|
| *C07D 217/02* | (2006.01) | |
| *C07D 487/04* | (2006.01) | |
| *C07D 333/66* | (2006.01) | |
| *C07D 235/08* | (2006.01) | |
| *C08L 101/00* | (2006.01) | |
| *C07D 519/00* | (2006.01) | |
| *C07D 235/30* | (2006.01) | |
| *C07D 237/28* | (2006.01) | |
| *C07D 209/08* | (2006.01) | |
| *C09D 179/08* | (2006.01) | |
| *C08K 5/3417* | (2006.01) | |
| *C08K 5/3437* | (2006.01) | |
| *C08K 5/3447* | (2006.01) | |
| *C08K 5/3475* | (2006.01) | |
| *C09B 57/00* | (2006.01) | |
| *G02B 5/20* | (2006.01) | |
| *H01L 27/146* | (2006.01) | |

(52) U.S. Cl.
CPC ......... *C07D 235/08* (2013.01); *C07D 235/30* (2013.01); *C07D 237/28* (2013.01); *C07D 333/66* (2013.01); *C07D 487/04* (2013.01); *C07D 519/00* (2013.01); *C08K 5/3417* (2013.01); *C08K 5/3437* (2013.01); *C08K 5/3447* (2013.01); *C08K 5/3475* (2013.01); *C08L 101/00* (2013.01); *C09B 57/007* (2013.01); *C09D 179/08* (2013.01); *G02B 5/208* (2013.01); *G02B 5/223* (2013.01); *H01L 27/1462* (2013.01); *H01L 27/14627* (2013.01)

(56) References Cited

U.S. PATENT DOCUMENTS

| | | |
|---|---|---|
| 2002/0110767 A1 | 8/2002 | Tanaka et al. |
| 2011/0315939 A1 | 12/2011 | Okayasu et al. |
| 2012/0197026 A1 | 8/2012 | Maeda et al. |
| 2012/0328975 A1 | 12/2012 | Tian et al. |
| 2014/0055652 A1 | 2/2014 | Hasegawa et al. |
| 2014/0061505 A1* | 3/2014 | Steppel .............. G01N 21/6428 250/459.1 |
| 2014/0063597 A1 | 3/2014 | Shimmo et al. |
| 2014/0091419 A1 | 4/2014 | Hasegawa et al. |
| 2014/0264202 A1 | 9/2014 | Nagaya et al. |
| 2014/0350146 A1 | 11/2014 | Tsubouchi |
| 2015/0146057 A1 | 5/2015 | Konishi et al. |
| 2015/0260889 A1 | 9/2015 | Shiono et al. |
| 2015/0277002 A1 | 10/2015 | Ezoe et al. |
| 2015/0285971 A1 | 10/2015 | Nagaya et al. |
| 2016/0195651 A1 | 7/2016 | Yoshioka et al. |
| 2016/0252664 A1 | 9/2016 | Kim et al. |
| 2016/0259103 A1 | 9/2016 | Kim et al. |
| 2016/0291223 A1 | 10/2016 | Rudigier-Voigt et al. |
| 2018/0067243 A1* | 3/2018 | Shiono .................. G02B 5/208 |

FOREIGN PATENT DOCUMENTS

| | | |
|---|---|---|
| JP | 2-7069 | 1/1990 |
| JP | 2-12259 | 1/1990 |
| JP | 2-13964 A | 1/1990 |
| JP | 2-23360 | 1/1990 |
| JP | 2000-160042 | 6/2000 |
| JP | 2000-265077 | 9/2000 |
| JP | 2001-117201 | 4/2001 |
| JP | 2006-106570 | 4/2006 |
| JP | 2006-301489 | 11/2006 |
| JP | 2008-51985 | 3/2008 |
| JP | 2008-181028 | 8/2008 |
| JP | 2010-184975 | 8/2010 |
| JP | 2010-184980 | 8/2010 |
| JP | 2011-100084 | 5/2011 |
| JP | 2012-008532 | 1/2012 |
| JP | 2012-103340 | 5/2012 |
| JP | 2012-137645 | 7/2012 |
| JP | 2012-137646 | 7/2012 |
| JP | 2012-137647 | 7/2012 |
| JP | 2012-137648 | 7/2012 |
| JP | 2012-137649 | 7/2012 |
| JP | 2012-137650 | 7/2012 |
| JP | 2012-137651 | 7/2012 |
| JP | 2012-185468 | 9/2012 |
| JP | 2013-006930 | 1/2013 |
| JP | 2013-29708 | 2/2013 |
| JP | 2013-50593 | 3/2013 |
| JP | 2013-190553 | 9/2013 |
| JP | 2014-52604 | 3/2014 |
| JP | 2014-59550 | 4/2014 |
| JP | 2014-126642 | 7/2014 |
| JP | 2014-148567 | 8/2014 |
| JP | 5596667 B2 | 9/2014 |
| JP | 2015-176046 | 10/2015 |
| JP | 2016-90781 | 5/2016 |
| JP | 6020746 B2 | 11/2016 |
| WO | WO 2010/095676 A1 | 8/2010 |
| WO | WO 2011/086785 A1 | 7/2011 |
| WO | WO 2013/054864 A1 | 4/2013 |
| WO | WO 2013/161492 A1 | 10/2013 |
| WO | WO 2014/030628 A1 | 2/2014 |
| WO | WO 2014/088063 A1 | 6/2014 |
| WO | WO 2014/163405 A1 | 10/2014 |
| WO | WO 2014/168189 A1 | 10/2014 |
| WO | WO 2014/192714 A1 | 12/2014 |
| WO | WO 2014/192715 A1 | 12/2014 |
| WO | WO 2015/022892 A1 | 2/2015 |
| WO | WO 2015/099060 A1 | 7/2015 |
| WO | WO 2015/122595 A1 | 8/2015 |
| WO | WO 2016/043166 A1 | 3/2016 |
| WO | WO 2016/114362 A1 | 7/2016 |
| WO | WO 2016/114363 A1 | 7/2016 |
| WO | WO 2016/133099 A1 | 8/2016 |
| WO | WO 2016/158461 A1 | 10/2016 |
| WO | WO 2016/158818 A1 | 10/2016 |
| WO | WO 2016/158819 A1 | 10/2016 |
| WO | WO 2016/171219 A1 | 10/2016 |

OTHER PUBLICATIONS

Bello, Kasali A. et al, "Near-infrared-absorbing squaraine dyes containing 2,3-dihydroperimidine terminal groups", Journal of the Chemical Society, Chemical Communications. Issue 5, 1993, pp. 452-454.

Law, Kock Yee, "Squaraine chemistry: effects of structural changes on the absorption and multiple fluorescence emission of bis[4-(dimethylamino)phenyl]squaraine and its derivatives", The Journal of Physical Chemistry, vol. 91. 1987, pp. 5187-5193.

* cited by examiner

NEAR-INFRARED-ABSORBING DYE, OPTICAL FILTER, AND IMAGING DEVICE

CROSS-REFERENCE TO RELATED APPLICATIONS

This application is a continuation of prior International Application No. PCT/JP2017/003734, filed on Feb. 2, 2017 which is based upon and claims the benefit of priority from Japanese Patent Applications Nos. 2016-018255 filed on Feb. 2, 2016, and 2016-130963 filed on Jun. 30, 2016; the entire contents of all of which are incorporated herein by reference.

FIELD

The present disclosure relates to a near-infrared-absorbing dye which transmits visible light and cuts off near-infrared light, an optical filter, and an imaging device provided with the optical filter.

BACKGROUND

In an imaging device using a solid-state image sensor such as a CCD or a CMOS image sensor, which is mounted on a digital still camera and the like, an optical filter (near-infrared cut filter) which transmits visible light and blocks near-infrared light has been used for the purpose of well reproducing a color tone and obtaining a clear image.

In the optical filter, particularly a dye having high absorbency in a near-infrared region and having a high transmitting property in a visible region is used, thereby making it possible to obtain a steep cutoff property with respect to the near-infrared light and obtain good color reproducibility of an image by visible light.

Meanwhile, even though both properties of the high cutoff property of near-infrared light and the high transmitting property of visible light are tried to be obtained, it is difficult to obtain a 100% transmittance with respect to the light in the entire visible region, and a region relatively low in transmittance exists even in the visible region. For example, an already-known squarylium-based dye is excellent in cutoff property of near-infrared light, has a high level of visible light transmittance, and has a characteristic in which the transmittance from the visible region toward the near-infrared region changes steeply. The present applicant has found out that an optical filter containing the squarylium-based dye enables achievement of a visible light transmittance of a certain level or more. However, a demand for higher precision color reproducibility has increased by further increasing the visible light transmittance. Particularly, there is a growing demand for increasing the precision of blue color reproducibility by more increasing the transmittance of light with a wavelength of 430 to 550 nm on a relatively short wavelength side even in the visible region.

Thus, for the purpose of increasing the visible light transmittance, various squarylium dyes having a new structure also have been proposed, but have not reached a satisfactory level yet.

Further, there has been proposed an optical filter using a squarylium-based dye and a phthalocyanine-based dye in combination, but as the transmitting property of visible light, the technology of increasing the transmittance with respect to the light with the wavelength of 430 to 550 nm, in particular, has not been disclosed therein. Further, Patent Document 4 uses a plurality of different dyes, and therefore visible light absorption increases collaterally, resulting in that there is also a problem of failing to obtain a high visible light transmittance.

SUMMARY

The present disclosure has an object to provide a near-infrared-absorbing dye which is capable of achieving an excellent light blocking property with respect to near-infrared light and have a high visible-light-transmitting property, which has an increased transmittance of light with a wavelength of 430 to 550 nm, in particular, an optical filter, and an imaging device excellent in color reproducibility using the optical filter.

A near-infrared-absorbing dye according to the present disclosure is characterized in that an absorption characteristic measured by dissolving the dye in dichloromethane satisfies requirements (i-1) to (i-3).

(i-1) In an absorption spectrum at a wavelength of 400 to 800 nm, there is a maximum absorption wavelength $\lambda_{max}$ in a wavelength region of 670 nm or more.

(i-2) The following relational expression is established between a maximum absorption constant $\varepsilon_A$ with respect to light with a wavelength of 430 to 550 nm and a maximum absorption constant $\varepsilon_B$ with respect to light with a wavelength of 670 nm or more.

$$\varepsilon_B/\varepsilon_A \geq 65$$

(i-3) In a spectral transmittance curve, an average transmittance of light with a wavelength of 430 to 460 nm is 94.0% or more when a transmittance at the maximum absorption wavelength $\lambda_{max}$ is set to 1%.

The near-infrared-absorbing dye of the present disclosure is characterized in that it is formed of a squarylium-based compound represented by Formula (AI).

[Chemical Formula 1]

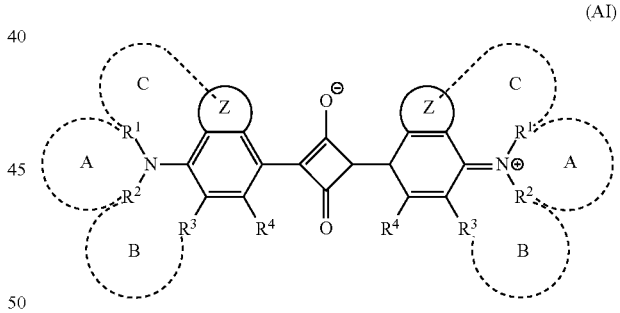

(AI)

In Formula (AI), each of rings Z is independently a five-membered ring or a six-membered ring which may contain 0 to 3 pieces of heteroatoms in the ring and which may have a substituent, $R^1$ and $R^2$, $R^2$ and $R^3$, and $R^1$ and a carbon atom or the heteroatom forming the ring Z may couple with each other and respectively form a hetero ring A, a hetero ring B, and a hetero ring C together with a nitrogen atom, when the hetero ring is not formed, $R^1$ and $R^2$ each independently represent a hydrogen atom, or a hydrocarbon group which may contain an unsaturated bond, a heteroatom, a saturated or unsaturated ring structure between carbon atoms and which may have a substituent, $R^3$ each independently represent an alkyl group or an alkoxy group which may contain a hydrogen atom, a halogen atom, a hydroxyl group, or a heteroatom between carbon atoms, R⁴ each independently represent an alkyl group or an alkoxy group which may contain a hydrogen atom, a halogen atom, a hydroxyl group, or a heteroatom between carbon atoms.

The near-infrared-absorbing dye of the present disclosure is characterized in that it is formed of a squarylium-based compound represented by Formula (AII).

[Chemical Formula 2]

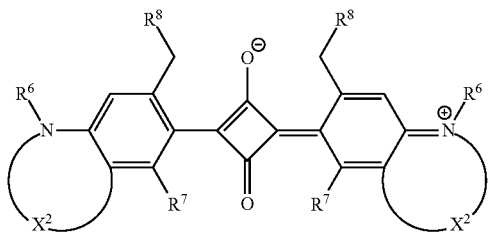

(AII)

In Formula (AII), $R^6$ each independently represent a hydrogen atom, or a hydrocarbon group which may contain an unsaturated bond, a heteroatom, a saturated or unsaturated ring structure between carbon atoms and which may have a substituent, $R^7$ each independently represent a hydrogen atom, a halogen atom, a hydroxyl group, or an alkyl group or an alkoxy group which may contain a heteroatom between carbon atoms, $R^8$ each independently represent a halogen atom, a hydroxyl group, an alkoxy group with a carbon number of 1 to 12, an acyl group or an acyloxy group with a carbon number of 1 to 12, a perfluoroalkyl group with a carbon number of 1 to 12, or a —$SO_2R^9$ group (where $R^9$ represents an alkyl group with a carbon number of 1 to 12 which may have a substituent), and $X^2$ each represent a bivalent hydrocarbon group which may contain an unsaturated bond, a heteroatom, a saturated or unsaturated ring structure between carbon atoms and which may have a substituent.

An optical filter of the present disclosure is characterized in that it includes an absorption layer which contains the near-infrared-absorbing dye and a resin.

Further, an imaging device of the present disclosure is characterized in that it includes a solid-state image sensor, an imaging lens, and the aforementioned optical filter.

According to the present disclosure, it is possible to obtain an optical filter that is excellent in cutoff property with respect to near-infrared light and has a high transmittance in a visible region, particularly, of light with a wavelength of 430 to 550 nm. Further, an imaging device excellent in color reproducibility can be obtained by mounting the optical filter thereon.

DETAILED DESCRIPTION

Hereinafter, embodiments will be explained. In the following description, an optical filter is sometimes abbreviated as an "NIR filter", a near-infrared-absorbing dye is sometimes abbreviated as an "NIR dye", and an ultraviolet absorbing dye is sometimes abbreviated as a "UV dye".

<NIR Filter>

A NIR filter of one embodiment (hereinafter referred to as a "present filter") includes one layer or two or more layers of an absorption layer. When the absorption layer has two or more layers, each layer may be the same or different. When the absorption layer has a constitution having two or more layers, there can be cited an example where one layer may be a near-infrared absorption layer formed of a resin containing a NIR dye, and the other layer may be an ultraviolet absorption layer formed of a resin containing an UV dye. The absorption layer itself may be a substrate (resin substrate).

The present filter may include one layer or two or more layers of selected wavelength blocking layers that block light in a specific wavelength region. When the selected wavelength blocking layer is formed of two or more selected layers, each layer may be the same or different. When the selected wavelength blocking layer has a constitution having two or more selected layers, there can be cited an example where one layer may be a near-infrared blocking layer that blocks at least near-infrared light and the other layer may be an ultraviolet blocking layer that blocks at least ultraviolet light.

The present filter may further include a transparent substrate. In this case, the absorption layer and the selected wavelength blocking layer may be provided on the same principal surface of the transparent substrate, or may be provided on different principal surfaces. When the absorption layer and the selected wavelength blocking layer are provided on the same principal surface, a stacking order of these layers is not particularly limited. The present filter may further include other functional layers such as an anti-reflection layer.

Figure 1A:
FIGS. 1A to 1F each are a cross-sectional view schematically illustrating an example of an optical filter.
Figure 1B:
Figure 1C:
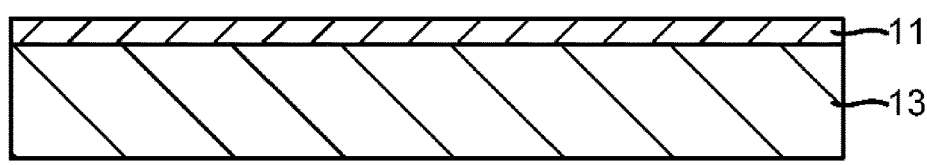

The following explains a constitutional example of the present filter. FIG. 1A illustrates an example including an absorption layer 11, FIG. 1B illustrates an example including the absorption layer 11 and a selected wavelength blocking layer 12, and FIG. 1C is an example including a transparent substrate 13 and the absorption layer 11. The absorption layer 11 may be formed as an absorption substrate.

In FIGS. 1A to 1C, the absorption layer 11 may include two layers of a near-infrared absorption layer and an ultraviolet absorption layer. For example, in FIG. 1B, the filter may have the constitution including the near-infrared absorption layer and the ultraviolet absorption layer in this order on the selected wavelength blocking layer 12, or the constitution including these two layers stacked in reverse order. Similarly, in FIG. 1C, the filter may have the constitution including the near-infrared absorption layer and the ultraviolet absorption layer in this order on the transparent substrate 13, or the constitution including these two layers stacked in reverse order.

Figure 1D:
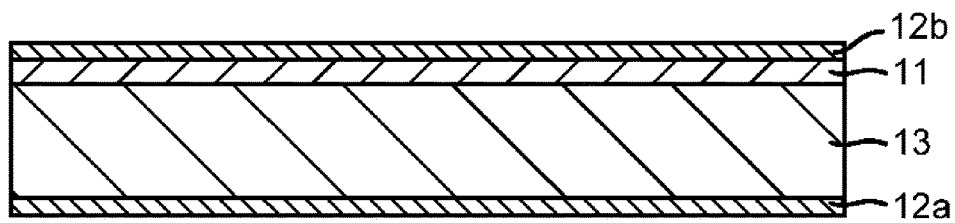

FIG. 1D illustrates an example including the absorption layer 11 on one principal surface of the transparent substrate 13, and selected wavelength blocking layers 12a and 12b on the other principal surface of the transparent substrate 13 and a principal surface of the absorption layer 11, respectively.

Figure 1E:
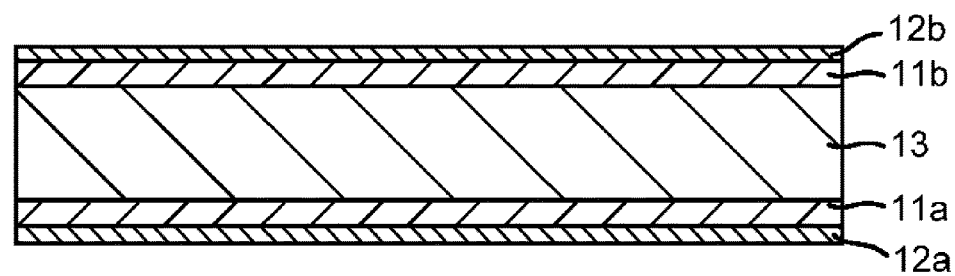

FIG. 1E illustrates an example including an absorption layer 11a on one principal surface and an absorption layer 11b on the other principal surface of the transparent substrate 13, and further including the selected wavelength blocking layer 12a on a principal surface of the absorption layer 11a and the selected wavelength blocking layer 12b on a principal surface of the absorption layer 11b.

The selected wavelength blocking layers 12a and 12b have properties reflecting ultraviolet light and near-infrared light and transmitting visible light. For example, the selected wavelength blocking layer 12a may reflect ultraviolet light and first near-infrared light and the selected wavelength blocking layer 12b may reflect ultraviolet light and second near-infrared light.

Figure 1F:
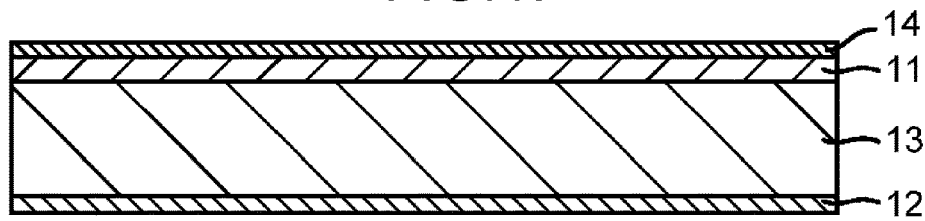
Figure 2A:
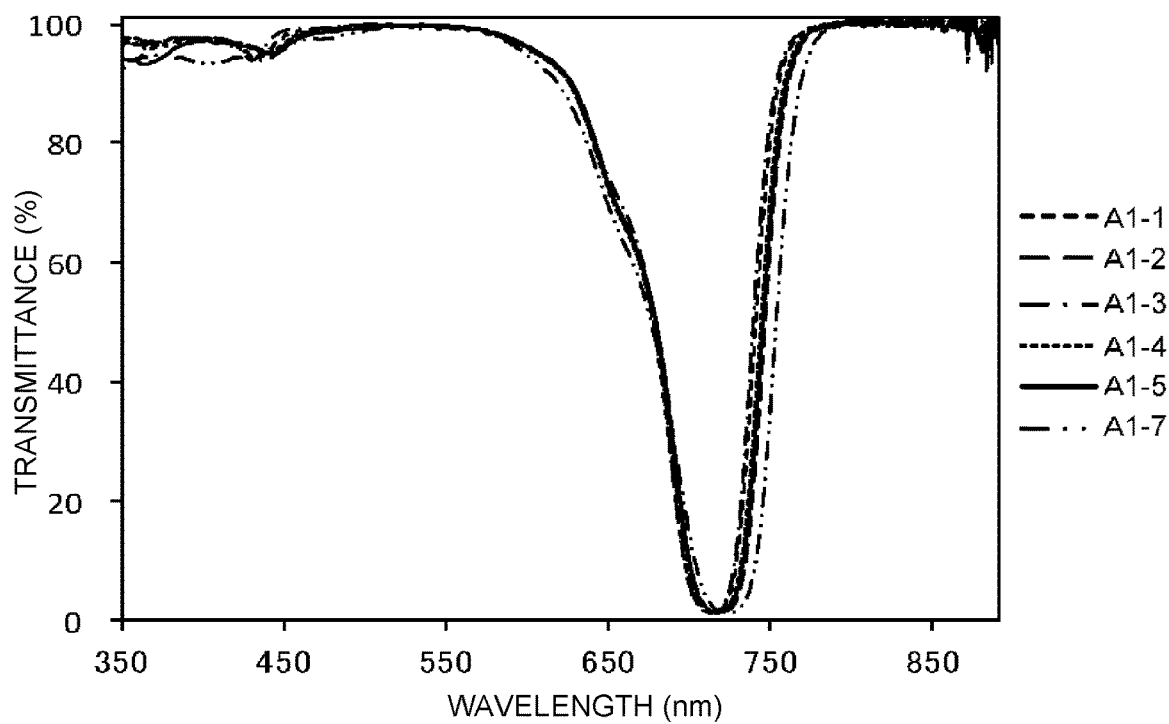
FIG. 2A is a view illustrating spectral transmittance curves of NIR dyes used in examples.
Figure 2B:
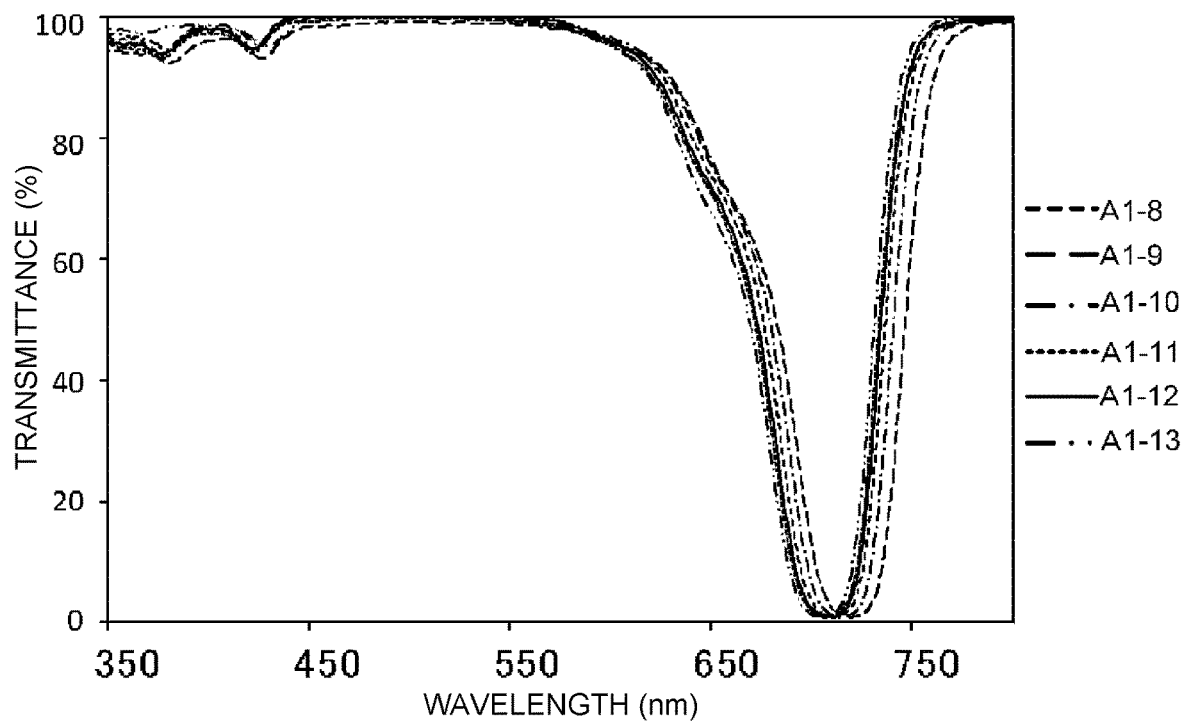
FIG. 2B is a view illustrating spectral transmittance curves of NIR dyes used in examples.
Figure 2C:
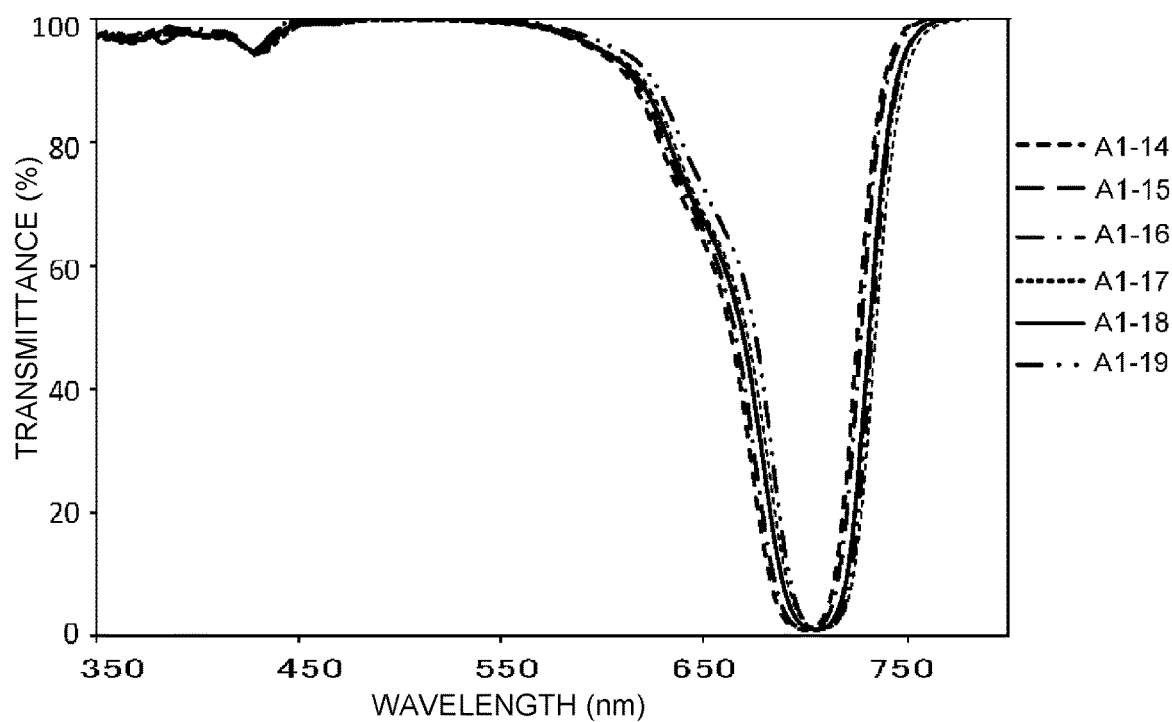
FIG. 2C is a view illustrating spectral transmittance curves of NIR dyes used in examples.
Figure 2D:
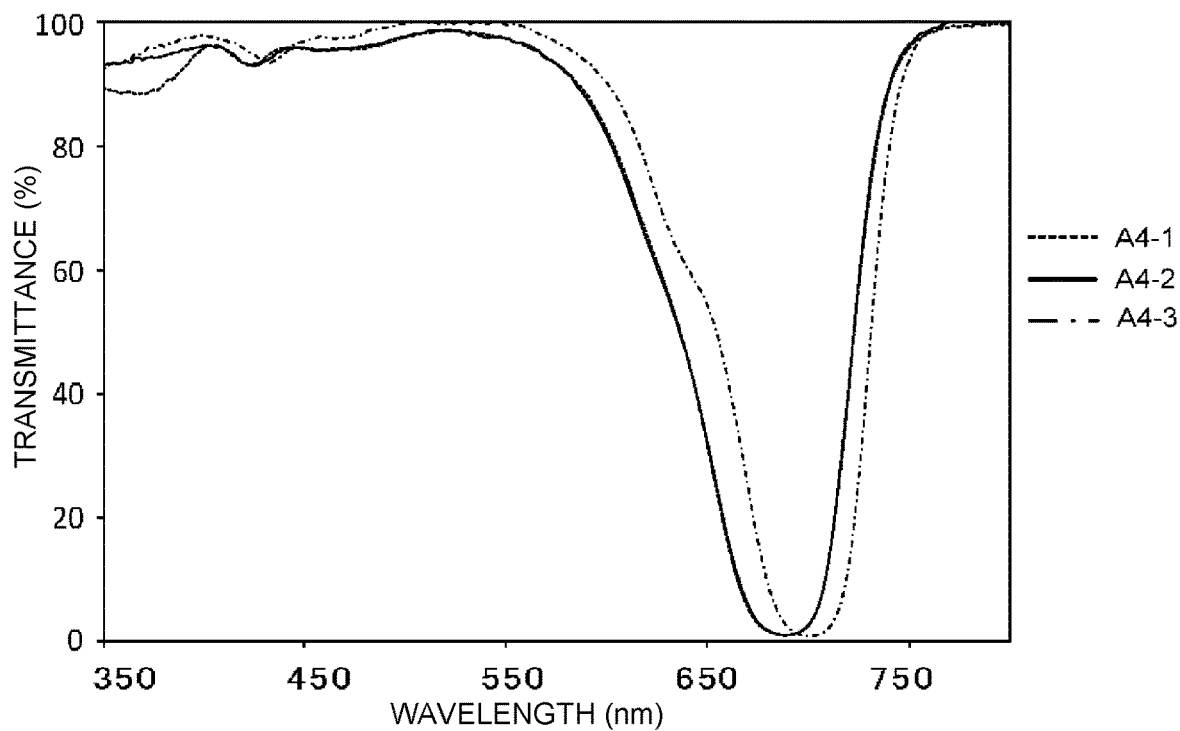
FIG. 2D is a view illustrating spectral transmittance curves of NIR dyes used in examples.

FIG. 1F illustrates an example including an anti-reflection layer 14 at a position of the selected wavelength blocking layer 12b on the principal surface of the absorption layer 11 of the filter illustrated in FIG. 1D. In the case where the constitution in which the absorption layer is an uppermost surface is taken, the anti-reflection layer may be provided on the absorption layer, and the anti-reflection layer may have a constitution covering an entire side surface of the absorption layer (not-illustrated) because the anti-reflection layer increases a moisture-proof effect of the absorption layer. Hereinafter, the selected wavelength blocking layer will be explained as a "reflection layer" having a reflection function unless otherwise noted.

The present filter only needs to satisfy (iii-1), preferably satisfies (iii-1) and (iii-2), more preferably satisfies at least one of (iii-3) to (iii-6) in addition to (iii-1) and (iii-2), and further preferably satisfies all of (iii-1) to (iii-6). (iii-1) to (iii-5) are requirements in a spectral transmittance curve at an incident angle of 0°.

(iii-1) An average transmittance of light with a wavelength of 430 to 550 nm is 90% or more and a minimum transmittance of light with a wavelength of 430 to 550 nm is 75% or more.

(iii-2) An average transmittance of light with a wavelength of 430 to 480 nm is 87% or more.

(iii-3) An average transmittance of light with a wavelength of 600 to 700 nm is 25% or more.

(iii-4) An average transmittance of light with a wavelength of 350 to 395 nm is 2% or less.

(iii-5) An average transmittance of light with a wavelength of 710 to 1100 nm is 2% or less.

(iii-6) An average value of an absolute value of a difference between a transmittance of light with a wavelength of 600 to 700 nm in a spectral transmittance curve at an incident angle of 0° and a transmittance of light with a wavelength of 600 nm to 700 nm in a spectral transmittance curve at an incident angle of 30° (hereinafter referred to as an "average shift amount of transmittance of light with a wavelength of 600 to 700 nm") is 7° O/4 or less.

Satisfying (iii-1) makes it possible to further increase precision of color reproducibility of a blue captured image.

Satisfying (iii-2) makes it possible to further increase precision of color reproducibility of a blue captured image.

Satisfying (iii-3) makes it possible to efficiently transmit light with a wavelength of 600 to 700 nm, which affects visibility of a human being, while cutting light with a wavelength of 700 nm or more, which is unnecessary for spectral sensitivity of a solid-state image sensor.

Satisfying (iii-4) makes it possible to make spectral sensitivity of a solid-state image sensor approximate to visibility of a human being.

Satisfying (iii-5) makes it possible to make spectral sensitivity of a solid-state image sensor approximate to visibility of a human being.

Satisfying (iii-6) makes it possible to decrease incident angle dependence of light with a wavelength of 600 to 700 nm and to decrease incident angle dependence of spectral sensitivity of a solid-state image sensor in this wavelength region.

In the present filter, the average transmittance of light with the wavelength of 430 to 550 nm is preferably 91% or more and more preferably 92% or more in (iii-1). Further, the minimum transmittance of light with the wavelength of 430 to 550 nm is preferably 77% or more, and more preferably 80% or more in (iii-1). In the present filter, the average transmittance of light with the wavelength of 430 to 480 nm is preferably 88% or more, more preferably 89% or more, and further preferably 90% or more in (iii-2). Further, in the present filter, the average transmittance of light with the wavelength of 600 to 700 nm is preferably 30% or more in (iii-3).

In the present filter, the average transmittance of light with the wavelength of 350 to 395 nm is preferably 1.5% or less, more preferably 1% or less, and further preferably 0.5% or less in (iii-4). In the present filter, the average transmittance of light with the wavelength of 710 to 1100 nm is preferably 1% or less, more preferably 0.5% or less, and further preferably 0.3% or less in (iii-5). Further, in the present filter, the average shift amount of the transmittance of light with the wavelength of 600 to 700 nm is preferably 3%/nm or less, and more preferably 2%/nm or less in (iii-6).

Next, the absorption layer, the reflection layer, the transparent substrate, and the anti-reflection layer of the present filter will be explained.

[Absorption Layer]

The absorption layer contains a near-infrared-absorbing dye (A) and a transparent resin (B), and typically is a layer or a (resin) substrate where the near-infrared-absorbing dye (A) is evenly dissolved or dispersed in the transparent resin (B). The absorption layer may further contain an ultraviolet absorbing dye (U). A plurality of absorption layers may be provided as described previously. Hereinafter, the near-infrared-absorbing dye (A) is also called a "dye (A)", and the ultraviolet absorbing dye (U) is also called a "dye (U)".

In the present filter, a thickness of the absorption layer is preferably 0.1 to 100 µm. When the absorption layer is made up of a plurality of layers, a total thickness of the layers is preferably 0.1 to 100 µm. When the thickness is less than 0.1 µm, there is a possibility that a desired optical characteristic cannot be exhibited sufficiently, and when the thickness is over 100 µm, a flatness of the layer decreases and there is a possibility that in-plane dispersion of absorptance occurs. The thickness of the absorption layer is more preferably 0.3 to 50 µm. When other functional layers such as a reflection layer and an anti-reflection layer are provided, there is a possibility that the absorption layer is too thick, thus causing cracks or the like depending on materials of the functional layers. Accordingly, the thickness of the absorption layer is more preferably 0.3 to 10 µm.

(Near-Infrared-Absorbing Dye (A))

In the dye (A), an absorption characteristic measured by dissolving the dye in dichloromethane preferably satisfies (i-1) to (i-3).

(i-1) In an absorption spectrum of light with a wavelength of 400 to 800 nm, there is a maximum absorption wavelength $\lambda_{max}$ in a wavelength region of 670 nm or more.

(i-2) The following relational expression is established between a maximum absorption constant $\varepsilon_A$ with respect to light with a wavelength of 430 to 550 nm and a maximum absorption constant $\varepsilon_B$ with respect to light with a wavelength of 670 nm or more.

$$\varepsilon_B/\varepsilon_A \geq 65$$

(i-3) In a spectral transmittance curve, an average transmittance with respect to light with a wavelength of 430 to 460 nm ($T_{Avg.(430-460)}$) is 94.0% or more when a transmittance at the maximum absorption wavelength $\lambda_{max}$ is set to 1%.

In the dye (A), the absorption characteristic measured by dissolving the dye in dichloromethane preferably satisfies at least one, more preferably satisfies at least two, further preferably satisfies at least three, and particularly preferably satisfies all of (i-4) to (i-7) in addition to (i-1) to (i-3).

(i-4) In the spectral transmittance curve, when wavelengths with which transmittances become 80%, 10% on a shorter wavelength side than the maximum absorption wavelength $\lambda_{max}$, are respectively set to a wavelength $\lambda_{80}$ and a wavelength $\lambda_{10}$ when the transmittance at the maximum absorption wavelength $\lambda_{max}$ is set to 1%, a maximum value of a slope ($\Delta T/\Delta \lambda$) of the spectral transmittance curve between the wavelength $\lambda_{80}$ and the wavelength $\lambda_{10}$ is −0.5 [%/nm] or less.

(i-5) In a spectral transmittance curve, a transmittance of light with a wavelength of 410 to 460 nm ($T_{(410-460)}$) is 93.0% or more, when a transmittance at the maximum absorption wavelength $\lambda_{max}$ is set to 1%.

(i-6) In a spectral transmittance curve, a longest wavelength ($\lambda_{97}$) where a transmittance with respect to light with a wavelength of 460 nm or less is 97% is 457 nm or less, when a transmittance at the maximum absorption wavelength $\lambda_{max}$ is set to 1%.

(i-7) In a spectral transmittance curve, a difference ($\lambda_{max}-\lambda_{80}$) between the wavelength $\lambda_{80}$ with which the transmittance becomes 80% on the shorter wavelength side than the maximum absorption wavelength $\lambda_{max}$ and the maximum absorption wavelength $\lambda_{max}$ is 78 nm or less, when a transmittance at the maximum absorption wavelength max is set to 1%.

In (i-1), $\lambda_{max}$ is preferably held in 680 to 770 nm, more preferably held in 680 to 750 nm, and further preferably held in 690 to 730 nm.

In (i-2), $\varepsilon_B/\varepsilon_A \geq 70$ is more preferred. In (i-2), it is preferred that $\varepsilon_B/\varepsilon_A \geq 65$ is established, and more preferred that $\varepsilon_B/\varepsilon_A \geq 70$ is established between the maximum absorption constant $\varepsilon_A$ with respect to light with the wavelength of 430 to 550 nm and the maximum absorption constant $\varepsilon_B$ which is set to be a maximum absorption constant with respect to light with a wavelength of 680 to 770 nm.

In (i-3), $T_{Avg.(430-460)}$ is preferably 95.0% or more, more preferably 96.0% or more, and further preferably 96.5% or more.

In (i-4), a maximum value of ($\Delta T/\Delta \lambda$) is preferably −0.52 [%/nm] or less, and more preferably −0.55 [%/nm] or less. The slope ($\Delta T/\Delta \lambda$) can be given by values or the like obtained, for example, at every 1 nm interval (that is, $\Delta \lambda=1$ nm).

In (i-5), ($T_{(410-460)}$) is preferably 93.5% or more, and more preferably 94.0% or more.

In (i-6), $\lambda_{97}$ is preferably 455 nm or less, more preferably 452 nm or less, and further preferably 445 nm or less.

In (i-7), $\lambda_{max}-\lambda_{80}$ is preferably 75 nm or less, and more preferably 73 nm or less.

By using the dye (A) satisfying (i-1) to (i-3), it is possible to obtain an optical filter having an increased visible light transmittance than a conventional one, an increased transmittance of light with a wavelength of 430 to 550 nm while having a good near-infrared blocking characteristic, and further to obtain the optical filter having an increased transmittance of light with a wavelength of 430 to 460 nm.

Concretely, satisfying (i-1) makes it possible to sufficiently block predetermined near-infrared light. Satisfying (i-2) and (i-3) makes it possible to increase particularly a blue visible light transmittance. Satisfying (i-4) makes it possible to obtain a steep change of transmittance between a long wavelength side region in a visible region and a near-infrared region, to increase a red visible light transmittance, and to enable a good near-infrared light blocking characteristic. Satisfying (i-5) makes it possible to increase particularly the blue visible light transmittance. Satisfying (i-6) makes it possible to further increase the blue visible light transmittance. Further, satisfying (i-7) makes it possible to obtain the steep change of transmittance between the long wavelength side region in the visible region and the near-infrared region, and to enable the good near-infrared light blocking characteristic.

The dye (A) is not particularly limited as long as the dye satisfies the aforementioned conditions. Examples of the dye (A) include, for example, a squarylium compound, for example, a squarylium-based compound represented by Formula (AI) or Formula (AII) (they are illustrated later). In this specification, a NIR dye formed of the compound represented by Formula (AI) is also referred to as a NIR dye (AI), a NIR dye formed of the compound represented by Formula (AII) is also referred to as a NIR dye (AII), and the same applies to other dyes (for example, a NIR dye formed of a compound represented by later-described Formula (AI-1) is also referred to as a NIR dye (AI-1)). Further, for example, a group represented by Formula (in) is described as a group (in) and groups represented by other formulas are also described in the same manner.

<NIR Dye (AI)>

The NIR dye (AI) is formed of the squarylium-based compound having one condensed ring structure on each of the left and right sides, in which a squarylium skeleton is held in a center of a molecular structure and one benzene ring is bonded to the squarylium skeleton on each of the left and right sides, where each benzene ring is bonded to a nitrogen atom at a fourth position, and a hetero ring containing the second-position and third-position carbon atoms of the benzene ring is formed.

[Chemical Formula 3]

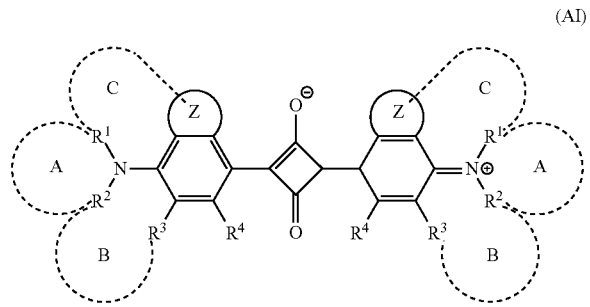

(AI)

In Formula (AI), each ring Z is a five-membered ring or a six-membered ring having 0 to 3 pieces of heteroatoms in the ring. The heteroatom may be any of a nitrogen atom, a sulfur atom, and an oxygen atom, but it is preferably the nitrogen atom and the sulfur atom in the context of increasing the visible light transmittance. Concrete examples of the ring Z include a pyrrolidine ring, a piperidine ring, a piperazine ring, a pyrrole ring, a thiophene ring, an imidazole ring, a pyrazole ring, a thiazole ring, an isothiazole ring, an oxazole ring, an isoxazole ring, a pyridine ring, a pyrimidine ring, a pyridazine ring, a pyrazine ring, a triazine ring, a triazole ring, and so on. Among them, an aromatic hetero ring is preferred, and in particular, the pyridine ring, the pyrimidine ring, the pyridazine ring, the pyrrole ring, the thiophene ring, the imidazole ring, the pyrazole ring, the thiazole ring, the isothiazole ring, and the triazole ring are preferred because it is possible to delocalize electrons of the heteroatom, to obtain an effect of stabilizing an energy level of a ground state of an unshared electron pair, and to improve the visible light transmittance.

In the ring Z, one or more hydrogen atoms bonded to the carbon atom or the nitrogen atom forming the ring Z may be substituted with a substituent such as a halogen atom, a hydroxyl group, a carboxy group, a sulfo group, a cyano group, an amino group, an N-substituted amino group, a nitro group, an alkoxycarbonyl group, a carbamoyl group, an N-substituted carbamoyl group, an imide group, an alkyl group or an alkoxy group with a carbon number of 1 to 12 which may be substituted with a halogen atom, or the like. Examples of the halogen atom include a fluorine atom, a chlorine atom, a bromine atom, an iodine atom, and so on, and similar atoms can be exemplified as the halogen atom cited in the following explanation. The alkyl group, and the alkyl group which forms the alkoxy group may be any of linear chain, branched chain, and cyclic, and may include an unsaturated bond. As the substituent, a long-chain alkyl group with a carbon number of 4 to 12 is preferred in the context of solubility to a transparent resin, and groups with high electron-withdrawing property such as the halogen atom, the sulfo group, the cyano group, a nitro group, a trifluoromethyl group, and a carbamoyl group are preferred in the context of increasing the visible light transmittance.

In Formula (AI), $R^1$ and $R^2$, $R^2$ and $R^3$, and $R^1$ and a carbon atom or the heteroatom (nitrogen atom) forming the ring Z may couple with each other and respectively form a hetero ring A, a hetero ring B, and a hetero ring C together with the nitrogen atom bonded to the fourth position of the benzene ring. In Formula (AI), all of the hetero ring A to the hetero ring C may be formed, or one or two hetero rings may be formed. In Formula (AI) having one or more hetero rings, the hetero ring A and the hetero ring B are the hetero rings whose ring numbers are each three to six, and the hetero ring C is the hetero ring whose ring number is five or six. Note that "the hetero ring A to the hetero ring C" are hereinafter also referred to as "the ring A to the ring C".

Examples of the ring A and the ring B include an aziridine ring, an azetidine ring, a pyrrolidine ring, a piperidine ring, a piperazine ring, a morpholine ring, and so on. Examples of the ring C include a pyrrolidine ring, a piperidine ring, a piperazine ring, a morpholine ring, and so on.

In each of the rings A, B, and C, one or more hydrogen atoms bonded to a carbon atom or a nitrogen atom forming each ring may be substituted with substituents such as a halogen atom, a hydroxyl group, a carboxy group, a sulfo group, a cyano group, an amino group, an N-substituted amino group, a nitro group, an alkoxycarbonyl group, a carbamoyl group, an N-substituted carbamoyl group, an imide group, and an alkyl group or an alkoxy group with a carbon number of 1 to 12. The alkyl group, and the alkyl group which forms the alkoxy group may be any of linear chain, branched chain, and cyclic.

$R^1$ and $R^2$ when the hetero ring is not formed each independently represent a hydrogen atom, or a hydrocarbon group which may contain an unsaturated bond, a heteroatom (oxygen atom, or the like), a saturated or unsaturated ring structure between carbon atoms and which may have a substituent, and preferably the hydrocarbon group with a carbon number of 1 to 20. Examples of a substituent include a halogen atom, a hydroxyl group, a carboxy group, a sulfo group, a cyano group, an amino group, an N-substituted amino group, a nitro group, an alkoxycarbonyl group, a carbamoyl group, an N-substituted carbamoyl group, an imide group, an alkyl group or an alkoxy group with a carbon number of 1 to 12, and so on. The alkyl group, and the alkyl group which forms the alkoxy group may be any of linear chain, branched chain, and cyclic. As each of $R^1$ and $R^2$ when the hetero ring is not formed, the alkyl group with a carbon number of 1 to 20 is preferred, the alkyl group with the carbon number of 1 to 12 is more preferred, and the alkyl group with the carbon number of 2 to 8 is further preferred, which may be branched and may contain a heteroatom between carbon atoms in the context of the visible light transmittance, solubility to a transparent resin, and the like.

$R^3$ and $R^4$ when the hetero ring is not formed each independently represent a hydrogen atom, a halogen atom, a hydroxyl group or an alkyl group or an alkoxy group, and preferably the alkyl group or the alkoxy group with a carbon number of 1 to 20. The alkyl group, and the alkyl group which forms the alkoxy group may be any of linear chain, branched chain, and cyclic. As $R^3$, a hydrogen atom, a halogen atom, and an alkyl group are preferred, and the hydrogen atom and the alkyl group are more preferred. As $R^4$, a hydrogen atom and a halogen atom are preferred, and the hydrogen atom is particularly preferred in the context of a steepness of an absorption spectrum, in particular, steepness of change in a vicinity of a boundary between the visible region and the near-infrared region.

Note that in this specification, "the saturated or unsaturated ring structure" means a hydrocarbon ring and a hetero ring having an oxygen atom as a ring-constituting atom unless otherwise noted. In this case, a structure in which an alkyl group with a carbon number of 1 to 10 is bonded to a carbon atom constituting a ring is also included in a category of the saturated or unsaturated ring structure.

In Formula (AI), the groups $R^1$ to $R^4$, held by each of the benzene rings bonded to the squarylium skeleton on the left and right sides, and the rings Z each forming a condensed ring adjacent to the benzene ring may be different on the left and right sides, but are preferably the same in the context of productivity.

The NIR dye (AI) contains a compound represented by Formula (AI-1) having a resonance structure of Formula (AI). Symbols in Formula (AI-1) are the same as the definitions in Formula (AI).

[Chemical Formula 3]

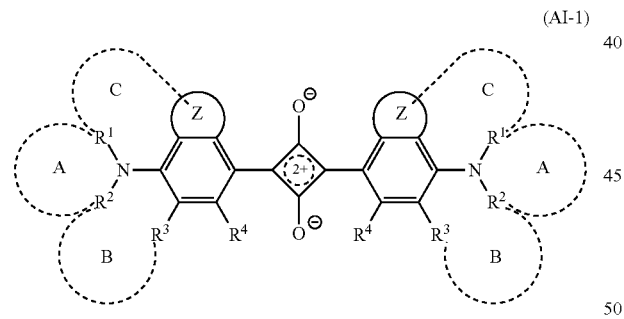

(AI-1)

Since the NIR dye (AI) has a structure where specific hetero rings are condensed at the second position and the third position of each of the benzene rings bonded to the squarylium skeleton on the left and right sides, it is possible to further increase a transmittance of light with a wavelength of 430 to 550 nm, in particular, in the visible region while including a high absorption characteristic with respect to near-infrared light. It is conceivable that planarity of molecules can be increased by changing the benzene ring into the condensed hetero ring. In a case when the hetero ring is the aromatic hetero ring, it is possible to further increase the visible light transmittance because electrons of the heteroatom can be delocalized.

The NIR dye (AI) has good solubility to an organic solvent, and its compatibility to the transparent resin is also good. As a result, even when a thickness of an absorption layer is reduced, an excellent spectral characteristic is exhibited, resulting in that the optical filter can be reduced in thickness. It is therefore possible to suppress thermal expansion of the absorption layer due to heating, and it is possible to suppress occurrence of cracks or the like in a reflection layer and a functional layer such as an anti-reflection layer at a heat treatment time when they are formed.

Concrete examples of the NIR dye (AI) include dyes formed of compounds represented by Formulas (A11) to (A15), (A21) to (A26), and (A31).

[Chemical Formula 5]

(A11)
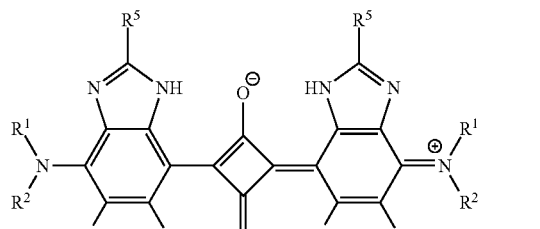

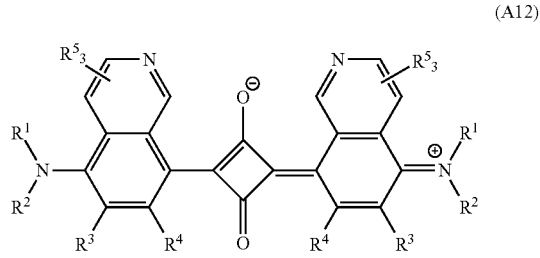
(A12)

(A13)
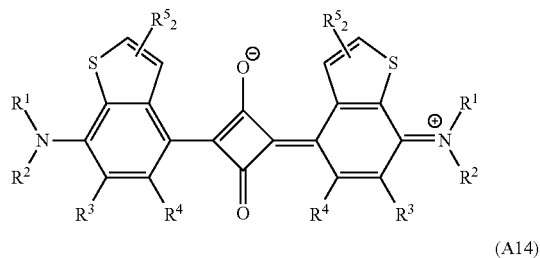

(A14)
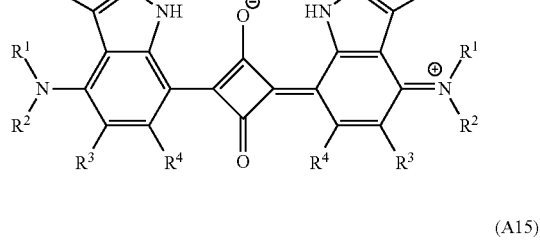

(A15)
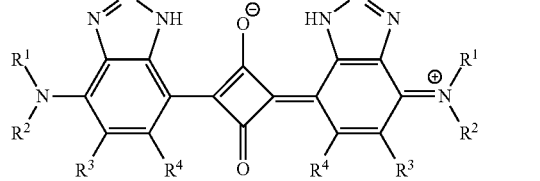

[Chemical Formula 6]

(A21)
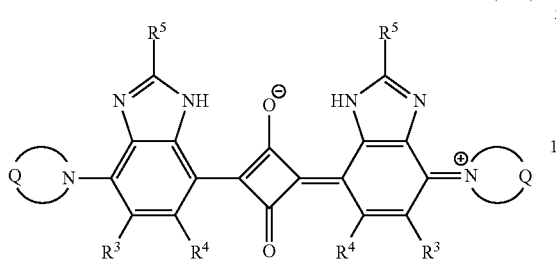

(A22)
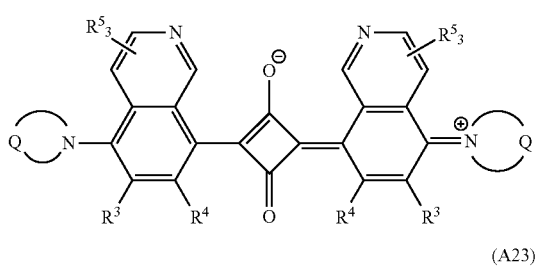

(A23)
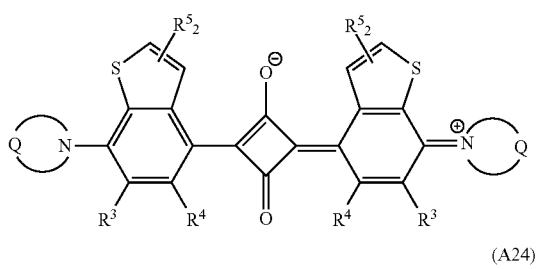

(A24)
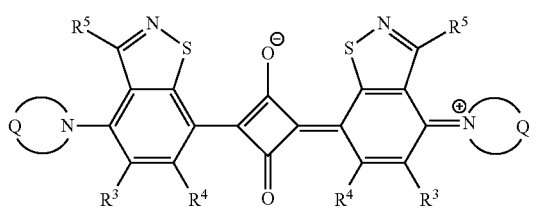

[Chemical Formula 7]

(A25)
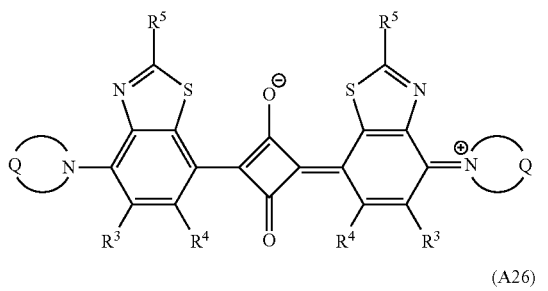

(A26)
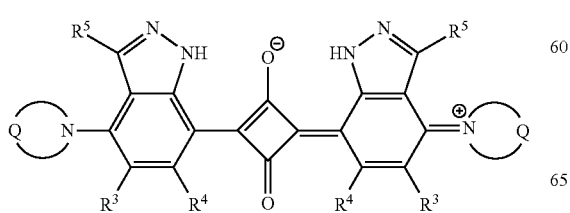

(A31)
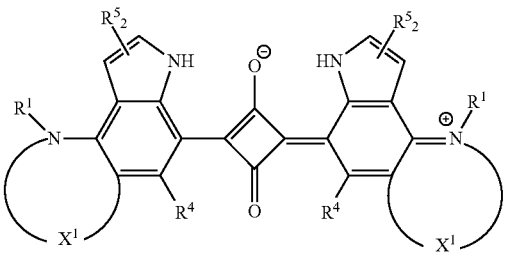

$R^1$, $R^2$, $R^3$ and $R^4$ in Formulas (A11) to (A15) are the same as the definitions of $R^1$, $R^2$, $R^3$ and $R^4$ when the rings A to C are not formed in Formula (AI), $R^3$ and $R^4$ in Formulas (A21) to (A26) are the same as the definitions of $R^3$ and $R^4$ when the ring C is not formed in Formula (AI), and $R^1$ and $R^4$ in Formula (A31) are the same as the definitions of $R^1$ and $R^4$ when the ring A is not formed in Formula (AI). $R^5$ in Formulas (A11) to (A14), (A21) to (A26), and (A31) each independently are a group selected from a hydrogen atom, a halogen atom, a hydroxyl group, a carboxy group, a sulfo group, a cyano group, an amino group, an N-substituted amino group, a nitro group, an alkoxycarbonyl group, a carbamoyl group, an N-substituted carbamoyl group, an imide group, and an alkyl group or an alkoxy group with a carbon number of 1 to 12. The alkyl group, and the alkyl group which forms the alkoxy group may be any of linear chain, branched chain, and cyclic, and may contain an unsaturated bond. Further, bivalent groups Q in Formulas (A21) to (A26) each represent a bivalent group where $R^1$ and $R^2$ are bonded when the ring A is formed in Formula (AI), and bivalent groups $X^1$ in Formula (A31) each represent a bivalent group where $R^2$ and $R^3$ are bonded when the ring B is formed in Formula (AI).

In Formulas (A11) to (A15), $R^1$ and $R^2$ are independently preferably an alkyl group with a carbon number of 1 to 20 which may contain a heteroatom between carbon atoms, and more preferably an alkyl group with a carbon number of 2 to 12 which may contain a heteroatom between carbon atoms, for example, groups (1a) to (5a), in the context of the visible light transmittance, the solubility to the transparent resin, and the like.

[Chemical Formula 8]

(1a)
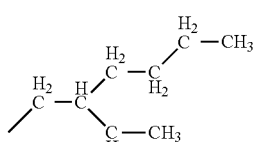

(2a)
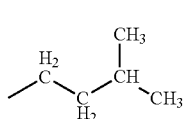

(3a)
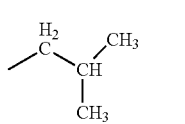

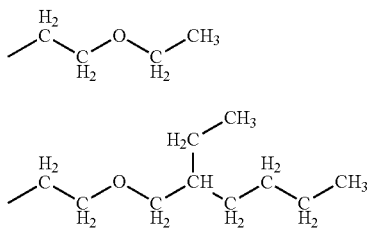

(4a)

(5a)

In formulas (A11) to (A15), (A21) to (A26), $R^3$ are each independently preferably a hydrogen atom, a halogen atom, an alkyl group, or an alkoxy group with a carbon number of 1 to 3 (for example, a methyl group, an ethyl group, a methoxy group, an ethoxy group, and so on), and more preferably the hydrogen atom, the halogen atom, and the methyl group in the context of the solubility to the transparent resin, the visible light transmittance, and so on. $R^4$ are each preferably a hydrogen atom, a halogen atom, and particularly preferably the hydrogen atom in the context of a steepness of change in a vicinity of a boundary between the visible region and the near-infrared region.

Further, in Formulas (A11) to (A14), (A21) to (A26), and (A31), $R^5$ are each independently preferably a hydrogen atom, a halogen atom, a nitro group, a trifluoromethyl group, a cyano group, an alkoxycarbonyl group, and more preferably the hydrogen atom, the nitro group, and the trifluoromethyl group.

In Formulas (A21) to (A26), examples of the bivalent group Q include an alkylene group or an alkyleneoxy group where a hydrogen atom may be substituted with an alkyl group with a carbon number of 1 to 10, an aryl group with a carbon number of 6 to 10, and a substitutable acyloxy group with a carbon number of 1 to 10. A position of oxygen in case of the alkyleneoxy group is preferably a position other than next to N. As the bivalent group Q, the alkylene group with a carbon number of 3 to 5 is particularly preferred.

In Formula (A31), a preferable aspect of each bivalent group $X^1$ is the same as the aforementioned bivalent group Q.

In Formula (A31), each $R^1$ may be independently preferably an alkyl group with a carbon number of 1 to 12 which may be branched and may contain a heteroatom between carbon atoms, more preferably the alkyl group with a carbon number of 2 to 8, and each $R^4$ is preferably a hydrogen atom, a halogen atom, and particularly preferably the hydrogen atom in the context of the solubility to the transparent resin, the visible light transmittance, and so on.

Examples of preferable dyes as the NIR dye (AI) are listed in Table 1. Concrete structures of $R^1$ and $R^2$ in Table 1 respectively correspond to Formulas (1a) to (5a). A dye (A3-1) is a dye formed of a compound represented by Formula (A3-1). In dyes (A1-1) to (A1-19), two pieces of $R^1$ in total existing one on each of the left and right sides are the same, and the same thing applies to $R^2$ to $R^5$. The same thing also applies to Q and $R^3$ to $R^5$ in dyes (A2-1) to (A2-6).

TABLE 1

| Abbreviation of dye | Structural formula | $R^1$ | $R^2$ | Q | $R^3$ | $X^1$ | $R^4$ | $R^5$ |
|---|---|---|---|---|---|---|---|---|
| A1-1 | A11 | (1a) | (1a) | — | H | — | H | H |
| A1-2 |  | (1a) | (1a) | — | H | — | H | —C(CH$_3$)$_3$ |
| A1-3 |  | (1a) | (1a) | — | H | — | H | —CF$_3$ |
| A1-4 |  | (1a) | (1a) | — | H | — | H | —CH$_3$ |
| A1-5 |  | (1a) | (1a) | — | H | — | H | —C$_8$H$_{17}$ |
| A1-6 | A12 | (1a) | (1a) | — | H | — | H | H |
| A1-7 | A13 | (1a) | (1a) | — | H | — | H | H |
| A1-8 | A14 | (2a) | (2a) | — | H | — | H | H |
| A1-9 |  | (1a) | (1a) | — | H | — | H | H |
| A1-10 |  | (3a) | (3a) | — | H | — | H | H |
| A1-11 |  | (4a) | (4a) | — | H | — | H | H |
| A1-12 |  | (5a) | (5a) | — | H | — | H | H |
| A1-13 | A11 | (2a) | (2a) | — | H | — | H | H |
| A1-14 |  | (3a) | (3a) | — | H | — | H | H |
| A1-15 |  | (4a) | (4a) | — | H | — | H | H |
| A1-16 |  | (5a) | (5a) | — | H | — | H | H |
| A1-17 |  | (1a) | —C$_2$H$_5$ | — | H | — | H | H |
| A1-18 |  | —(CH$_2$)$_5$CH$_3$ | —(CH$_2$)$_3$CH$_3$ | — | H | — | H | H |
| A1-19 | A15 | (1a) | (1a) | — | H | — | H | H |
| A2-1 | A21 | — | — | —(CH$_2$)$_4$— | H | — | H | H |
| A2-2 | A21 | — | — | —(CH$_2$)$_4$— | H | — | H | —C$_6$H$_{13}$ |
| A2-3 | A22 | — | — | —(CH$_2$)$_4$— | H | — | H | H |
| A2-4 | A23 | — | — | —(CH$_2$)$_4$— | H | — | H | H |
| A2-5 | A24 | — | — | —(CH$_2$)$_4$— | H | — | H | H |
| A2-6 | A25 | — | — | —(CH$_2$)$_4$— | H | — | F | —CH$_3$ |
| A3-1 | A31 | —CH(CH$_3$)$_2$ | — | — | — | —CH(CH$_3$)—C(CH$_3$)$_2$— | H | —CH$_3$, H |

[Chemical Formula 9]

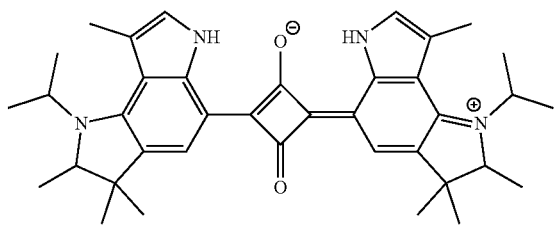

(A3-1)

The NIR dye (AI) can be produced by methods, for example, described in the specification of US Patent Application Publication No. 2014/0061505 and the specification of International Publication Pamphlet No. 2014/088063.

Concretely, the NIR dye (AI) can be produced by causing a reaction of 3,4-dihydroxy-3-cyclobutene-1,2-dione (squaric acid) with a compound having a condensed ring capable of forming the structure represented by Formula (AI) by bonding to the squaric acid. For example, when the NIR dye (AI) has a bilaterally symmetrical structure, it is only necessary to cause a reaction of the compound with an equivalent weight of 2 having a condensed ring of a desired structure in the above-described range with the squaric acid with an equivalent weight of 1.

As a concrete example, the following describes a reaction path at a time of obtaining the NIR dye (A1). The squaric acid is represented by (s) in Scheme (F1). According to Scheme (F1), a substituted amino group having desired substituents ($R^1$, $R^2$) is introduced (c) into a benzene ring of a benzothiadiazole compound (a) having desired substituents ($R^3$, $R^4$), and then reduced to thereby obtain a phenylenediamine compound (d). Further, carboxylic acid (e) or aldehyde (f) having a desired substituent $R^5$ is reacted therewith, thereby obtaining a benzimidazole compound (g). The benzimidazole compound (g) with an equivalent weight of 2 is reacted with the squaric acid (s) with an equivalent weight of 1, thereby obtaining the dye (A11).

[Chemical Formula 10]

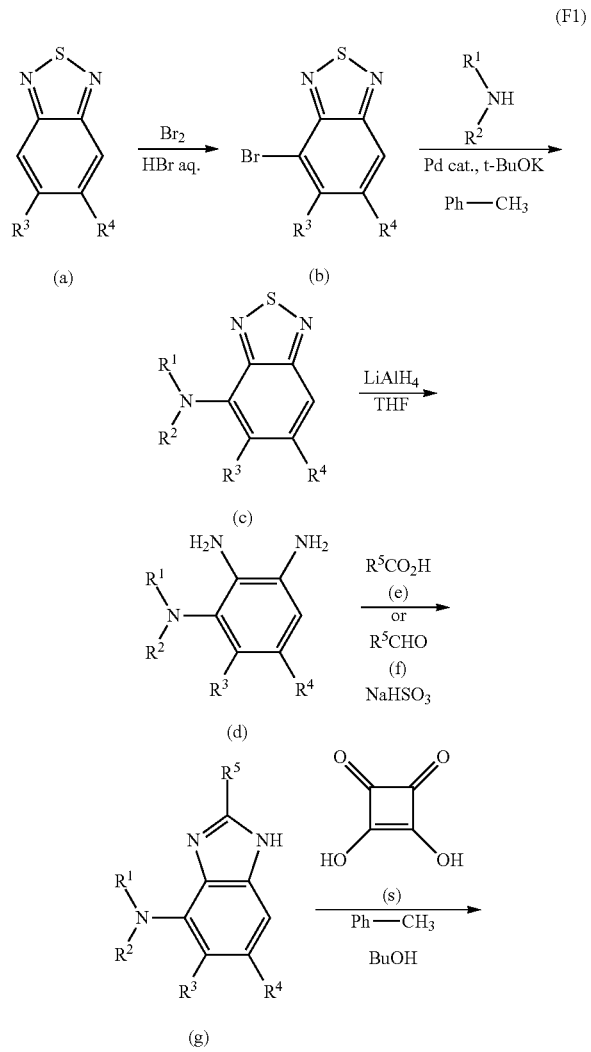

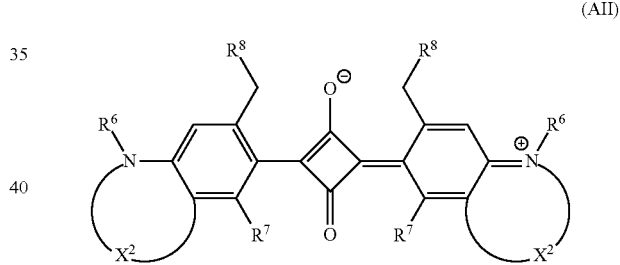

(A11)

In Scheme (F1), $R^1$ to $R^5$ are of the same meaning as $R^1$ to $R^5$ in Formula (A11), Me represents a methyl group, Et represents an ethyl group, Bu represents a butyl group, Ph represents a phenyl group, HBraq. represents hydrobromic acid, and THF represents tetrahydrofuran. Hereinafter, in the present specification, Me, Et, Bu, Ph, HBraq., and THF are used in the same meaning as described above.

<NIR Dye (AII)>

The NIR dye (AII) is formed of a squarylium-based compound having a structure, in which a squarylium skeleton is held in a center of a molecular structure and one benzene ring is bonded to the squarylium skeleton on each of left and right sides, where each benzene ring is bonded to a nitrogen atom at a fourth position, and a saturated heterocycle including the nitrogen atom is formed.

[Chemical Formula 11]

(AII)

In Formula (AII), $R^6$ each independently represent a hydrogen atom, or a hydrocarbon group which may contain an unsaturated bond, a heteroatom (oxygen atom, or the like), a saturated or unsaturated ring structure between carbon atoms, and which may have a substituent. Examples of a substituent include a halogen atom, a hydroxyl group, a carboxy group, a sulfo group, a cyano group, an amino group, an N-substituted amino group, a nitro group, an alkoxycarbonyl group, a carbamoyl group, an N-substituted carbamoyl group, an imide group, an alkyl group or an alkoxy group with a carbon number of 1 to 12, and so on. The alkyl group, and the alkyl group which forms the alkoxy group may be any of linear chain, branched chain, and cyclic. As $R^6$, an alkyl group with a carbon number of 1 to 20 which may be branched and may contain a heteroatom between carbon atoms is preferred, an alkyl group with a carbon number of 1 to 12 is more preferred, and an alkyl group with a carbon number of 2 to 8 is further preferred, in the context of the visible light transmittance, the solubility to the transparent resin, and the like.

$R^7$ each independently represent a hydrogen atom, a halogen atom, a hydroxyl group or an alkyl group or an alkoxy group, preferably the alkyl group or the alkoxy group with a carbon number of 1 to 20. The alkyl group, and the alkyl group which forms the alkoxy group may be any of linear chain, branched chain, and cyclic. As $R^7$, a hydrogen atom and a halogen atom are preferred, and the hydrogen atom is particularly preferred in the context of a steepness of an absorption spectrum, in particular, the steepness of change in the vicinity of the boundary between the visible region and the near-infrared region.

$R^8$ each independently represent a halogen atom, a hydroxyl group, an alkoxy group with a carbon number of 1 to 12, an acyl group or an acyloxy group with a carbon number of 1 to 12, a perfluoroalkyl group with a carbon number of 1 to 12, or a —$SO_2R^9$ group (where $R^9$ represents an alkyl group with a carbon number of 1 to 12 which may have a substituent). As $R^8$, the halogen atom, the hydroxyl group, and the —$SO_2R^9$ group (where $R^9$ is the alkyl group with the carbon number of 1 to 12) are preferred, and a fluorine atom, the hydroxyl group, and a —$SO_2$Me are particularly preferred in the context of increasing acidity of an adjacent hydrogen atom at a benzylic position.

Examples of a bivalent group $X^2$ include an alkylene group or an alkyleneoxy group where a hydrogen atom may be substituted with an alkyl group with a carbon number of 1 to 10, an aryl group with a carbon number of 6 to 10, and a substitutable acyloxy group with a carbon number of 1 to 10. A position of oxygen in case of the alkyleneoxy group is preferably at a position other than next to N. The alkylene group with the carbon number of 2 to 5 is particularly preferred as $X^2$.

In Formula (AII), groups $R^6$ to $R^8$, $X^2$ held by each of the benzene rings bonded to the left and right sides of the squarylium skeleton may be different on the left and right sides, but preferably the same in the context of productivity.

The NIR dye (AII) contains a compound represented by Formula (AII-1) having a resonance structure of Formula (AII). Symbols in Formula (AII-1) are the same as the definitions in Formula (AII).

[Chemical Formula 12]

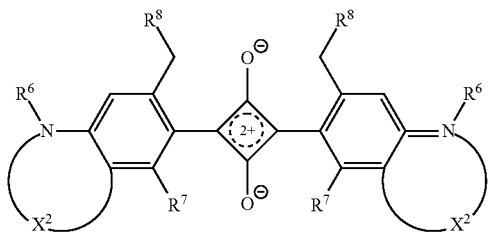

(AII-1)

Since the NIR dye (AII) does not have a nitrogen atom having an unpaired electron but have a hydrogen atom with high acidity at a benzylic position next to $R^8$, it is possible to further increase the transmittance of light particularly with a wavelength of 430 to 550 nm in the visible region while having the high absorption characteristic with respect to the near-infrared light.

More concrete examples of the NIR dye (AII) include a dye formed of a compound represented by Formula (A41).

[Chemical Formula 13]

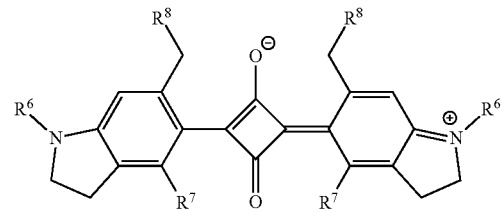

(A41)

Symbols $R^6$ to $R^8$ in Formula (A41) are the same as the definitions in Formula (AII), and preferable aspects are also the same.

Examples of preferable dyes as the NIR dye (AII) are listed in Table 2. In dyes (A4-1) to (A4-3), two pieces of $R^6$ in total existing one on each of the left and right sides are the same in left and right, and the same thing applies to $R^7$, $R^8$.

TABLE 2

| Abbreviation of dye | Structural formula | $R^6$ | $R^7$ | $R^8$ |
|---|---|---|---|---|
| A4-1 | A41 | —CH(CH$_3$)$_2$ | H | F |
| A4-2 | A41 | —CH(CH$_3$)$_2$ | H | OH |
| A4-3 | A41 | —CH(CH$_3$)$_2$ | H | —SO$_2$CH$_3$ |

In this embodiment, for example, when the NIR dye (AI) and the NIR dye (AII) are used as the dyes (A), dyes other than the NIR dye (AI) and the NIR dye (AII) may be contained within the range not impairing the effects of the present disclosure, but it is preferred to use only the NIR dye (AI) or only the NIR dye (AII) in the context of improving the visible light transmittance. As each of the NIR dye (AI) and the NIR dye (AII), one may be used solely, or two or more may be mixed and used.

A content of the dye (A) in the absorption layer is preferably 0.1 to 30 parts by mass relative to 100 parts by mass of the transparent resin (B). Having 0.1 parts by mass or more enables to obtain a desired near-infrared absorbing capability, and having 30 parts by mass or less suppresses a decrease of near-infrared absorbing capability, an increase in a haze value, and the like. The content of the dye (A) is more preferably 0.5 to 25 parts by mass, and further preferably 1 to 20 parts by mass.

(Ultraviolet Absorbing Dye (U))

The absorption layer can contain the dye (U), in addition to the dye (A) and the transparent resin (B). Concrete examples of the dye (U) include an oxazole-based dye, a merocyanine-based dye, a cyanine-based dye, a naphthalimide-based dye, an oxadiazole-based dye, an oxazine-based dye, an oxazolidine-based dye, a naphthalic acid-based dye, a styryl-based dye, an anthracene-based dye, a cyclic carbonyl-based dye, a triazole-based dye, and the like. Among them, the oxazole-based dye and the merocyanine-based dye are preferred. As the dye (U), one may be used solely, or two or more may be used together in the absorption layer.

(Transparent Resin (B))

Examples of the transparent resin (B) include an acrylic resin, an epoxy resin, an ene-thiol resin, a polycarbonate resin, a polyether resin, a polyarylate resin, a polysulfone resin, a polyethersulfone resin, a polyparaphenylene resin, a polyarylene ether phosphine oxide resin, a polyimide resin, a polyamide-imide resin, a polyolefin resin, a cyclic olefin resin, and a polyester resin such as a polyethylene terephthalate resin and a polyethylene naphthalate resin, and the like. One may be used solely from these resins, or two or more may be mixed and used.

Among the above-described resins, a resin having a high glass transition point (Tg) is preferred as the transparent resin in the context of transparency, solubility of the dye (A) or the dye (A) and the dye (U) to the transparent resin (B), and heat resistance. Concretely, the transparent resin (B) is preferably one or more selected from the polyester resin, the polycarbonate resin, the polyethersulfone resin, the polyarylate resin, the polyimide resin, and the epoxy resin, more preferably one or more selected from the polyester resin and the polyimide resin.

(Other Components)

The absorption layer may further contain, within the range not impairing the effects of the present disclosure, arbitrary components such as an adhesion-imparting agent, a color tone correcting dye, a leveling agent, an antistatic agent, a heat stabilizer, a light stabilizer, an antioxidant, a dispersing agent, a flame retardant, a lubricant, and a plasticizer.

The absorption layer can be formed by, for example, preparing a coating liquid by dissolving or dispersing the dye (A), the dye (U), and the transparent resin (B) or raw material components of the transparent resin (B), as well as components blended as necessary in a solvent, applying this on a substrate and drying it, and moreover curing it as necessary. The above-described substrate may be a transparent substrate included in the present filter or a releasable substrate used only when the absorption layer is formed. The solvent can be a dispersion medium capable of stably dispersing the components or a solvent capable of dissolving the components.

The coating liquid can contain a surface active agent to thereby improve voids due to minute bubbles, dents due to adherence of foreign objects or the like, and crawling in a drying process, and the like. For applying the coating liquid, for example, an immersion coating method, a cast coating method, a spin coating method, or the like can be used. After the above-described coating liquid is applied on the substrate, it is dried to form the absorption layer. When the coating liquid contains the raw material components of the transparent resin, a curing treatment such as thermal-curing and photo-curing is further performed.

The absorption layer can be produced in a film form by extrusion molding, and moreover, this film may be stacked on another member and integrated by thermocompression, or the like. For example, when the present filter includes the transparent substrate, this film may be adhered on the transparent substrate.

[Reflection Layer]

The reflection layer preferably has a wavelength selection characteristic to transmit visible light and mainly reflect light with a wavelength other than a light blocking region of the absorption layer. In this case, the reflection region of the reflection layer may include a light blocking region in the near-infrared region of the absorption layer.

The reflection layer is formed of a dielectric multilayer film made by alternately stacking a dielectric film with a low refractive index (low-refractive-index film) and a dielectric film with a high refractive index (high-refractive-index film). Examples of high-refractive-index film materials include $Ta_2O_5$, $TiO_2$, and $Nb_2O_5$. Among them, $TiO_2$ is preferred from points of reproducibility, stability, and the like in film formability, a refractive index, and the like. Examples of low-refractive-index film materials include $SiO_2$, $SiO_xN_y$, and the like, and $SiO_2$ is preferred from points of reproducibility, stability, economic efficiency, and the like in film formability. A film thickness of the reflection film is preferably 2 to 10 μm.

The dielectric multilayer film controls transmitting and blocking of light in a specific wavelength region by utilizing interference of light, and there is incident angle dependence in its transmitting and blocking characteristics. In general, a wavelength of light blocked by reflection is a shorter wavelength in case of light incident obliquely than light incident perpendicularly (incident angle of 0°).

The reflection layer preferably satisfies the following (ii-1) and (ii-2).

(ii-1) A transmittance of light with a wavelength of 420 to 695 nm is 90% or more in each of spectral transmittance curves at incident angles of 0° and 30°.

(ii-2) A transmittance of light with a wavelength of $\lambda_b$ to 1100 nm is 1% or less in each of spectral transmittance curves at incident angles of 0° and 30° (where $\lambda_b$ is a maximum wavelength with which a transmittance of light with a wavelength of 650 to 800 nm of the absorption layer becomes 1%).

In (ii-1), the transmittance of light with the wavelength of 420 to 695 nm is preferably 93% or more, more preferably 95% or more, further preferably 97% or more.

In (ii-2), the transmittance of light with the wavelength of $\lambda_b$ to 1100 nm is more preferably 0.5% or less.

When the reflection layer satisfies (ii-1) and (ii-2), the present filter can easily obtain the spectral transmittance characteristics satisfying the requirements (iii-1) to (iii-6).

[Anti-Reflection Layer]

Examples of the anti-reflection layer include a dielectric multilayer film, an intermediate refractive index medium, a moth-eye structure having a refractive index which gradually changes, and the like. In the context of obtaining high optical efficiency and productivity, the dielectric multilayer film is preferred.

[Transparent Substrate]

In the case of using the transparent substrate, a thickness of the transparent substrate is preferably 0.03 to 5 mm, and more preferably 0.05 to 1 mm from a point of thickness reduction, and glass, (birefringent) crystal, or various resins such as a polyimide resin can be used as long as the transparent substrate is one that transmits visible light.

Examples of the glass that can be used for the transparent substrate include absorption-type glass made by adding CuO or the like to fluorophosphate-based glass, phosphate-based glass, or the like (near-infrared absorbing glass substrate), soda lime glass, borosilicate glass, non-alkali glass, quartz glass, and the like. Note that "phosphate glass" includes silicophosphate glass in which part of a skeleton of the glass is formed of $SiO_2$.

When the transparent substrate is the fluorophosphate-based glass, concretely, the glass preferably contains, in cation %, 20 to 45% $P^{5+}$, 1 to 25% $Al^{3+}$, 1 to 30% $R^+$ (where $R^+$ is at least one of $Li^+$, $Na^+$, and $K^+$, and the above value is a value where respective contents are added), 1 to 20% $Cu^{2+}$, 1 to 50% $R^{2+}$ (where $R^{2+}$ is at least one of $Mg^{2+}$, $Ca^{2+}$, $Sr^{2+}$, $Ba^{2+}$, and $Zn^{2+}$, and the above value is a value where respective contents are added), and further contains, in anion %, 10 to 65% F, and 35 to 90% $O^{2-}$.

When the transparent substrate is the phosphate-based glass, the glass preferably contains, in mass %, 30 to 80% $P_2O_5$, 1 to 20% $Al_2O_3$, 0.5 to 30% $R_2O$ (where $R_2O$ is at least one of $Li_2O$, $Na_2O$, and $K_2O$, and the above value is a value where respective contents are added), 1 to 12% CuO, 0.5 to 40% RO (where RO is at least one of MgO, CaO, SrO, BaO, and ZnO, and the above value is a value where respective contents are added).

Examples of commercial products include NF-50E, NF-50EX, NF-50T, NF-50TX (manufactured by Asahi Glass Co., Ltd., product names), or the like, BG-60, BG-61 (manufactured by Schott AG, product names), or the like, and CD 5000 (manufactured by HOYA Corporation, product name), or the like.

The above-described CuO-containing glass may further contain a metal oxide. For example, when one or two or more of $Fe_2O_3$, $MoO_3$, $WO_3$, $CeO_2$, $Sb_2O_3$, $V_2O_5$, and the like are contained as the metal oxide, the CuO-containing glass has an ultraviolet absorption characteristic. Contents of these metal oxides are preferably such that at least one selected from a group made up of $Fe_2O_3$, $MoO_3$, $WO_3$, and $CeO_2$ is contained by 0.6 to 5 parts by mass $Fe_2O_3$, 0.5 to 5 parts by mass $MoO_3$, 1 to 6 parts by mass $WO_3$, and 2.5 to 6 parts by mass $CeO_2$, or two of $Fe_2O_3$ and $Sb_2O_3$ are contained by 0.6 to 5 parts by mass $Fe_2O_3$+0.1 to 5 parts by mass $Sb_2O_3$, or two of $V_2O_5$ and $CeO_2$ are contained by 0.01 to 0.5 parts by mass $V_2O_5$+1 to 6 parts by mass $CeO_2$, relative to 100 parts by mass of the CuO-containing glass.

When the present filter includes glass or absorption-type glass as the transparent substrate 13, it is also possible to provide a not-illustrated dielectric layer between the glass or the absorption-type glass (transparent substrate 13) and the absorption layer 11 (11a, 11b) with a thickness of 30 nm or more for the purpose of improvement of durability of the absorption layer.

When the transparent substrate made of glass contains, for example, alkaline atoms such as Na atoms and K atoms, and these alkaline atoms diffuse through the absorption layer, which may deteriorate the optical characteristic and weather resistance of the absorption layer, the dielectric layer functions as an alkali barrier film, which enables to improve the durability of the present filter. In the above-described case, examples of the dielectric layer preferably include $SiO_2$, $SiO_x$, $Al_2O_3$, and so on. When the dielectric layer is provided between the glass or the near-infrared absorption glass (absorption-type glass) and the absorption layer, one where the dielectric layer is provided on the glass or the near-infrared absorption glass is also treated as the "transparent substrate".

EXAMPLE

Example 1 to Example 22 are examples of an optical filter according to the present disclosure.

<Synthesis of Dye>

NIR Dyes (A1-1) to (A1-19), (A2-1) to (A2-6), (A3-1), (A4-1) to (A4-3), and (C1) to (C3) were synthesized. The NIR dyes (C1) and (C3) are the dyes represented by the following structural formulas, and the NIR dye (C2) is a later-described commercial product.

[Chemical Formula 14]

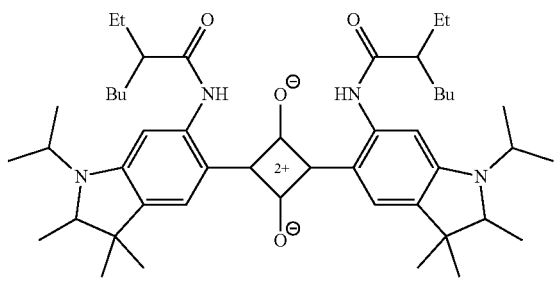

(C1)

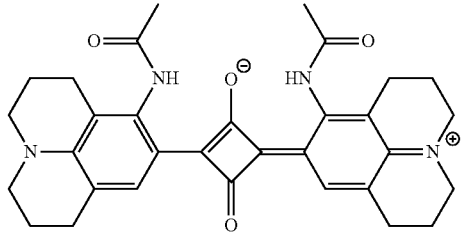

(C3)

[Production of NIR Dye (A1-1)]

The following concretely describes a production example of the dye (A1-1) by using Scheme (F1). In the following explanation, although a description is not made on $R^1$ to $R^5$ in raw material components and (intermediate) products, $R^1$ and $R^2$ are each a 2-ethylhexyl group, and $R^3$ to $R^5$ are each a hydrogen atom.

In the production of the NIR dye (A1-1), a compound (a) in Scheme (F1), that is 2,1,3-benzothiadiazole was obtained from Tokyo Chemical Industry Co., Ltd., and used as a starting material.

(Production of Compound (b))

To a flask equipped with a reflux device, 25.0 g (183.7 mmol) of the compound (a), and 150 mL of 48% hydrobromic acid were added. After heating to 100° C., 8.5 mL (165.4 mmol) of bromine was dropped, the resultant was stirred at 100° C. for nine hours, and then it was let cool. After a reaction was finished, 200 mL of dichloromethane was added, precipitated solid was dissolved, and further 100 mL of an aqueous sodium sulfate solution was added. An organic layer was collected, washed with a saturated aqueous sodium hydrogen carbonate solution, dried with anhydrous sodium sulfate, and then a solvent was removed under reduced pressure to obtain an unrefined compound (b). The compound (b) was suspended in 200 mL of hexane/ethyl acetate (4:1, volume ratio), remaining solids were filtered to thereby remove 4,7-dibromo-2,1,3-benzothiadiazole being a by-product. The filtrate was condensed again, suspended in 200 mL of hexane, and remaining solids were filtered, to thereby obtain 11.2 g of the compound (b). Further, the filtrate was condensed, and refinement was performed by a column chromatography method using hexane/ethyl acetate (97:3, volume ratio) as a developing solution, to thereby obtain 8.0 g of the compound (b). A sum total was 19.2 g (89.3 mmol), and a yield was 49%.

(Production of Compound (c))

To a flask equipped with a reflux device, 3.3 g (29.0 mmol) of t-butoxypotassium, 0.3 g (0.5 mmol) of PEPPSI™-IPr (manufactured by Sigma-Aldrick corporation, product name) as a Pd catalyst, 150 mL of toluene, 5.2 g (24.1 mmol) of the compound (b), and 8.0 mL (26.5 mmol)

of bis(2-ethylhexyl)amine were added, and it was refluxed at 120° C. for five hours under a nitrogen atmosphere. After a reaction was finished, solids in a reaction solution were removed by filtration, the filtrate was condensed, and then refinement was performed by column chromatography using hexane/ethyl acetate (99:1, volume ratio) as a developing solution, to thereby obtain a compound (c) (5.3 g, 14 mmol, yield: 58%).

(Production of Compound (d))

To a flask equipped with a reflux device, 3.6 g (9.5 mmol) of the compound (c), 100 mL of THF, and 0.9 g (23.8 mmol) of lithium aluminum hydride were added, and it was refluxed at 75° C. for one hour under a nitrogen atmosphere. After that, 0.9 mL of water, 0.9 mL of a 15% aqueous sodium hydroxide solution, 2.7 mL of water were sequentially added while cooling with ice to stop a reaction. Solids in a reaction solution were removed by filtration, the filtrate was condensed to obtain an unrefined compound (d). The unrefined compound (d) was directly used for a next reaction.

(Production of Compound (g))

To a flask equipped with a reflux device, the obtained compound (d) and 50 mL of 90% formic acid were added, and it was refluxed at 100° C. for two hours. After a reaction was finished, the formic acid was removed under reduced pressure, then 50 mL of ethyl acetate and 50 mL of a saturated aqueous sodium hydrogen carbonate solution were added thereto. An organic layer was collected, dried with anhydrous sodium sulfate, and then a solvent was removed under reduced pressure. The resultant was refined by column chromatography using hexane/ethyl acetate (2:1, volume ratio) as a developing solution, to thereby obtain a compound (g) (2.7 g, 7.4 mmol). A yield from the compound (c) was 78%.

(Production of NIR Dye (A1-1))

To a flask equipped with a reflux device and a diversion device, 2.7 g (7.4 mmol) of the compound (g), 0.5 g (4.5 mmol) of squaric acid, 30 mL of toluene, and 30 mL of 1-butanol were added, and it was refluxed at 125° C. for eight hours while stirring. After a reaction was finished, a solvent was removed under reduced pressure, and then refinement was performed by column chromatography using hexane/ethyl acetate (9:1, volume ratio) as a developing solution, to thereby obtain a NIR dye (A1-1) (2.4 g, 3.0 mmol, yield: 81%).

[Production of NIR Dye (A1-2)]

A NIR dye (A1-2) was produced as same as the case of the NIR dye (A1-1) except that under existence of sodium hydrogen sulfite instead of the formic acid, the compound (d) was reacted with pivaloyl aldehyde while using N,N-dimethylacetamide (DMAc) as a solvent, to produce the compound (g) (where $R^5$ was a tert-butyl group) in the process of producing the compound (g) from the compound (d).

Concretely, the process of producing the compound (g) from the compound (d) was performed as follows.

To a flask equipped with a reflux device, 2.8 g (7.5 mmol) of the unrefined compound (d), 20 mL of DMAc, and 0.8 g (7.5 mmol) of sodium hydrogen sulfite were added. After heated to 100° C., a solution where 0.8 mL (7.5 mmol) of pivaloyl aldehyde and 20 mL of DMAc were mixed was dropped for 15 minutes, and further, it was refluxed at 100° C. for two hours. After a reaction was finished, a solvent was removed under reduced pressure, then 50 mL of ethyl acetate and 50 mL of a saturated aqueous sodium hydrogen carbonate solution were added thereto. An organic layer was collected, dried with anhydrous sodium sulfate, a solvent was removed under reduced pressure, and then refinement was performed by column chromatography using hexane/ethyl acetate (9:1, volume ratio) as a developing solution, to thereby obtain 2.3 g, (5.6 mmol) of the compound (g). A yield from the compound (c) was 74%.

[Production of NIR Dye (A1-3)]

A NIR dye (A1-3) was produced as same as the case of the NIR dye (A1-1) except that the compound (g) (where $R^5$ was $-CF_3$) was produced by using trifluoroacetic acid instead of the formic acid in the process of producing the compound (g) from the compound (d).

Concretely, the process of producing the compound (g) from the compound (d) was performed as follows.

To a flask equipped with a reflux device, 3.0 g (8.0 mmol) of the unrefined compound (d) and 40 mL of the trifluoroacetic acid were added, and it was refluxed at 75° C. for 18 hours. After a reaction was finished, the trifluoroacetic acid was removed under reduced pressure, then 50 mL of ethyl acetate and 50 mL of a saturated aqueous sodium hydrogen carbonate solution were added thereto. An organic layer was collected, dried with anhydrous sodium sulfate, a solvent was removed under reduced pressure, and then refinement was performed by column chromatography using hexane/ethyl acetate (95:5, volume ratio) as a developing solution, to thereby obtain the compound (g) (2.5 g, 5.9 mmol). A Yield from the Compound (c) was 73%.

[Production of NIR Dye (A1-4)]

A NIR dye (A1-4) was produced as same as the case of the NIR dye (A1-1) except that the compound (g) (where $R^5$ was $-CH_3$) was produced by using acetic acid instead of the formic acid in the process of producing the compound (g) from the compound (d).

[Production of NIR Dye (A1-5)]

A NIR dye (A1-5) was produced as same as the case of the NIR dye (A1-2) except that the compound (g) (where $R^5$ was $-C_8H_{17}$) was produced by using 1-nonanone instead of pivaloyl aldehyde in the process of producing the compound (g) from the compound (d).

[Production of NIR Dye (A1-13)]

A NIR dye (A1-13) was produced as same as the case of the NIR dye (A1-1) except that the compound (c) (where $R^1$ and $R^2$ were each the group (2a)) was produced by using diisoamylamine instead of bis(2-ethylhexyl)amine in the process of producing the compound (c) from the compound (b).

[Production of NIR Dye (A1-14)]

A NIR dye (A1-14) was produced as same as the case of the NIR dye (A1-1) except that the compound (c) (where $R^1$ and $R^2$ were each the group (3a)) was produced by using diisobutylamine instead of bis(2-ethylhexyl)amine in the process of producing the compound (c) from the compound (b).

[Production of NIR Dye (A1-15)]

A NIR dye (A1-15) was produced as same as the case of the NIR dye (A1-1) except that the compound (c) (where $R^1$ and $R^2$ were each the group (4a)) was produced by using bis(2-ethoxyethyl)amine instead of bis(2-ethylhexyl)amine in the process of producing the compound (c) from the compound (b).

[Production of NIR Dye (A1-16)]

A NIR dye (A1-16) was produced as same as the case of the NIR dye (A1-1) except that the compound (c) (where $R^1$ and $R^2$ were each the group (5a)) was produced by using bis(2-(2-ethylhexyloxy)ethyl)amine instead of bis(2-ethylhexyl)amine in the process of producing the compound (c) from the compound (b).

[Production of NIR dye (A1-17)]

A NIR dye (A1-17) was produced as same as the case of the NIR dye (A1-1) except that the compound (c) (where $R^1$ was the group (1a), and $R^2$ was —$C_2H_5$) was produced by using N-(2-ethylhexyl)ethylamine instead of bis(2-ethylhexyl)amine in the process of producing the compound (c) from the compound (b).

Here, a production example of N-(2-ethylhexyl)ethylamine used for the production of the dye (A1-17) is explained by using Scheme (F2) illustrated below. A compound (aa), that is 2-ethylhexylamine, obtained from Tokyo Chemical Industry Co., Ltd. was used as a starting material.

[Chemical Formula 15]

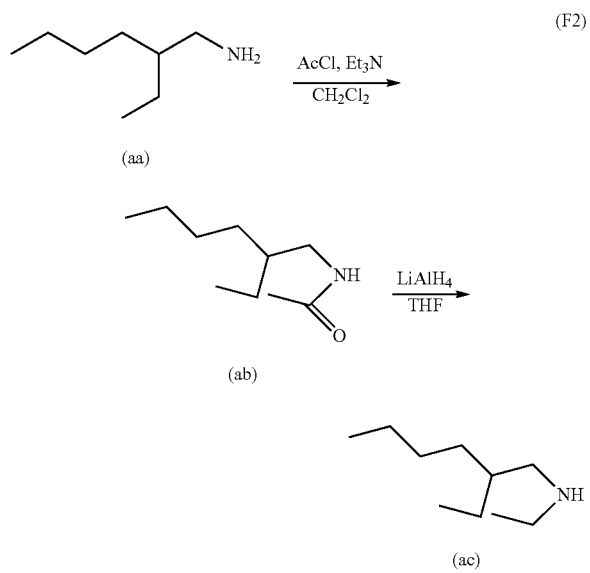

In Scheme (F2), Ac represents an acetyl group.

(Production of Compound (Ab))

To a flask, 8.59 mL (52.5 mmol) of the compound (aa), 7.67 mL (55.0 mmol) of triethylamine, and 150 mL of dichloromethane were added, 3.54 mL (50.0 mmol) of acetyl chloride was dropped at 0° C. under a nitrogen atmosphere, and it was stirred at 0° C. for one hour. After a reaction was finished, dichloromethane was removed under reduced pressure, 150 mL of ethyl acetate and 150 mL of 1 M hydrochloric acid were added, and an organic layer was collected. The organic layer was dried with anhydrous sodium sulfate and a solvent was removed under reduced pressure, to obtain an unrefined compound (ab), and the compound (ab) was directly used for a next reaction.

(Production of Compound (Ac))

To a flask equipped with a reflux device, the obtained compound (ab), 200 mL of THF, and 2.28 g (60.0 mmol) of lithium aluminum hydride were added, and it was refluxed at 75° C. for one hour under a nitrogen atmosphere. After that, 3.5 mL of a saturated aqueous sodium sulfate solution was added while cooling with ice to stop a reaction. Solids in a reaction solution were removed by filtration, the filtrate was condensed to obtain an unrefined compound (ac). The compound (ac) was refined through vacuum distillation to obtain the compound (ac) (7.24 g, 46.1 mmol, yield: 92%).

[Production of NIR Dye (A1-18)]

A NIR dye (A1-18) was produced as same as the case of the NIR dye (A1-1) except that the compound (c) (where $R^1$ was —$(CH_2)_5CH_3$, and $R^2$ was —$(CH_2)_3CH_3$) was produced by using N-butylhexylamine instead of bis(2-ethylhexyl)amine in the process of producing the compound (c) from the compound (b).

Here, a production example of N-butylhexylamine used for the production of the dye (A1-18) is explained by using Scheme (F3) illustrated below. A compound (ad), that is hexylamine, obtained from Tokyo Chemical Industry Co., Ltd. was used as a starting material.

[Chemical Formula 16]

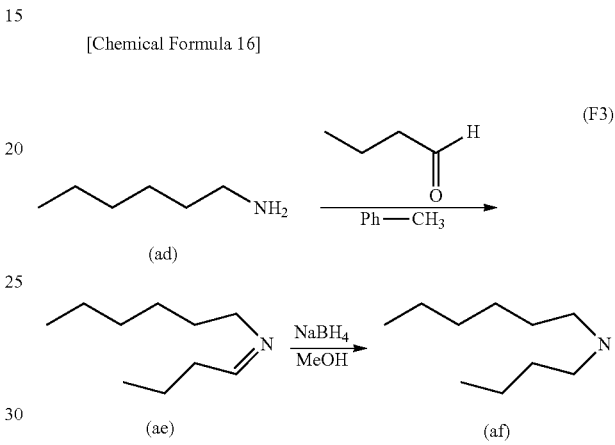

(Production of Compound (Ae))

To a flask equipped with a dropping funnel filled with molecular sieve and a reflux device, 6.57 mL of the compound (ad), 4.51 mL of butanol, and 50 mL of toluene were added, and it was refluxed at 135° C. for three hours. After a reaction was finished, toluene was removed under reduced pressure to obtain an unrefined compound (ae), and the compound (ae) was directly used for a next reaction.

(Production of Compound (af))

To a flask, the obtained compound (ae) and 50 mL of methanol were added, and 1.89 g (50.0 mmol) of sodium boron hydroxide was added at 0° C., then it was stirred at room temperature for one hour. After that, 30 mL of 1 M hydrochloric acid was added to stop a reaction. Methanol was removed under reduced pressure, then 50 mL of ethyl acetate was added, and an organic layer was collected. The organic layer was dried with anhydrous sodium sulfate, a solvent was removed under reduced pressure, and then refinement was performed by column chromatography using ethyl acetate/methanol (20:1, volume ratio) as a developing solution. As a result, a compound (af) (1.76 g, 11.2 mmol, yield: 22%) was obtained.

[Production of NIR Dye (A1-19)]

The following concretely describes a production example of a NIR dye (A1-19) by using Scheme (F4). In Scheme (F4), $R^1$ and $R^2$ are each a 2-ethylhexyl group, and $R^3$ and $R^4$ are each a hydrogen atom. Besides, Ac represents an acetyl group.

In the production of the dye (A1-19), the compound (c) which was produced from 2,1,3-benzothiadiazole (the compound (a) in Scheme (F1)) was used as a starting material as same as the case of the NIR dye (A1-1).

[Chemical Formula 17]

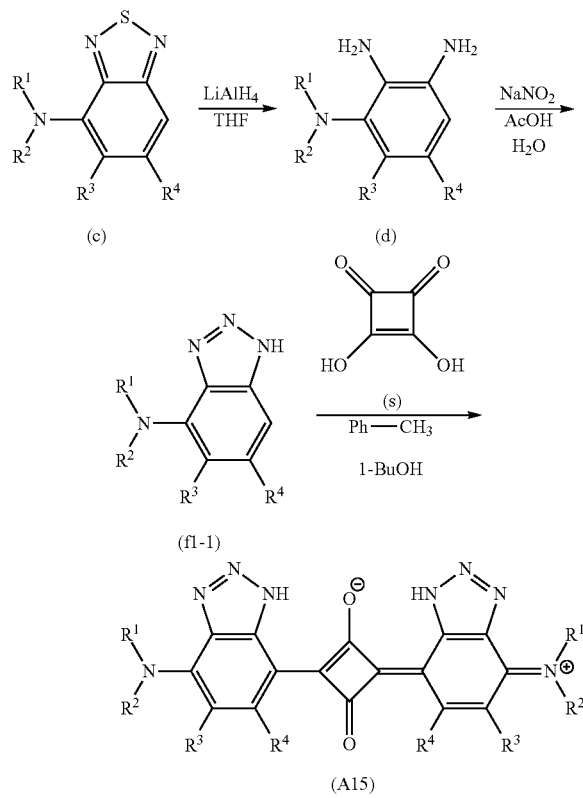

(Production of Compound (d))

To a flask equipped with a reflux device, 6.1 g (16.2 mmol) of the compound (c), 130 mL of THF, and 1.5 g (40.6 mmol) of lithium aluminum hydride were added, and it was refluxed at 75° C. for one hour under a nitrogen atmosphere. After that, 1.5 mL of water, 1.5 mL of a 15% aqueous sodium hydroxide solution, 4.6 mL of water were sequentially added while cooling with ice to stop a reaction. Solids in a reaction solution were removed by filtration, the filtrate was condensed to obtain an unrefined compound (d). The unrefined compound (d) was directly used for a next reaction.

(Production of Compound (f1-1))

To a flask, the obtained compound (d) and 40 mL of acetic acid, 40 mL of distilled water were added, and a 0.5 M aqueous sodium nitrite solution was dropped for 15 minutes under cooling with ice. After a reaction was carried out for one hour under cooling with ice, 100 mL of hexane was added thereto, the temperature was returned to room temperature, and an organic layer was collected. To a water layer, 70 mL of hexane was added to be extracted, the resultant was washed with a saturated aqueous sodium hydrogen carbonate solution together with the collected organic layer, dried with anhydrous sodium sulfate, and then a solvent was removed under reduced pressure. The resultant was refined by column chromatography using hexane/ethyl acetate (4:1, volume ratio) as a developing solution to obtain a compound (f1-1) (4.0 g, 11.0 mmol). A yield from the compound (c) was 68%.

(Production of NIR Dye (A1-19))

To a flask equipped with a reflux device and a diversion device, 4.0 g (11.0 mmol) of the compound (f1-1), 0.8 g (6.6 mmol) of squaric acid, 40 mL of toluene, and 25 mL of 1-butanol were added, and it was refluxed at 125° C. for 12 hours while stirring. After a reaction was finished, a solvent was removed under reduced pressure, and then refinement was performed by column chromatography using toluene/dichloromethane (3:2, volume ratio) as a developing solution, to thereby obtain a NIR dye (A1-19) (4.0 g, 10.0 mmol, yield: 91%).

[Production of NIR Dye (A2-1)]

As shown in the following, a NIR dye (A2-1) was produced as same as the case of the NIR dye (A1-1) except that a compound (c2) (where $R^3$ and $R^4$ were each a hydrogen atom) was produced instead of the compound (c) from the compound (b).

[Chemical Formula 18]

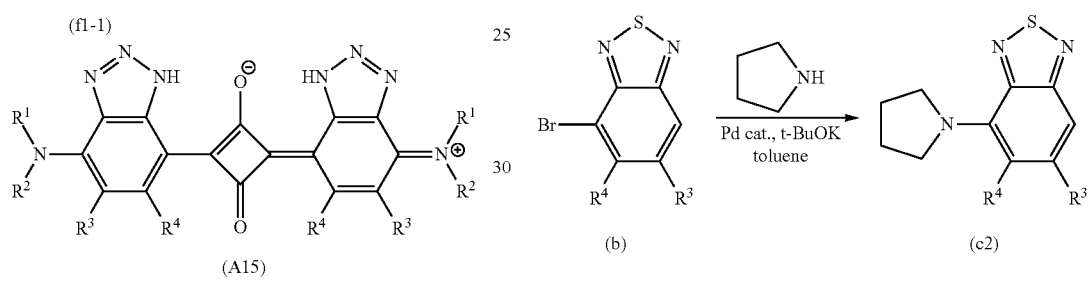

(Production of Compound (c2))

To a flask equipped with a reflux device, 2.7 g (24.2 mmol) of t-butoxypotassium, 0.3 g (0.4 mmol) of a Pd catalyst (PEPPSI™-IPr), 70 mL of toluene, 4.3 g (20.2 mmol) of the compound (b), and 1.8 mL (22.2 mmol) of pyrrolidine were added, and it was refluxed at 120° C. for three hours under a nitrogen atmosphere. After a reaction was finished, solids in a reaction solution were removed by filtration, the filtrate was condensed, and then refinement was performed by column chromatography using dichloromethane as a developing solution, to thereby obtain a compound (c2) (2.9 g, 14 mmol, yield: 70%).

[Production of NIR Dye (A2-2)]

A NIR dye (A2-2) was produced as same as the case of the NIR dye (A2-1) except that under existence of sodium hydrogen sulfite instead of the formic acid, a reaction was carried out with heptanal while using N,N-dimethylacetamide (DMAc) as a solvent.

[Production of NIR Dye (A1-6)]

The following concretely explains a production example of a NIR dye (A1-6) by using Scheme (F5) illustrated below. In the following explanation, although a description is not made on $R^1$ to $R^5$ in raw material components and intermediate products, $R^1$ and $R^2$ are each a 2-ethylhexyl group, and $R^3$ to $R^5$ are each a hydrogen atom.

In the production of the NIR dye (A1-6), a compound (h) in Scheme (F5), that is 5-bromoisoquinoline, was obtained from Tokyo Chemical Industry Co., Ltd., and used as a starting material.

[Chemical Formula 19]

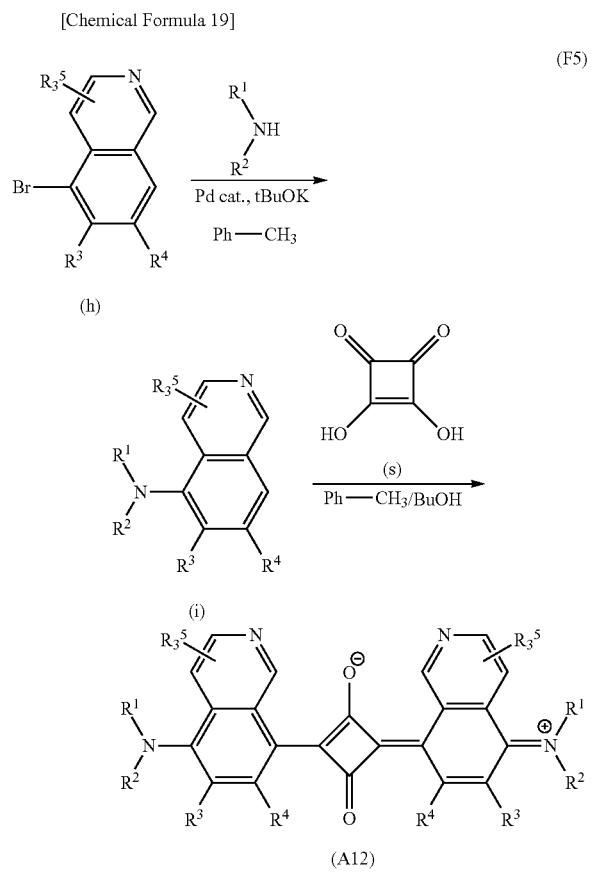

(Production of Compound (i))

To a flask, 2.08 g (10 mmol) of 5-bromoisoquinoline, 10 mL of toluene, 2.65 g (11 mmol) of bis(2-ethylhexyl)amine, 0.13 g (0.2 mmol) of a Pd catalyst (PEPPSI™-IPr), and 1.34 g (12 mmol) of t-butoxypotassium were added, and a reaction was carried out at 120° C. for five hours. After the reaction was finished, solids in a reaction solution were removed by filtration, the filtrate was condensed, and then refinement was performed by a column chromatography method. As a result, a compound (i) (1.36 g, 3.7 mmol, yield: 37%) was obtained.

(Production of NIR Dye (A1-6))

To a flask, 1.36 g (3.7 mmol) of the compound (i), 0.43 g (2.2 mmol) of squaric acid, 12 mL of toluene, and 4 mL of butanol were added, and it was heated and stirred at 120° C. for eight hours. After a reaction was finished, a solvent was removed by using an evaporator, and then the resultant was washed with ethyl acetate, and refinement was performed by a column chromatography method. As a result, a NIR dye (A1-6) (0.16 g, 0.2 mmol, yield: 11%) was obtained.

[Production of NIR Dye (A1-7)]

A NIR dye (A1-7) was produced as same as the case of the NIR dye (A1-6) except that 7-bromobenzothiophene was used instead of 5-bromoisoquinoline as a starting material. Note that 7-bromobenzothiophene was produced by a method described in the specification of International Publication Pamphlet No. 2013/159862.

[Production of NIR Dye (A2-3)]

A NIR dye (A2-3) was produced as same as the production of the NIR dye (A1-6) except that pyrrolidine was used instead of bis(2-ethylhexyl)amine.

[Production of NIR Dye (A2-4)]

A NIR dye (A2-4) was produced as same as the production of the NIR dye (A1-7) except that pyrrolidine was used instead of bis(2-ethylhexyl)amine.

[Production of NIR Dye (A2-5)]

A NIR dye (A2-5) was produced as same as the production of the NIR dye (A2-3) except that 4-bromobenzisothiazol was used instead of 5-bromoisoquinoline as a starting material. Note that 4-bromobenzisothiazol was produced by a method described in the specification of International Publication Pamphlet No. 2011/100502.

[Production of NIR Dye (A2-6)]

A NIR dye (A2-6) was produced as same as the production of the NIR dye (A2-3) except that a compound (m) illustrated below was used instead of 5-bromoisoquinoline as a starting material.

The following explains a production example of the compound (m) by using Scheme (F6) illustrated below.

In the production of the compound (m), a compound (j) was obtained from Tokyo Chemical Industry Co., Ltd. and used as a starting material.

[Chemical Formula 20]

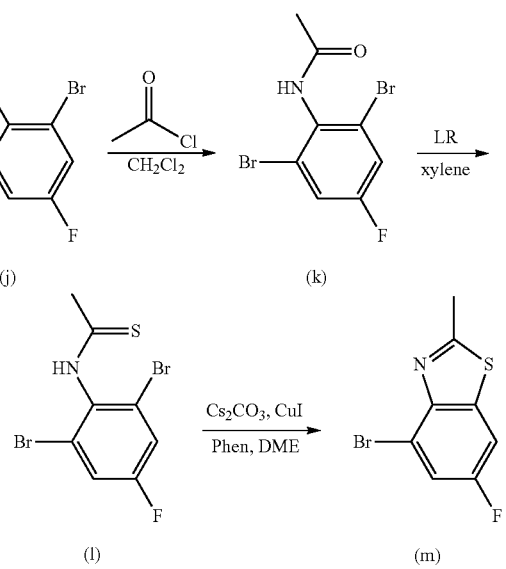

(Production of Compound (k))

To a flask, 1.07 g (4.0 mmol) of the compound (j), 15 mL of dichloromethane, and 0.47 g (6.0 mmol) of acetyl chloride were added, and it was stirred at room temperature for one hour. After a reaction was finished, a solvent was removed by using an evaporator, and then refinement was performed by a column chromatography method. As a result, a compound (k) (1.2 g, 3.9 mmol, yield: 98%) was obtained.

(Production of Compound (l))

To a flask, 1.2 g (3.9 mmol) of the compound (k), 15 mL of xylene, and 1.6 g (3.9 mmol) of Lawesson's reagent (LR) were added, and it was stirred at 110° C. for 12 hours. After a reaction was finished, a solvent was removed by using an evaporator from a filtered filtrate, and then refinement was performed by a column chromatography method. As a result, a compound (l) (0.84 g, 2.6 mmol, yield: 66%) was obtained.

(Production of Compound (m))

To a flask, 0.4 g (1.3 mmol) of the compound (1), 15 mL of dimethoxyethane (DME), 0.7 g (1.95 mmol) of cesium carbonate, 0.014 g (0.06 mmol) of copper iodide, and 0.028 g (0.12 mmol) of 1,10-phenanthroline (Phen) were added, and it was stirred at 70° C. for 24 hours. After a reaction was finished, solids in a reaction solution were removed by filtration, the filtrate was condensed, and then refinement was performed by a column chromatography method. As a result, a compound (m) (0.1 g, 0.4 mmol, yield: 31%) was obtained.

[Production of NIR Dye (A1-8)]

A production example of a NIR dye (A1-8) was concretely explained by using Scheme (F7) illustrated below. In the following explanation, although a description is not made on $R^1$ and $R^2$ in raw material components and (intermediate) products, both are each the group (2a).

In the production of the NIR dye (A1-8), a compound (t), that is 2,6-difluorobenzaldehyde, was obtained from Tokyo Chemical Industry Co., Ltd. and used as a starting material.

[Chemical Formula 21]

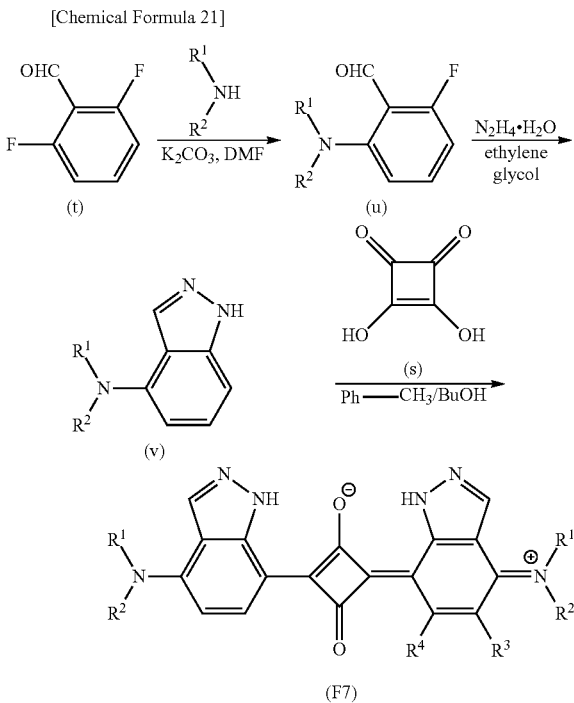

(F7)

(Production of Compound (u))

To a flask, 8.3 g (52.8 mmol) of diisoamylamine, 10 mL of N,N-dimethylfolmamide (DMF), and 7.3 g (52.8 mmol) of potassium carbonate were added, it was stirred at room temperature, and further 5 g (35.1 mmol) of 2,6-difluorobenzaldehyde was added. An oil bath was used to set a reaction temperature at 80° C., and the resultant was stirred for three days. The reaction temperature was returned to room temperature, 30 mL of water was added and stirred, and 50 mL each of ethyl acetate and hexane were added. An organic layer was dried with anhydrous magnesium sulfate, a solvent was removed under reduced pressure, and then refinement was performed by column chromatography using hexane/ethyl acetate (100:5, volume ratio) as a developing solution. As a result, a compound (u) (9.8 g, 35.2 mmol, yield: 100%) was obtained.

(Production of Compound (v))

To a flask, 9.8 g (35.2 mmol) of the compound (u), 25 mL of ethylene glycol, and 3.9 g (77.8 mmol) of hydrazine monohydrate were added, and it was stirred at 165° C. for 18 hours. A reaction temperature was returned to room temperature, 30 mL of water, and 30 mL of methylene chloride were added and stirred. An organic layer was dried with anhydrous magnesium sulfate, a solvent was removed under reduced pressure, and then refinement was performed by column chromatography using hexane/ethyl acetate (9:1, volume ratio) as a developing solution. As a result, a compound (v) (1.2 g, 4.5 mmol, yield: 13%) was obtained.

(Production of NIR Dye (A1-8))

To a flask equipped with a reflux device and a diversion device, 1.2 g (4.5 mmol) of the compound (v), 0.25 g (2.3 mmol) of squaric acid, 25 mL of toluene, and 25 mL of 1-butanol were added, and it was refluxed at 110° C. for 12 hours while stirring. After a reaction was finished, a solvent was removed under reduced pressure, and then obtained solids were washed with methylene chloride, methanol. As a result, a NIR dye (A1-8) (1.0 g, 1.6 mmol, yield: 72%) was obtained.

[Production of NIR Dye (A1-9)]

A NIR dye (A1-9) was produced as same as the case of the NIR dye (A1-8) except that the compound (u) (where $R^1$ and $R^2$ were each the group (1a)) was produced by using di(2-ethylhexyl)amine instead of diisoamylamine, and the refinement method of a NIR dye was changed to a silica gel column chromatography in a process producing the compound (u) from the compound (t).

Concretely, the compound (u) was produced from the compound (t) as follows.

To a flask, 12.7 g (52.8 mmol) of di(2-ethylhexyl)amine, 10 mL of N,N-dimethylfolmamide (DMF), and 7.3 g (52.8 mmol) of potassium carbonate were added, it was stirred at room temperature, and further 5 g (35.1 mmol) of 2,6-difluorobenzaldehyde was added. An oil bath was used to set a reaction temperature at 80° C., and the resultant was stirred for three days. The reaction temperature was returned to room temperature, 30 mL of water was added and stirred, and 50 mL each of ethyl acetate and hexane were added. An organic layer was dried with anhydrous magnesium sulfate, a solvent was removed under reduced pressure, and then refinement was performed by column chromatography using hexane/ethyl acetate (9:1, volume ratio) as a developing solution, to thereby obtain a compound (u) (8.8 g, 24.2 mmol, yield: 69%).

[Production of NIR Dye (A1-10)]

A NIR dye (A1-10) was produced as same as the case of the NIR dye (A1-8) except that the compound (u) (where $R^1$ and $R^2$ were each the group (3a)) was produced by using diisobutylamine instead of diisoamylamine, and a refinement method of a NIR dye was changed to a silica gel column chromatography in the process of producing the compound (u) from the compound (t).

Concretely, the compound (u) was produced from the compound (t) as follows.

To a flask, 6.8 g (52.8 mmol) of diisobutylamine, 10 mL of N,N-dimethylfolmamide (DMF), and 7.3 g (52.8 mmol) of potassium carbonate were added, it was stirred at room temperature, and further 5 g (35.1 mmol) of 2,6-difluorobenzaldehyde was added. An oil bath was used to set a reaction temperature at 80° C., and the resultant was stirred for three days. The reaction temperature was returned to room temperature, 30 mL of water was added and stirred, and 50 mL each of ethyl acetate and hexane were added. An organic layer was dried with anhydrous magnesium sulfate, a solvent was removed under reduced pressure, and then refinement was performed by column chromatography using hexane/ethyl acetate (9:1, volume ratio) as a developing solution, to thereby obtain the compound (u) (8.8 g, 33.9 mmol, yield: 96%).

[Production of NIR Dye (A1-11)]

A NIR dye (A1-11) was produced as same as the case of the NIR dye (A1-8) except that the compound (u) (where $R^1$ and $R^2$ were each the group (4a)) was produced by using bis(2-ethoxyethyl)amine instead of diisoamylamine, and a refinement method of a NIR dye was changed to a silica gel column chromatography in the process of producing the compound (u) from the compound (t).

Concretely, the compound (u) was produced from the compound (t) as follows.

To a flask, 8.5 g (52.8 mmol) of bis(2-ethoxyethyl)amine, 10 mL of N,N-dimethylfolmamide (DMF), and 7.3 g (52.8 mmol) of potassium carbonate were added, it was stirred at room temperature, and further 5 g (35.1 mmol) of 2,6-difluorobenzaldehyde was added. An oil bath was used to set a reaction temperature at 80° C., and the resultant was stirred for 15 hours. The reaction temperature was returned to room temperature, 30 mL of water was added and stirred, and 50 mL each of ethyl acetate and hexane were added. An organic layer was dried with anhydrous magnesium sulfate, a solvent was removed under reduced pressure, and then refinement was performed by column chromatography using hexane/ethyl acetate (8:2, volume ratio) as a developing solution, to thereby obtain the compound (u) (8.4 g, 29.9 mmol, yield: 84%).

[Production of NIR Dye (A1-12)]

A NIR dye (A1-12) was produced as same as the case of the NIR dye (A1-8) except that the compound (u) (where $R^1$ and $R^2$ were each the group (5a)) was produced by using bis(2-(2-ethylhexyloxy)ethyl)amine instead of diisoamylamine, and a refinement method of a NIR dye was changed to a silica gel column chromatography in the process of producing the compound (u) from the compound (t).

Concretely, the compound (u) was produced from the compound (t) as described below.

To a flask, 6.9 g (19.9 mmol) of bis(2-(2-ethylhexyloxy)ethyl)amine, 55 mL of N,N-dimethylfolmamide (DMF), and 3.9 g (28.4 mmol) of potassium carbonate were added, it was stirred at room temperature, and further 2.7 g (18.9 mmol) of 2,6-difluorobenzaldehyde was added. An oil bath was used to set a reaction temperature at 80° C., and the resultant was stirred for two days. The reaction temperature was returned to room temperature, 30 mL of water was added and stirred, and 50 mL each of ethyl acetate and hexane were added. An organic layer was dried with anhydrous magnesium sulfate, a solvent was removed under reduced pressure, and then refinement was performed by a column chromatography method using hexane/ethyl acetate (9:1, volume ratio) as a developing solution, to thereby obtain the compound (u) (7.7 g, 17.1 mmol, yield: 90%).

Here, a production example of bis(2-(2-ethylhexyloxy)ethyl)amine used for the production of the dye (A1-12) is explained by using Scheme (F8) illustrated below. A compound (w), that is 2-(2-ethylhexyloxy)ethyl alcohol, obtained from Kanto Chemical Co., Inc. was used as a starting material. Note that bis(2-(2-ethylhexyloxy)ethyl)amine produced similarly was used in the production of the dye (A1-16).

[Chemical Formula 22]

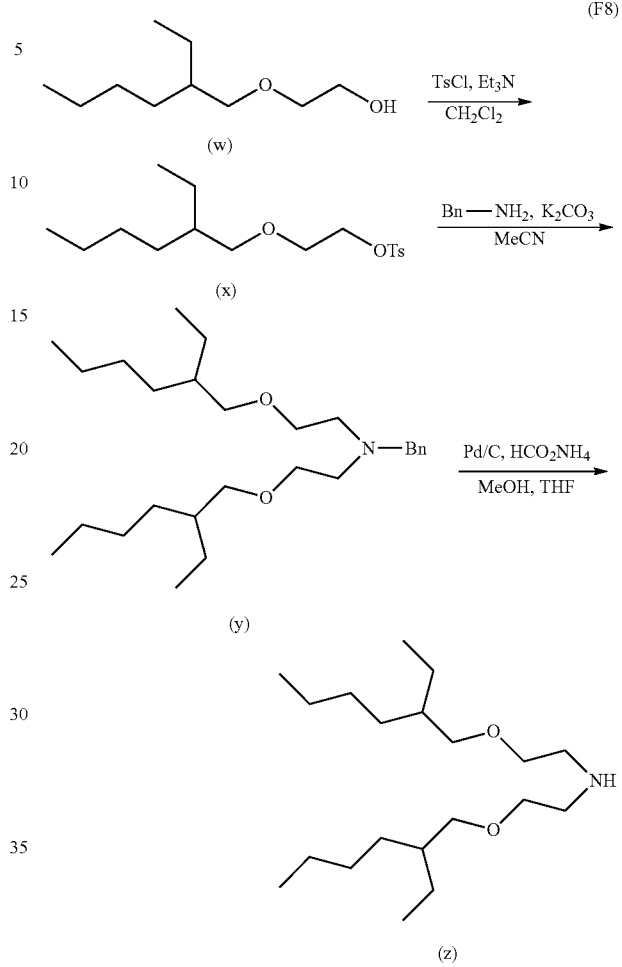

In Scheme (F8), Ts represents a paratoluenesulfonyl group, and Bn represents a benzyl group.

(Production of Compound (x))

To a flask, 10.0 g (57.4 mmol) of the compound (w) and 150 mL of methylene chloride were added, and it was stirred in an ice bath. After adding 8.7 g (86.1 mmol) of triethylamine, 11.5 g (60.2 mmol) of paratoluenesulfonicacid chloride, the temperature was returned to room temperature, stirred for two hours, then 150 mL of water was added and stirred. An organic layer was dried with anhydrous magnesium sulfate, a solvent was removed under reduced pressure, and then refinement was performed by column chromatography using hexane/ethyl acetate (9:1, volume ratio) as a developing solution, to thereby obtain a compound (x) (17.1 g, 52.1 mmol, yield: 91%).

(Production of Compound (y))

To a flask, 2.68 g (25.0 mmol) of benzylamine, 20 mL of acetonitrile, and 20.5 g (14.9 mmol) of potassium carbonate were added, and it was stirred in an ice bath. After that, 17.1 g (52.1 mmol) of the compound (x) dissolved in 30 mL of acetonitrile was added. The ice bath was changed to an oil bath, and the resultant was refluxed and stirred at 90° C. for two days. After that, potassium carbonate was filtered, and the filtrate was removed under reduced pressure, and refinement was performed by column chromatography using hexane/ethyl acetate (100:3, volume ratio) as a developing solution. As a result, a compound (y) (8.7 g, 20.7 mmol, yield: 82%) was obtained.

(Production of Compound (z))

To a flask, 8.7 g (20.7 mmol) of the compound (y) and 40 mL of tetrahydrofuran (THF) were added, and it was stirred in an ice bath. After adding 2.7 g of 10% palladiumcarbon, 120 mL of methanol was added, 18.3 g (290 mmol) of ammonium formate was added, and the resultant was stirred at room temperature for 12 hours. Palladiumcarbon and insoluble ammonium formate were removed by filtration under reduced pressure, the filtrate was condensed under reduced pressure, and liquid separation was performed with methylene chloride and water. An obtained organic layer was dried with anhydrous magnesium sulfate, a solvent was distilled off, and then refinement was performed by column chromatography using methylene chloride/methanol (100:3, volume ratio) as a developing solution. As a result, a compound (z), that is bis(2-(2-ethylhexyloxy)ethyl)amine, (6.6 g, 19.9 mmol, yield: 96%) was obtained.

[Production of NIR Dye (A3-1)]

The following concretely explains a production example of a NIR dye (A3-1) by using Scheme (F9).

In the production of the dye (A3-1), a compound (n) in Scheme (F9) was produced by a method described in the specification of International Publication Pamphlet No. 2014/088063 and used as a starting material.

[Chemical Formula 23]

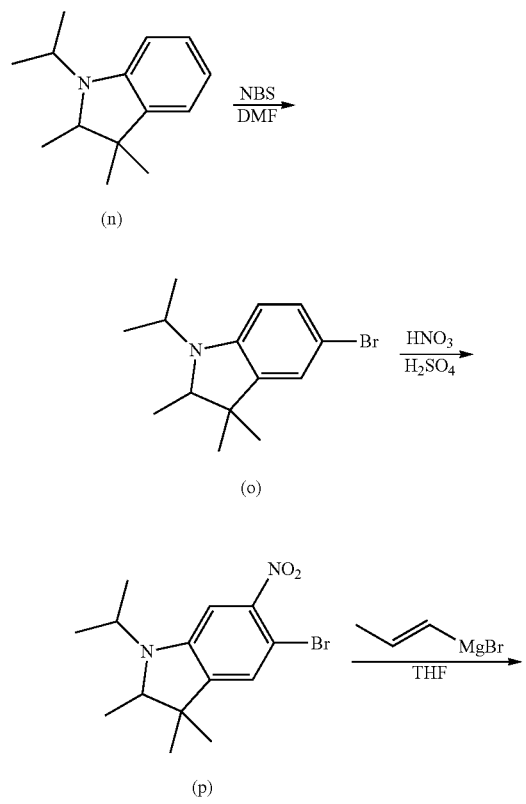

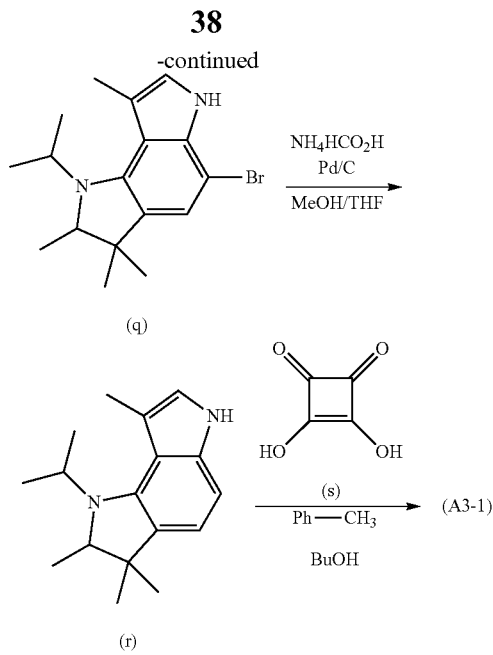

(Production of Compound (o))

To a flask, 10.0 g (49.2 mmol) of the compound (n) and 200 mL of N,N-dimethylfolmamide (DMF) were added. After it was cooled to 0° C., 8.8 g (49.2 mmol) of N-bromosuccinimide (NBS) dissolved in 50 mL of DMF was dropped, and stirred at 0° C. for one hour. After 100 mL of water was added to stop a reaction, DMF was removed under reduced pressure, and 100 mL of ethyl acetate was added. An organic layer was dried with anhydrous sodium sulfate, a solvent was removed under reduced pressure, to thereby obtain a compound (o). The unrefined compound (o) was directly used for a next reaction.

(Production of Compound (p))

To a flask, 13.6 g (48.3 mmol) of the compound (o) was added, 48.7 g (496.5 mmol) of concentrated sulfuric acid was quickly dropped at 0° C., and then it was stirred for 30 minutes. After that, mixed acid made up of 6.1 g (58.0 mmol) of 60% concentrated nitric acid and 17.8 g (181.1 mmol) of concentrated sulfuric acid was dropped under an ice bath, then the temperature was returned to room temperature, and the resultant was stirred for two hours. After a reaction was finished, a reaction solution was dropped while adding ice blocks at appropriate timing to 100 mL of ice water, and then a 40% aqueous sodium hydroxide solution was dropped. After it was verified by a pH test paper that the solution becomes basic, 500 mL of ethyl acetate was added. An organic layer was dried with anhydrous sodium sulfate, a solvent was removed tinder reduced pressure, and then, refinement was performed by column chromatography using hexane/ethyl acetate (9:1, volume ratio) as a developing solution to thereby obtain a compound (p) (14.7 g, 45 mmol). A yield from the compound (n) was 92%.

(Production of Compound (q))

To a flask, 5.5 g (16.7 mmol) of the compound (p) and 80 mL of THF were added. Under a nitrogen atmosphere, 100 mL (50 mmol) of 1-propenylmagnesium bromide (0.5 M, THF solution) was dropped at −40° C., and it was stirred for one hour. After adding 150 mL of an aqueous ammonium chloride solution to stop a reaction, the temperature was returned to room temperature, and 150 mL of ethyl acetate was added. An organic layer was washed with a saturated salt solution, dried with anhydrous sodium sulfate, a solvent was removed under reduced pressure, to thereby obtain a compound (q). The unrefined compound (q) was directly used for a next reaction.

(Production of Compound (r))

To a flask, the compound (q) and 40 mL of THF were added. After that, 1.1 g of palladium carbon (Pd/C), 120 mL of methanol, and 5.3 g (83.4 mmol) of ammonium formate were added thereto at 0° C., the temperature was returned to room temperature, and the resultant was stirred for one hour. After a reaction was finished, 100 mL of water was added, solids were removed by filtration, and methanol and THF in the filtrate were removed under reduced pressure. A hundred mL of ethyl acetate was added thereto, an organic layer was collected and dried with anhydrous sodium sulfate, and then a solvent was removed under reduced pressure to obtain a crude compound (r). This was refined by column chromatography using hexane/ethyl acetate (9:1, volume ratio) as a developing solution to thereby obtain a compound (r) (1.4 g, 5.4 mmol). A yield from the compound (p) was 32%.

(Production of NIR Dye (A3-1))

To a flask equipped with a reflux device and a diversion device, 1.4 g (5.4 mmol) of the compound (r), 0.4 g (3.2 mmol) of squaric acid, 25 mL of toluene, and 25 mL of 1-butanol were added, and it was refluxed at 125° C. for 12 hours while stirring. After a reaction was finished, a solvent was removed under reduced pressure, and then refinement was performed by column chromatography using toluene/dichloromethane (3:2, volume ratio) as a developing solution to thereby obtain a NIR dye (A3-1) (1.0 g, 1.7 mmol, yield: 63%).

[Production of NIR Dye (A4-1)]

The following concretely describes a production example of a NIR dye (A4-1) by using Scheme (F10). In Scheme (F10), Py represents a pyridyl group.

In production of a NIR dye (A4-2), a compound (x1) in Scheme (F10), that is indole-6-carboxyaldehyde, was obtained from Tokyo Chemical Industry Co., Ltd., and used as a starting material.

[Chemical Formula 24]

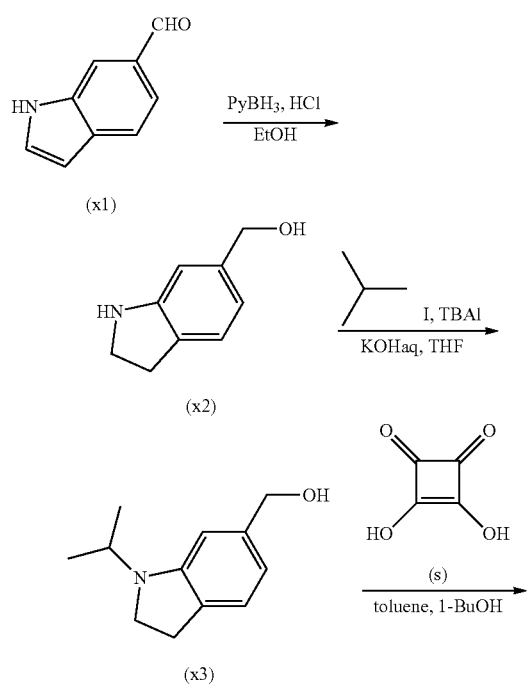

(F10)

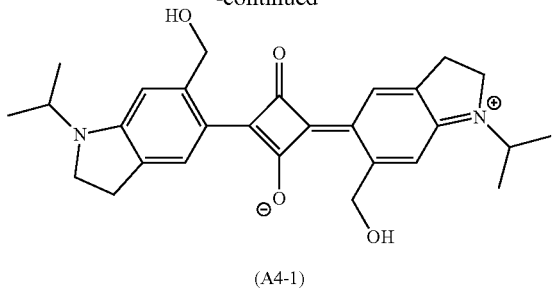

(A4-1)

(Production of Compound (x2))

Under a nitrogen atmosphere, to a flask, 1.0 g (6.89 mmol) of the compound (x1), 20 mL of ethanol, and 3.84 g (41.33 mmol) of pyridineborane were added, 11 mL of a 6M aqueous hydrochloric acid solution was dropped under ice cooling, and it was stirred at 0° C. for three hours, and at room temperature for 18 hours. After that, 50 mL of a saturated aqueous sodium hydrogen carbonate solution was added under ice cooling, and extraction was performed with 100 mL of ethyl acetate. An obtained organic layer was dried with anhydrous sodium sulfate, a solvent was removed by using an evaporator, and then refinement was performed by column chromatography using hexane/ethyl acetate (3:2, volume ratio) as a developing solution, to thereby obtain a compound (x2) (0.35 g, 2.24 mmol). A yield from the compound (x1) was 34%.

(Production of Compound (x3))

To a flask, 0.35 g (2.24 mmol) of the compound (x2), 85 mg (0.23 mmol) of tetrabutylammonium iodide, 10 mL of a 33 weight % aqueous potassium hydroxide solution, and 10 mL of tetrahydrofuran were added, 1.99 g of 2-iodopropane was dropped, and it was stirred at 80° C. for 15 hours. After that, 100 mL of water was added, a major part of tetrahydrofuran was removed by using an evaporator, and then extraction was performed with 100 mL of ethyl acetate. An obtained organic layer was dried with anhydrous sodium sulfate, a solvent was removed by using an evaporator, and then refinement was performed by column chromatography using hexane/ethyl acetate (1:1, volume ratio) as a developing solution, to thereby obtain a compound (x3) (0.39 g, 1.95 mmol). A yield from the compound (x2) was 87%.

(Production of Compound (A4-1))

To a flask equipped with a diversion device, 0.45 g (2.51 mmol) of the compound (x3), 10 mL of toluene, 10 mL of 1-butanol, and 0.14 g (1.25 mmol) of squaric acid were added, and it was stirred for three hours under an azeotrope heat refluxing condition. After a reaction was finished, a reaction solvent was removed by using an evaporator, and then refinement was performed by column chromatography using hexane/ethyl acetate (1:2, volume ratio) as a developing solution, to thereby obtain a compound (A4-1) (0.12 g, 0.39 mmol). A yield from the compound (x3) was 20%.

[Production of NIR Dye (A4-2)]

The following concretely describes a production example of a NIR dye (A4-2) by using Scheme (F11).

In production of a NIR dye (A4-2), the compound (x3) produced from indole-7-carboxyaldehyde (the compound (x1) in Scheme (F10)) was used as a starting material as same as the case of the NIR dye (A4-1).

41

[Chemical Formula 25]

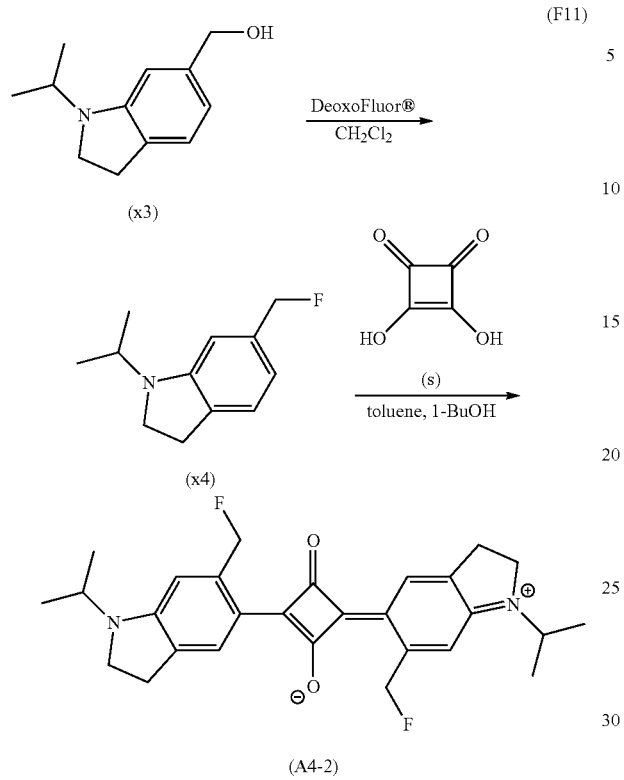

42

(x1) in Scheme (F10)) was used as a starting material as same as the case of the NIR dye (A4-1).

[Chemical Formula 26]

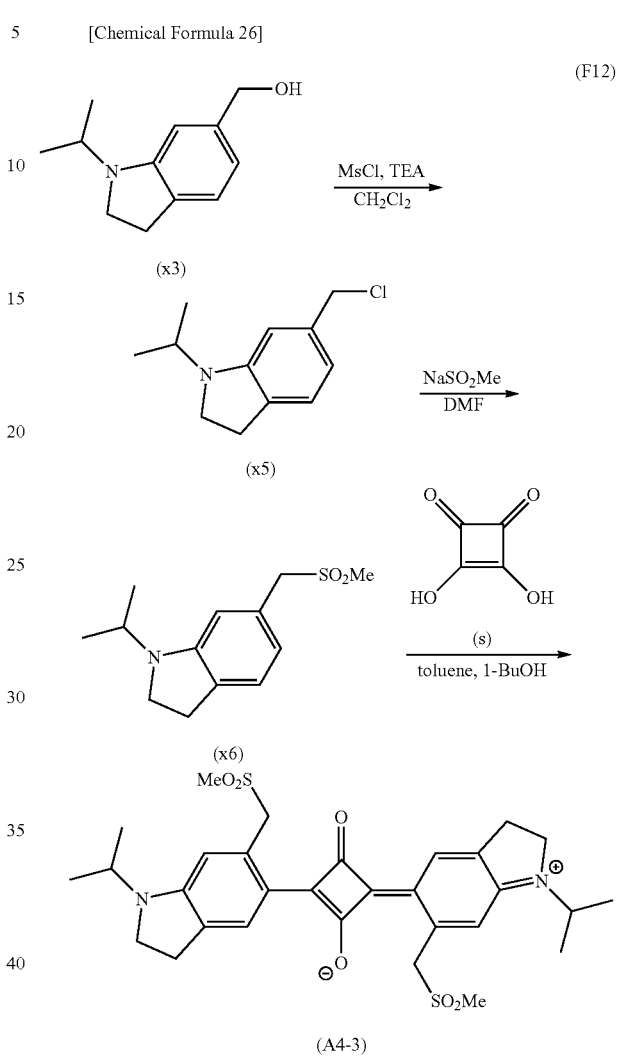

(Production of Compound (x4))

Under a nitrogen atmosphere, to a flask, 3.69 g (16.68 mmol) of DeoxoFluor (registered trademark) (manufactured by Sigma-Aldrich Co., LLC.) and 15 mL of dichloromethane were added, 2.90 g (15.16 mmol) of the compound (x3) dissolved in 15 mL of dichloromethane was dropped, and it was stirred at the same temperature for one hour. After that, 30 mL of a saturated aqueous sodium hydrogen carbonate solution was added under ice cooling, and extraction was performed with 100 mL of dichloromethane. An obtained organic layer was dried with anhydrous sodium sulfate, a solvent was removed by using an evaporator, and then refinement was performed by column chromatography using hexane/ethyl acetate (2:1, volume ratio) as a developing solution, to thereby obtain a compound (x4) (0.21 g, 1.06 mmol). A yield from the compound (x3) was 7%.

(Production of Compound (A4-2))

To a flask equipped with a diversion device, 0.20 g (1.03 mmol) of the compound (x4), 10 mL of toluene, 10 mL of 1-butanol, and 0.06 g (0.52 mmol) of squaric acid were added, and it was stirred for three hours under an azeotrope heat refluxing condition. After a reaction was finished, a reaction solvent was removed by using an evaporator, and then refinement was performed by column chromatography using hexane/ethyl acetate (1:2, volume ratio) as a developing solution, to thereby obtain a compound (A4-2) (0.05 g, 0.10 mmol). A yield from the compound (x4) was 10%.

[Production of NIR Dye (A4-3)]

The following concretely describes a production example of a NIR dye (A4-3) by using Scheme (F12).

In production of a NIR dye (A4-3), the compound (x3) produced from indole-7-carboxyaldehyde (the compound (Production of Compound (x5))

Under a nitrogen atmosphere, to a flask, 2.10 g (10.98 mmol) of the compound (x3), 30 mL of dichloromethane, 1.22 g (12.08 mmol) of triethylamine (TEA), 2.30 g (12.08 mmol) of methanesulfonyl chloride (MsCl) were added under ice cooling, it was stirred at the same temperature for five hours, and then stirred at room temperature for 15 hours. After that, extraction was performed with 100 mL of dichloromethane under ice cooling. An obtained organic layer was dried with anhydrous sodium sulfate, a solvent was removed by using an evaporator, and then refinement was performed by column chromatography using hexane/ethyl acetate (2:1, volume ratio) as a developing solution, to thereby obtain a compound (x5) (1.04 g, 4.94 mmol). A yield from the compound (x3) was 45%.

(Production of Compound (x6))

To a flask, 0.56 g (2.67 mmol) of the compound (x5), 8 mL of dimethylfolmamide (DMF), and 0.82 g (8.01 mmol) of methanesulfonic acid sodium were added, and it was stirred at 60° C. for two hours. After that, 30 mL of water was added, and extraction was performed with 100 mL of ethyl acetate. An obtained organic layer was dried with anhydrous sodium sulfate, a solvent was removed by using an evaporator, and then refinement was performed by column chromatography using hexane/ethyl acetate (1:1, volume ratio) as a developing solution, to thereby obtain a compound (x6) (0.48 g, 1.90 mmol). A yield from the compound (x5) was 71%.

(Production of Compound (A4-3))

To a flask equipped with a diversion device, 0.48 g (1.90 mmol) of the compound (x6), 10 mL of toluene, 10 mL of 1-butanol, and 0.11 g (0.95 mmol) of squaric acid were added, and it was stirred for three hours under an azeotrope heat refluxing condition. After a reaction was finished, a reaction solvent was removed by using an evaporator, and then a residue was washed with dichloromethane and hexane, to thereby obtain a compound (A4-3) (0.09 g, 0.32 mmol). A yield from the compound (x6) was 17%.

Note that NIR dyes (C1), (C3) used for comparison were each produced by the method described in the specification of International Publication Pamphlet No. 2014/088063, Japanese Laid-open Patent Publication No. 2014-059550, and S2098 (product name, manufactured by FEWChemicals Co., Ltd) was used as a NIR dye (C2).

<Evaluation of NIR Dye>

(1) Absorption Characteristic of Dye in Dichloromethane

The obtained NIR dyes were each dissolved in dichloromethane, and an ultraviolet-visible spectrophotometer (manufactured by Shimadzu Corporation, UV-3100) was used to measure each spectral transmittance curve, from which a maximum absorption constant $\varepsilon_A$ at a wavelength of 430 to 550 nm, a maximum absorption constant $\varepsilon_B$ (normalized by=1) at a wavelength of 680 to 770 nm, and a ratio ($\varepsilon_B/\varepsilon_A$) of them were calculated. Note that all of the absorption constants $\varepsilon_B$ accorded with a maximum absorption constant at a wavelength of 670 nm or more. Results thereof are listed in Table 3. In Table 3, an average transmittance of light with a wavelength of 430 to 460 nm ($T_{AVG.(430-460)}$), and a maximum value ($\Delta T/\Delta\lambda_{(max)}$) of a slope ($\Delta T/\Delta\lambda$) of a spectral transmittance curve between a wavelength $\lambda_{80}$ with which a transmittance on a shorter wavelength side than the maximum absorption wavelength $\lambda_m$ax becomes 80% and a wavelength $\lambda_{10}$ with which a transmittance becomes 10%, a minimum value ($T_{min\ (410-460)}$) of a transmittance of light with a wavelength of 410 to 460 nm ($T_{(410-460)}$), a longest wavelength $\lambda_{97}$ when a transmittance with respect to light with a wavelength of 460 nm or less becomes 97%, and a difference ($\lambda_{max}-\lambda_{80}$) between a wavelength $\lambda_{80}$ when a transmittance on a shorter wavelength side than the maximum absorption wavelength $\lambda_{max}$ becomes 80% and the maximum absorption wavelength $\lambda_{max}$ are respectively listed, when the maximum absorption wavelength of each dye is set to $\lambda_{max}$, and a transmittance at the maximum absorption wavelength $\lambda_{max}$ is set to 1%. Note that the slope ($\Delta T/\Delta\lambda$) is a value obtained based on an interval of $\Delta\lambda=1$ nm, and a maximum value of the slope ($\Delta T/\Delta\lambda$) shows a maximum value of an obtained plurality of slopes. Further, regarding the dyes (A1-1) to (A1-5), (A1-7) to (A1-19), (A4-1) to (A4-3), spectral transmittance curves when the transmittance at the maximum absorption wavelength $\lambda_{max}$ is set to 1% are illustrated in FIG. 2A to FIG. 2D.

TABLE 3

| Abbreviation of dye | $\lambda_{max}$ [nm] | $\varepsilon_A$ [M$^{-1}$cm$^{-1}$] | $\varepsilon_B/\varepsilon_A$ | $T_{Avg.(430-460)}$ [%] | $\Delta T/\Delta\lambda_{(max)}$ [%/nm] | $T_{min(410-460)}$ [nm] | $\lambda_{97}$ [nm] | $\lambda_{max} - \lambda_{80}$ [nm] |
|---|---|---|---|---|---|---|---|---|
| A1-1 | 714 | 0.0138 | 72.5 | 96.7 | −0.581 | 94.5 | 445 | 74 |
| A1-2 | 718 | 0.0104 | 96.2 | 96.1 | −0.541 | 95.3 | 454 | 76 |
| A1-3 | 713 | 0.0140 | 71.5 | 97.1 | −0.540 | 93.8 | 442 | 73 |
| A1-4 | 716 | 0.0107 | 93.5 | 96.3 | −0.567 | 95.2 | 453 | 77 |
| A1-5 | 717 | 0.0113 | 88.3 | 95.1 | −0.562 | 94.9 | 456 | 77 |
| A1-6 | 734 | 0.0139 | 71.9 | — | — | — | — | — |
| A1-7 | 724 | 0.0138 | 72.5 | 95.2 | −0.571 | 93.5 | 457 | 87 |
| A1-8 | 711 | 0.0069 | 145.9 | 99.3 | −0.549 | 94.2 | 430 | 70 |
| A1-9 | 720 | 0.0142 | 70.5 | 97.3 | −0.556 | 93.9 | 439 | 75 |
| A1-10 | 715 | 0.0081 | 123.3 | 99.5 | −0.513 | 93.0 | 431 | 71 |
| A1-11 | 708 | 0.0071 | 141.2 | 98.9 | −0.532 | 94.2 | 430 | 72 |
| A1-12 | 709 | 0.0059 | 170.0 | 99.6 | −0.542 | 94.3 | 429 | 71 |
| A1-13 | 705 | 0.0109 | 92.0 | 98.3 | −0.544 | 94.6 | 438 | 72 |
| A1-14 | 708 | 0.0130 | 77.1 | 97.1 | −0.583 | 94.4 | 442 | 73 |
| A1-15 | 699 | 0.0109 | 91.4 | 98.5 | −0.616 | 94.2 | 436 | 71 |
| A1-16 | 701 | 0.0109 | 92.1 | 98.6 | −0.565 | 94.3 | 436 | 71 |
| A1-17 | 705 | 0.0128 | 78.4 | 97.6 | −0.583 | 94.3 | 440 | 73 |
| A1-18 | 705 | 0.0125 | 80.2 | 97.8 | −0.567 | 94.3 | 439 | 73 |
| A1-19 | 708 | 0.0133 | 75.3 | 98.2 | −0.601 | 93.7 | 438 | 70 |
| A2-1 | 700 | 0.0118 | 84.7 | 98.0 | −0.515 | 94.3 | 437 | 72 |
| A2-2 | 705 | 0.0105 | 95.2 | 96.9 | −0.529 | 95.3 | 446 | 75 |
| A2-3 | 724 | 0.0148 | 67.6 | 97.8 | −0.357 | 92.9 | 463 | 80 |
| A2-4 | 713 | 0.0121 | 82.6 | 94.3 | −0.458 | 91.7 | 468 | 75 |
| A2-5 | 718 | 0.0135 | 74.1 | — | — | — | — | — |
| A2-6 | 721 | 0.0149 | 67.1 | — | — | — | — | — |
| A3-1 | 766 | 0.0120 | 83.3 | 95.4 | −0.475 | 94.4 | 479 | 103 |
| A4-1 | 688 | 0.0163 | 95.1 | 96.7 | −0.797 | 94.3 | 481 | 84 |
| A4-2 | 689 | 0.0115 | 86.8 | 96.5 | −0.804 | 94.1 | 472 | 86 |
| A4-3 | 701 | 0.0150 | 67.7 | 95.8 | −0.521 | 93.4 | 451 | 85 |
| C1 | 706 | 0.0163 | 61.4 | 94.4 | −0.423 | 88.0 | 458 | 77 |
| C2 | 668 | 0.0077 | 129.8 | 97.6 | −0.492 | 95.8 | 437 | 70 |
| C3 | 715 | 0.0239 | 41.9 | 92.7 | −0.565 | 89.5 | 545 | 82 |

As listed in Table 3, all of the dyes (A1-1) to (A1-5), (A1-7) to (A1-19), (A2-1) to (A2-4), (A3-1), and (A4-1) to (A4-3) satisfy the requirements (i-1) to (i-3). Meanwhile, the dyes (C1) to (C3) do not satisfy any of the requirements (i-1) to (i-3). In addition, the dyes (A1-1) to (A1-5), (A1-8) to (A1-19), (A2-1), (A2-2) further satisfy the requirements (i-4) to (i-7).

<Production of NIR Filter>

Example 1

Figure 3:
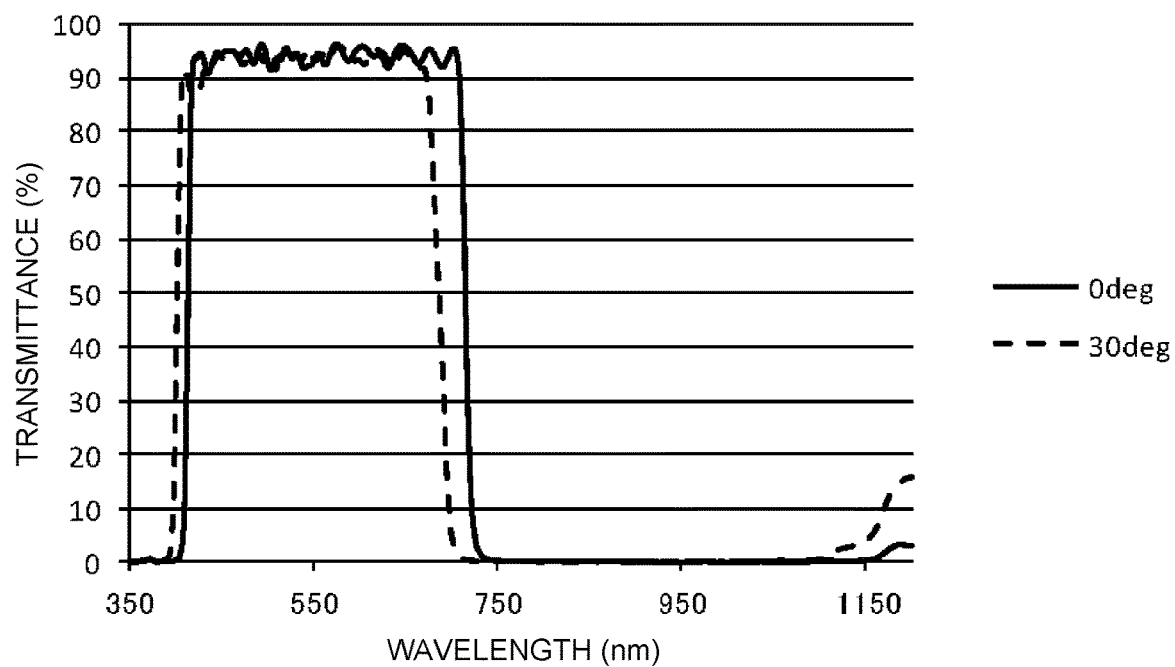
FIG. 3 is a view illustrating spectral transmittance curves of a reflection layer used for an optical filter of an example.

A reflection layer formed of 52 layers of dielectric multilayer films was formed by alternately stacking a $TiO_2$ film and an $SiO_2$ film on a glass (non-alkali glass; manufactured by Asahi Glass Co., Ltd., product name: AN100) substrate having a thickness of 0.3 mm by a vapor deposition method. Simulation was performed by using the number of stacks of the dielectric multilayer films, a film thickness of each of the $TiO_2$ film, and a film thickness of the $SiO_2$ film as parameters, to determine the reflection layer satisfying the requirements (ii-1) and (ii-2) in each of the spectral transmittance curves at the incident angles of 0° and 30°. FIG. 3 illustrates the spectral transmittance curves of the produced reflection layer.

Further, a coating liquid to form an absorption layer was prepared by adding cyclohexane, N-methylpyrrolidone, and the dye (A1-1) to a polyimide resin solution (manufactured by MITSUBISHI GAS CHEMICAL COMPANY, INC., Neopulim (registered trademark) C3450). Here, a ratio of the dye (A1-1) relative to 100 parts by mass of the polyimide resin was set to 10.9 parts by mass.

This coating liquid was applied onto an opposite surface to a reflection layer forming surface of the glass substrate where the reflection layer was formed by a spin coating method, and a solvent was heated and dried to form an absorption layer with a thickness of approximately 1.0 μm. After that, a $TiO_2$ film and an $SiO_2$ film were alternately stacked on a surface of the absorption layer by the vapor deposition method as same as the reflection layer to form an anti-reflection layer, and a NIR filter was obtained.

Examples 2 to 22

NIR filters were obtained as same as Example 1 except that the NIR dyes to be added to the coating liquid to form the absorption layer were changed as listed in Table 4 and Table 5.

<Evaluation of NIR Filter>

Figure 4A:
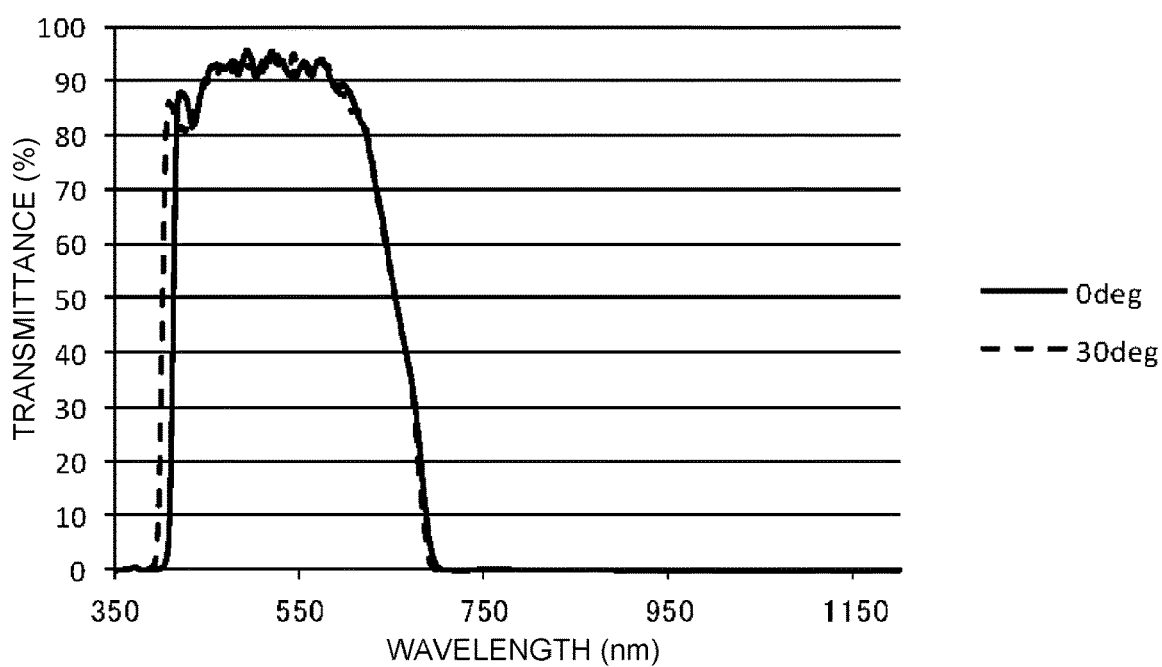
FIG. 4A is a view illustrating spectral transmittance curves of an optical filter obtained in an example.
Figure 4B:
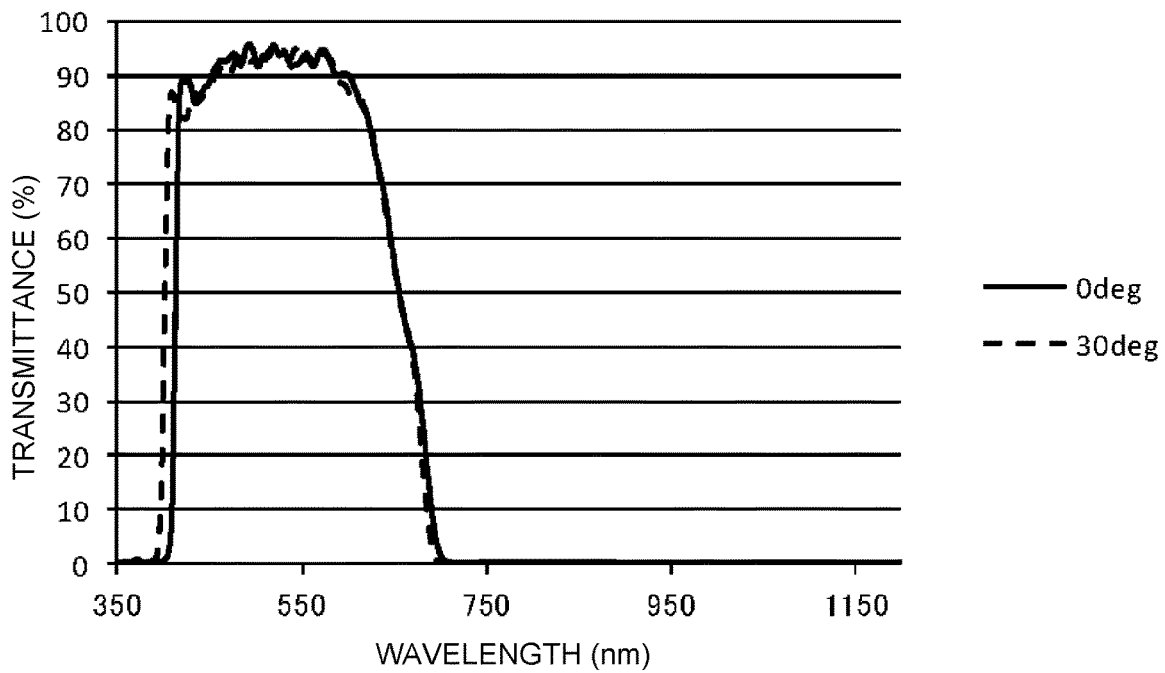
FIG. 4B is a view illustrating spectral transmittance curves of an optical filter obtained in an example.
Figure 4C:
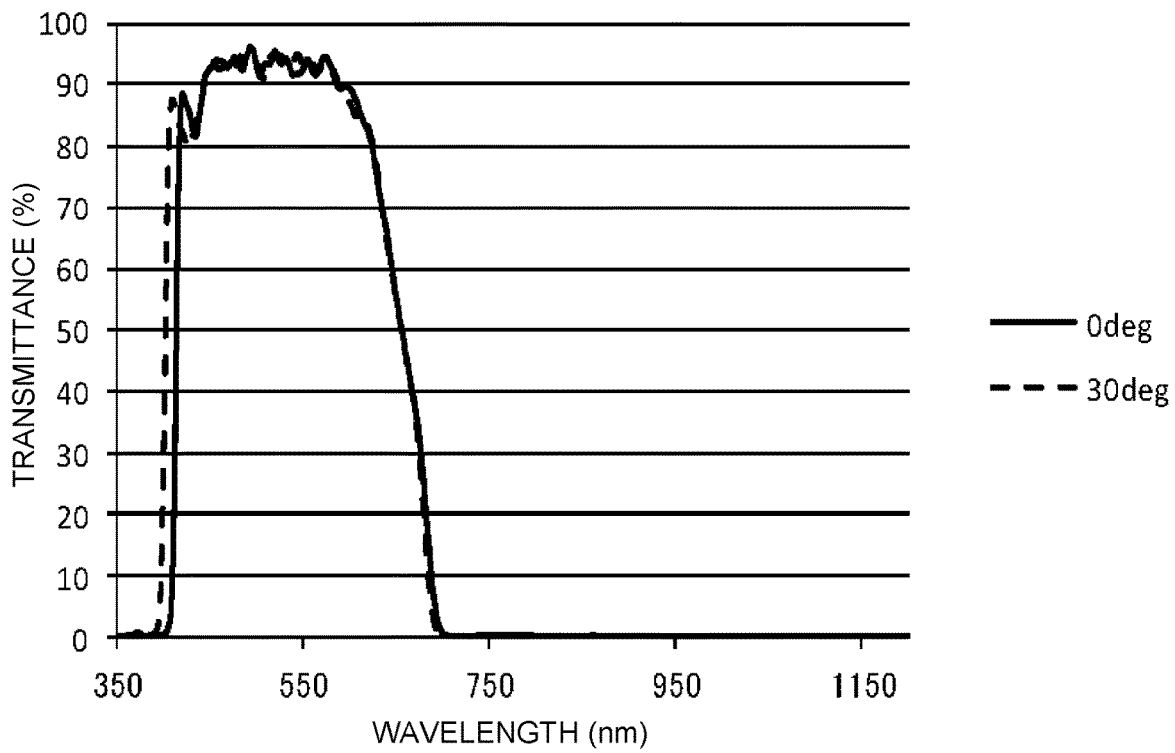
FIG. 4C is a view illustrating spectral transmittance curves of an optical filter obtained in an example.
Figure 4D:
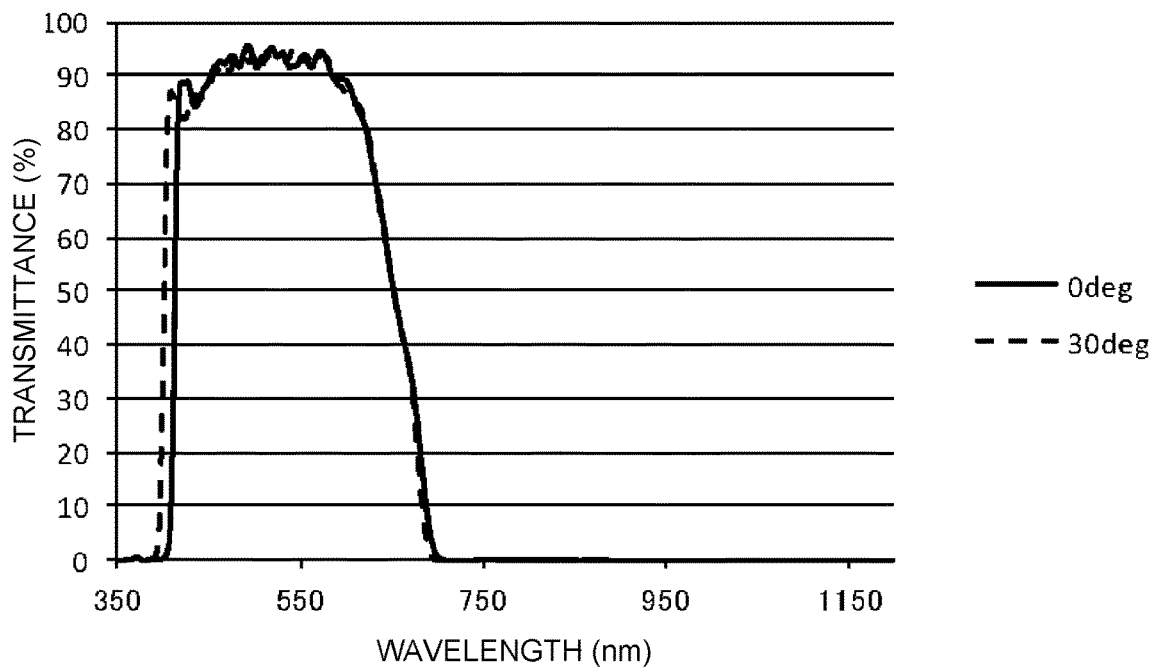
FIG. 4D is a view illustrating spectral transmittance curves of an optical filter obtained in an example.
Figure 4E:
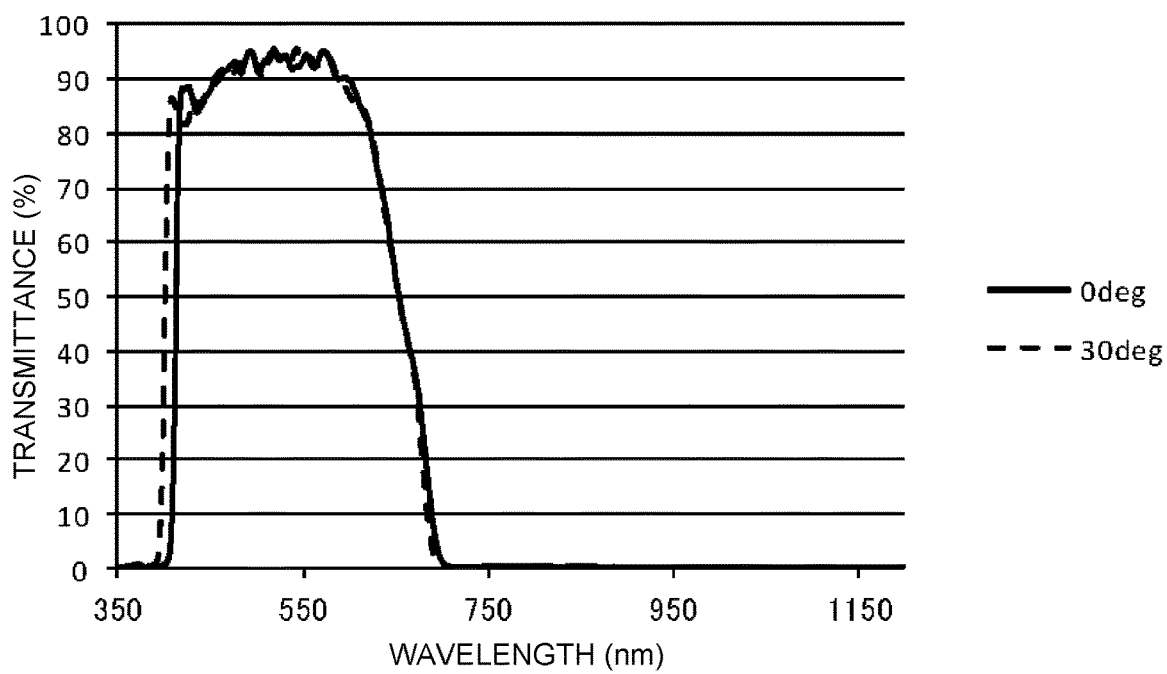
FIG. 4E is a view illustrating spectral transmittance curves of an optical filter obtained in an example.
Figure 4F:
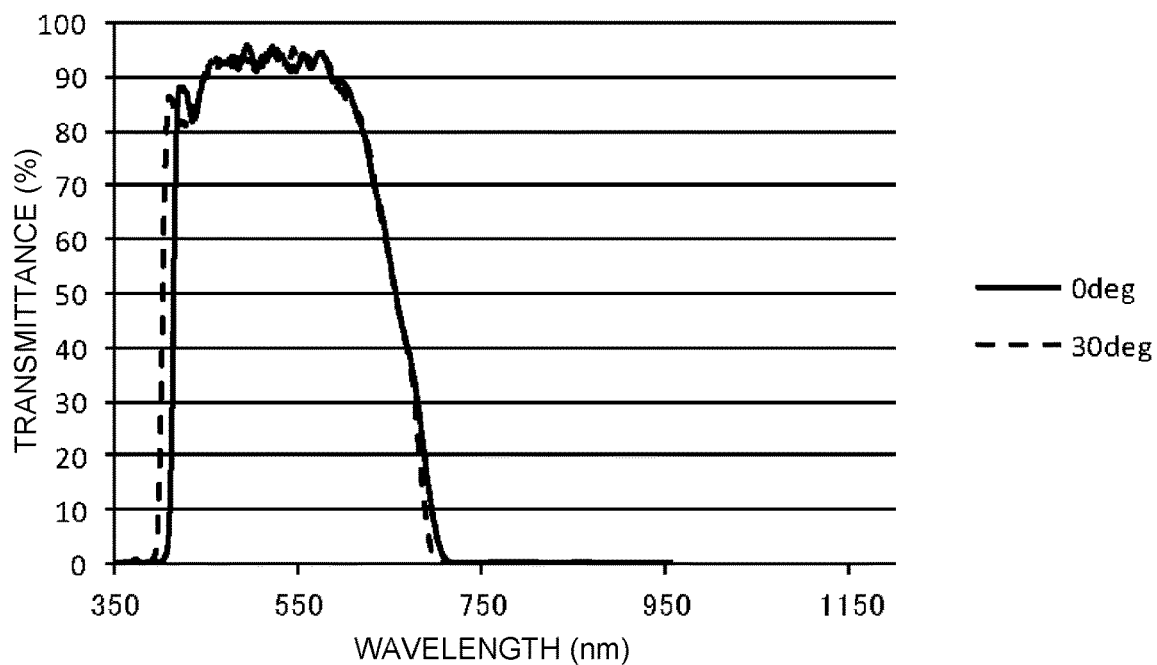
FIG. 4F is a view illustrating spectral transmittance curves of an optical filter obtained in an example.
Figure 4G:
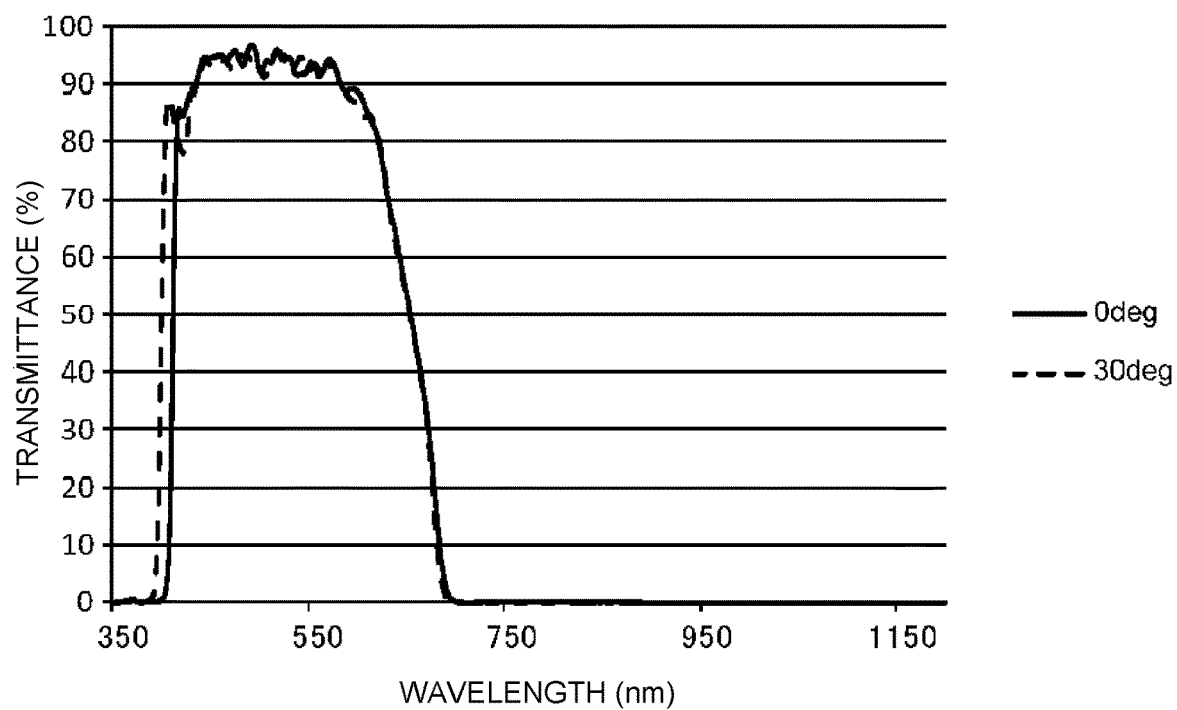
FIG. 4G is a view illustrating spectral transmittance curves of an optical filter obtained in an example.
Figure 4H:
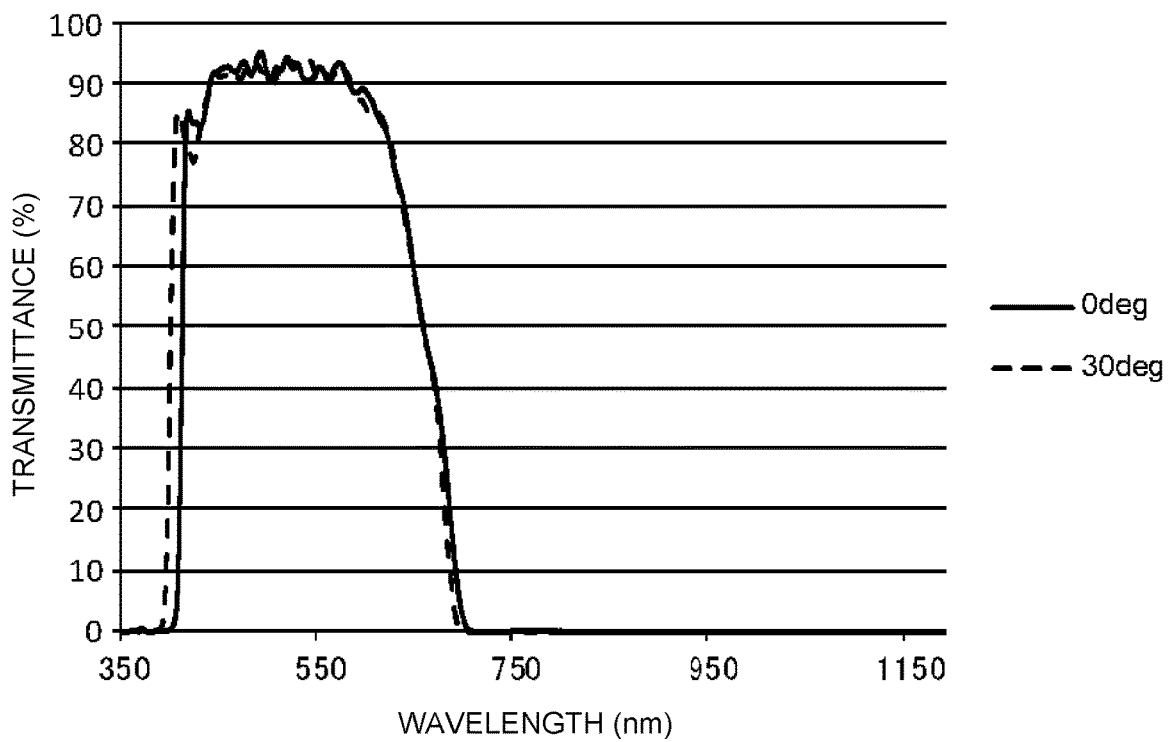
FIG. 4H is a view illustrating spectral transmittance curves of an optical filter obtained in an example.
Figure 4I:
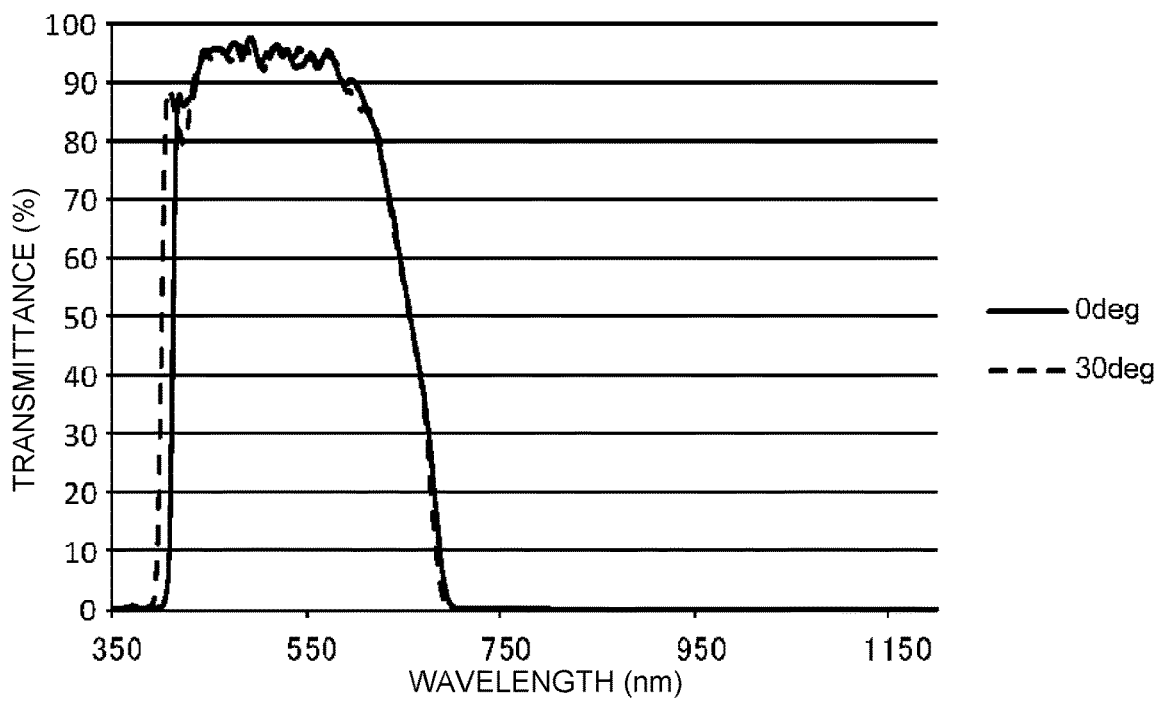
FIG. 4I is a view illustrating spectral transmittance curves of an optical filter obtained in an example.
Figure 4J:
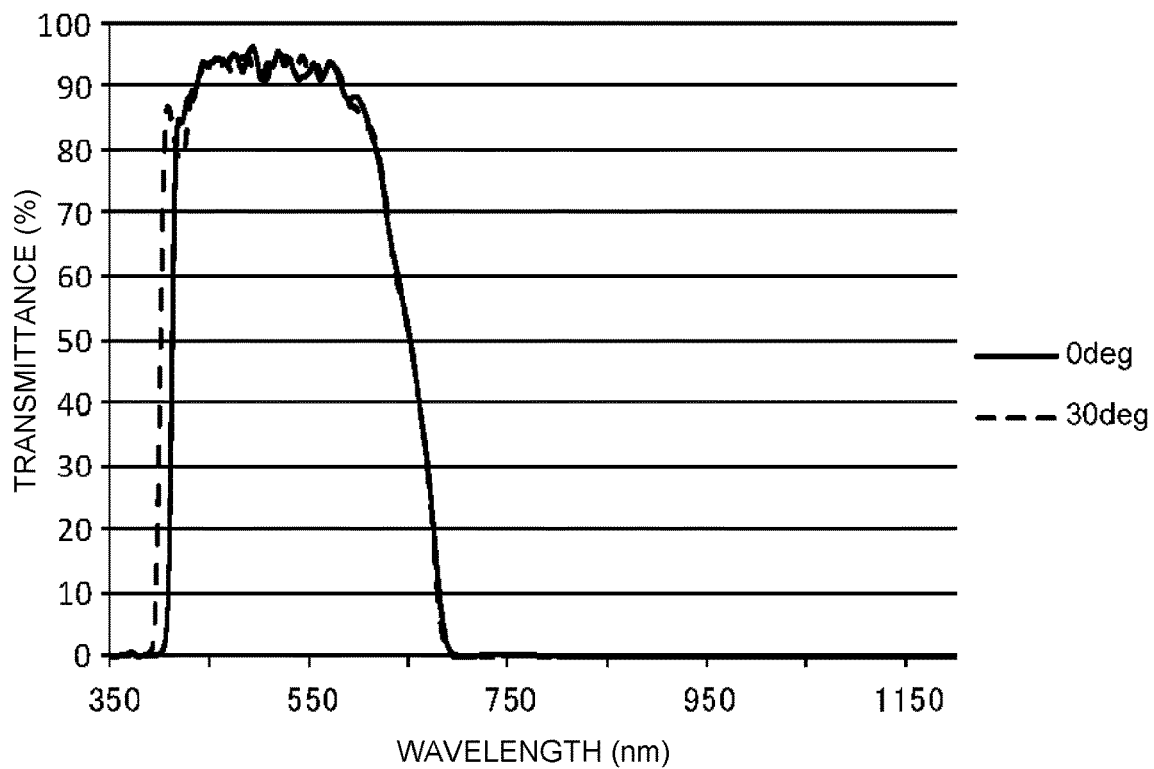
FIG. 4J is a view illustrating spectral transmittance curves of an optical filter obtained in an example.
Figure 4K:
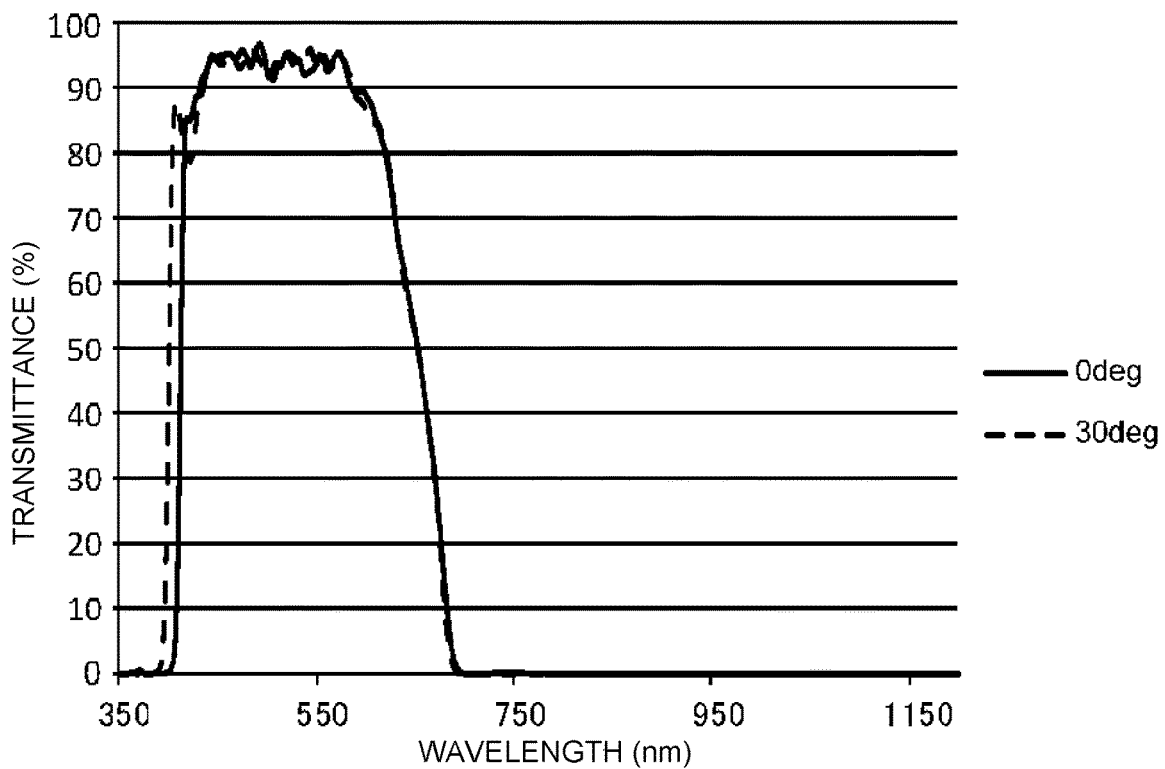
FIG. 4K is a view illustrating spectral transmittance curves of an optical filter obtained in an example.
Figure 4L:
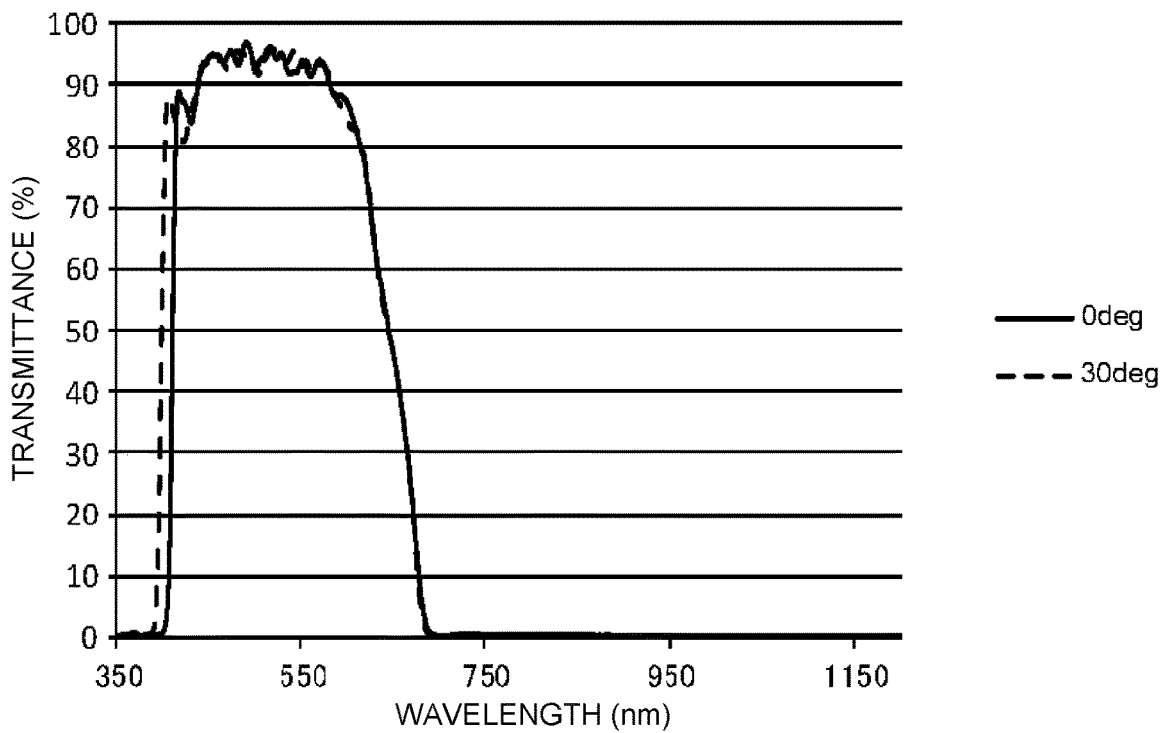
FIG. 4L is a view illustrating spectral transmittance curves of an optical filter obtained in an example.
Figure 4M:
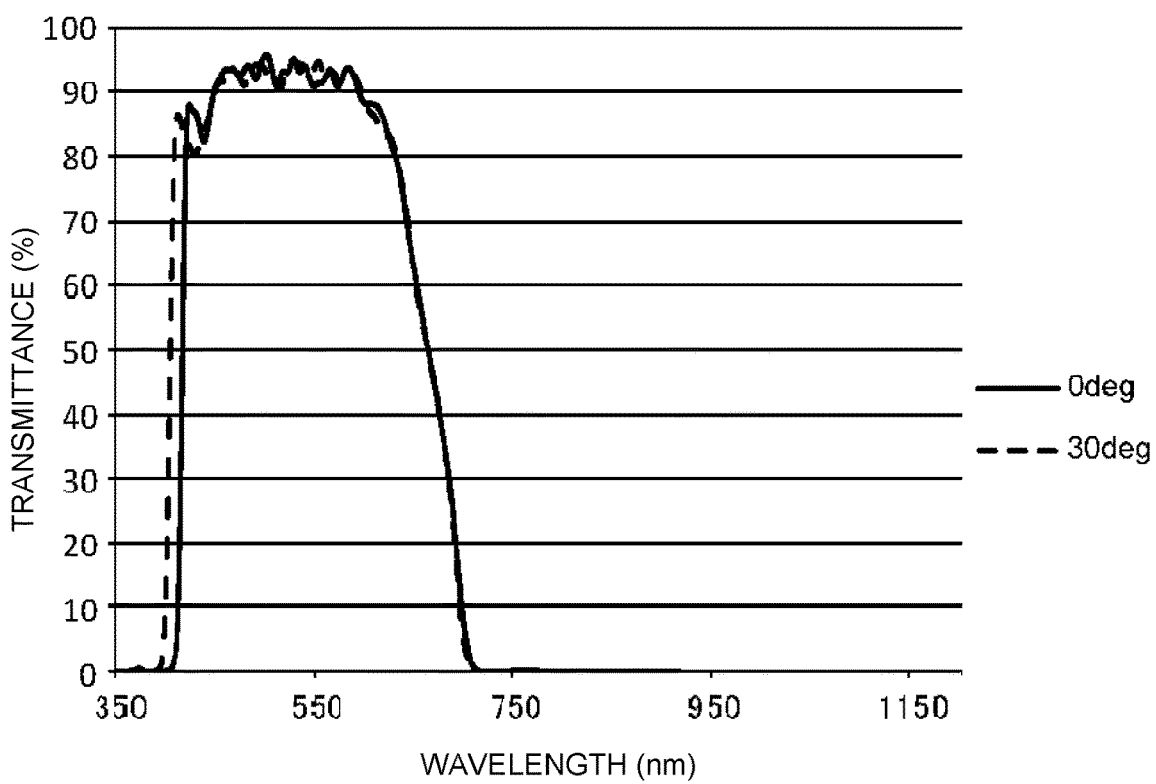
FIG. 4M is a view illustrating spectral transmittance curves of an optical filter obtained in an example.
Figure 4N:
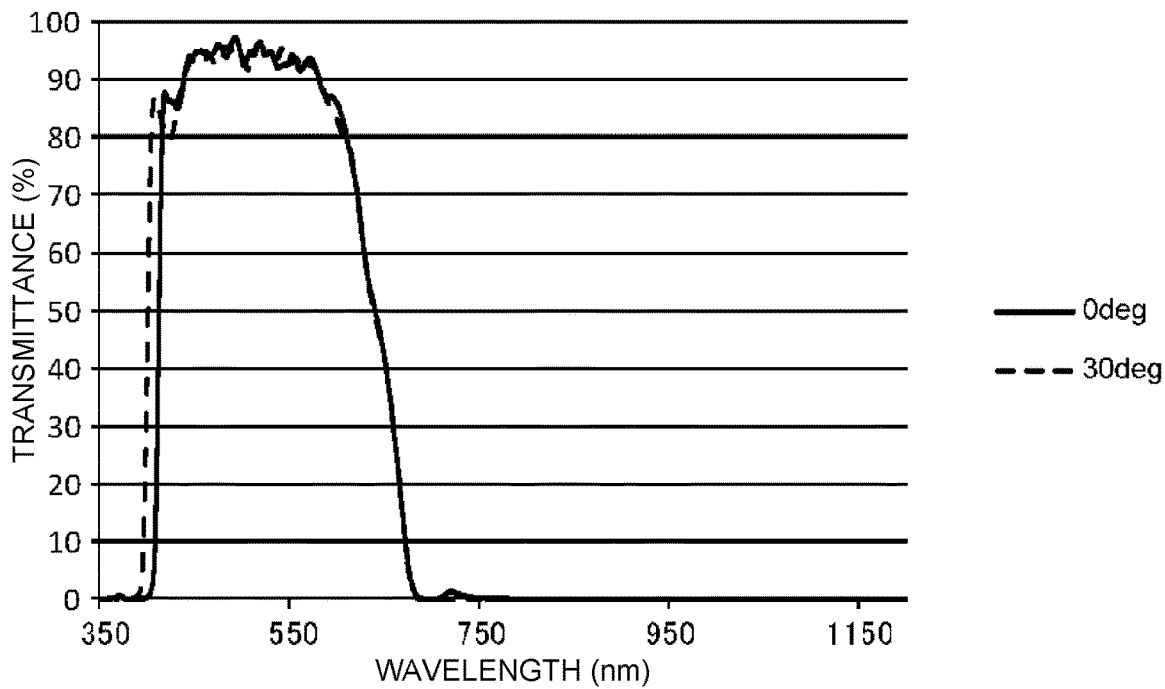
FIG. 4N is a view illustrating spectral transmittance curves of an optical filter obtained in an example.
Figure 4O:
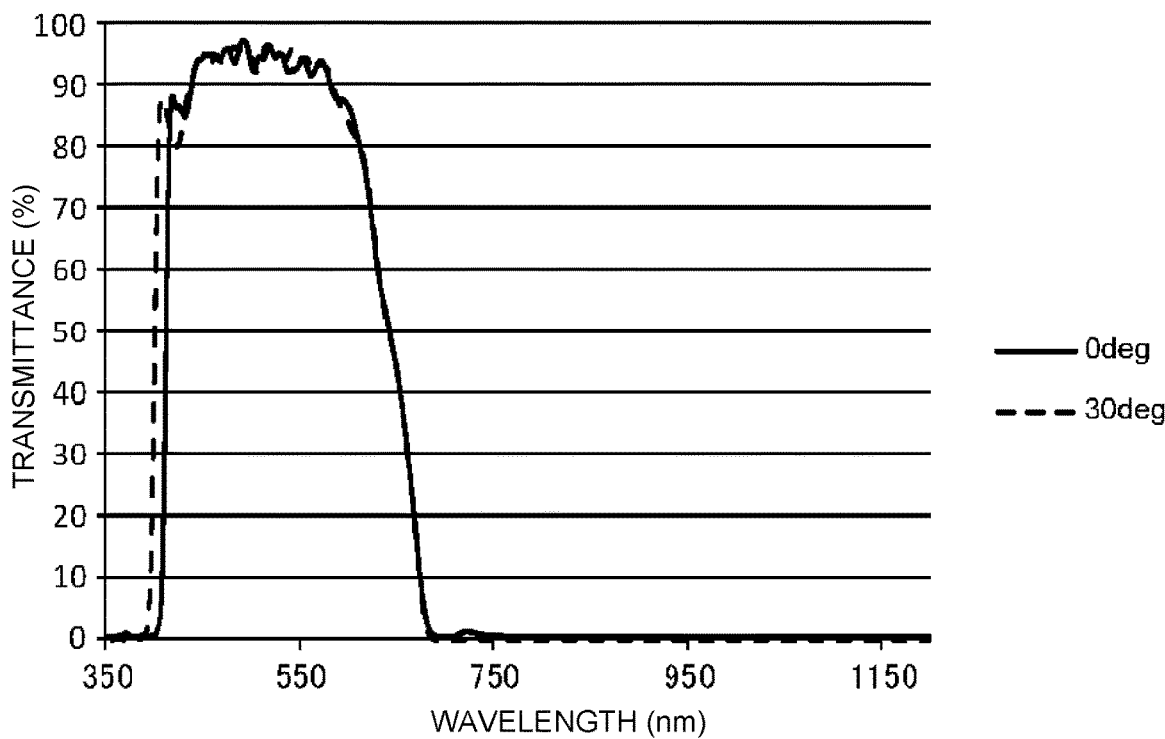
FIG. 4O is a view illustrating spectral transmittance curves of an optical filter obtained in an example.
Figure 4P:
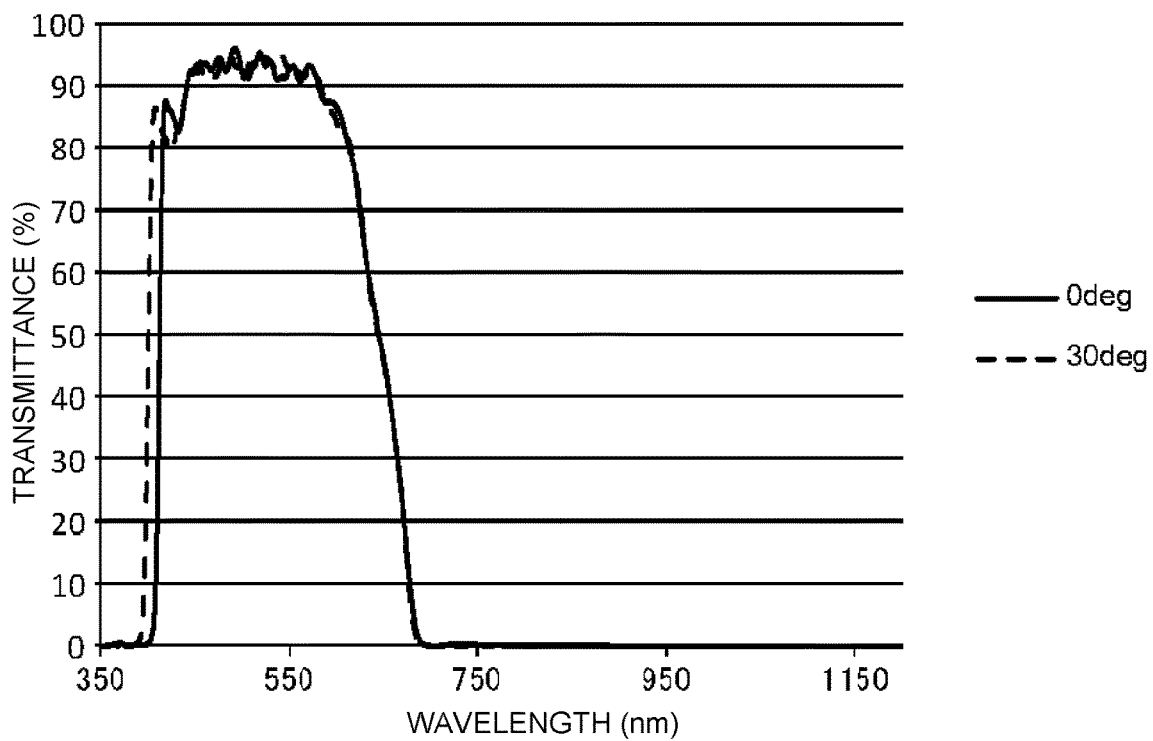
FIG. 4P is a view illustrating spectral transmittance curves of an optical filter obtained in an example.
Figure 4Q:
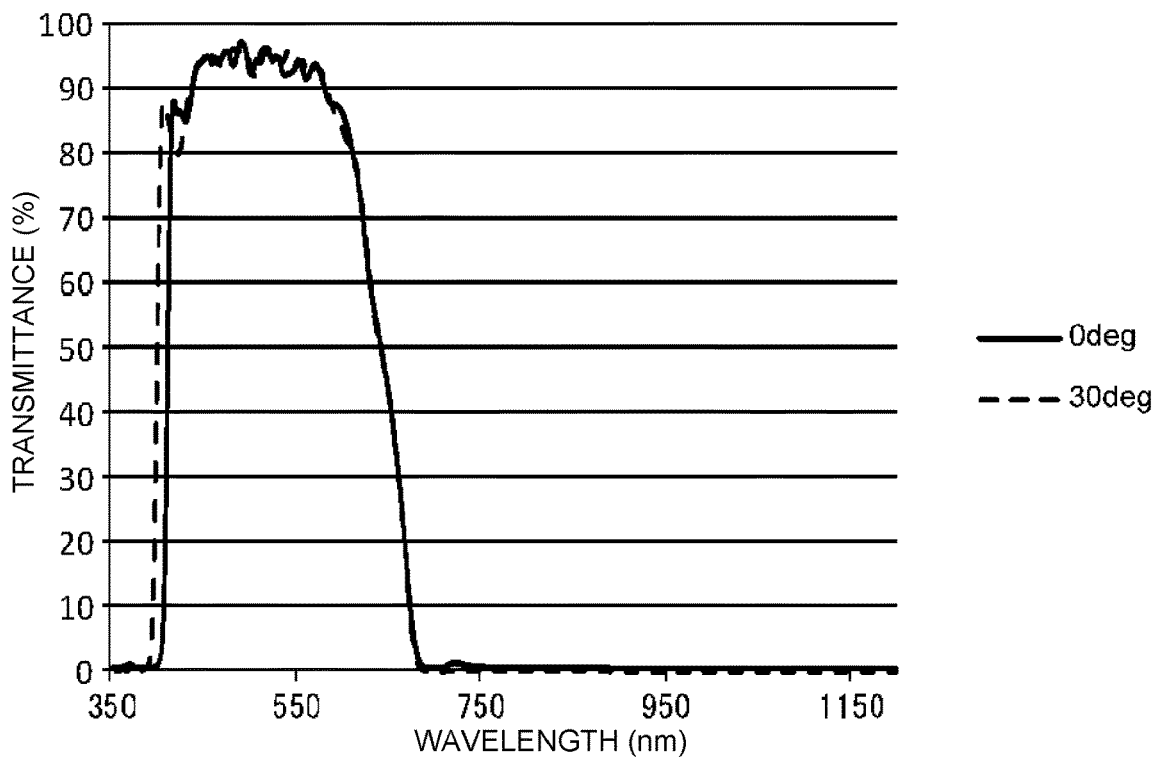
FIG. 4Q is a view illustrating spectral transmittance curves of an optical filter obtained in an example.
Figure 4R:
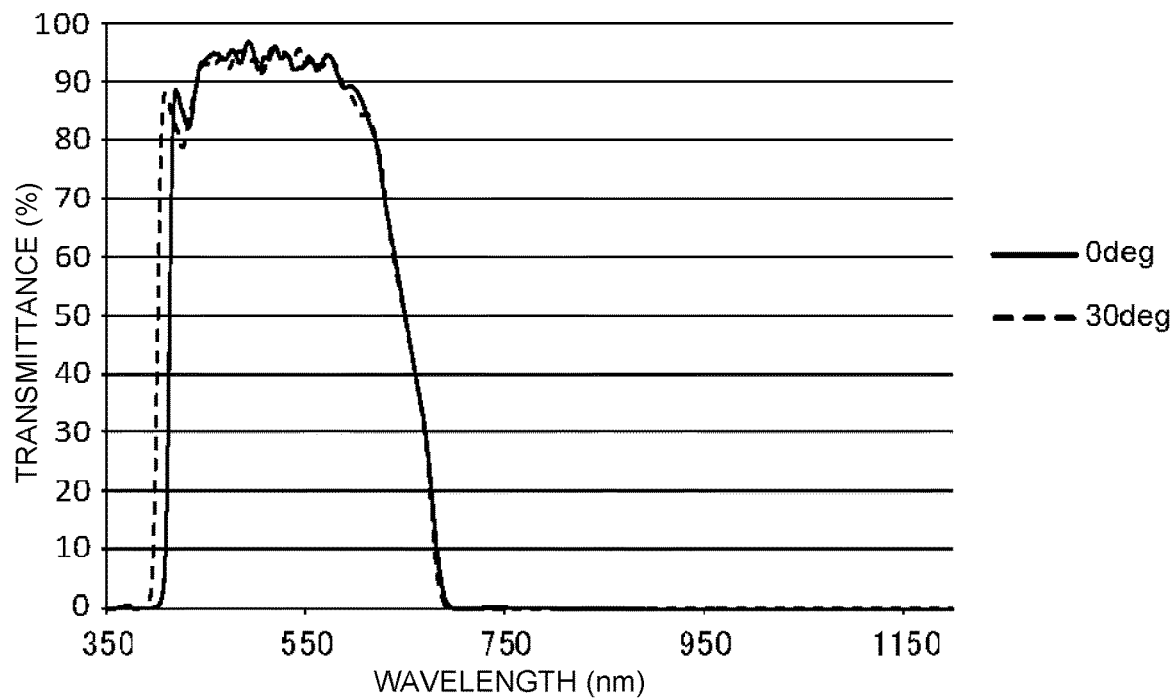
FIG. 4R is a view illustrating spectral transmittance curves of an optical filter obtained in an example.
Figure 4S:
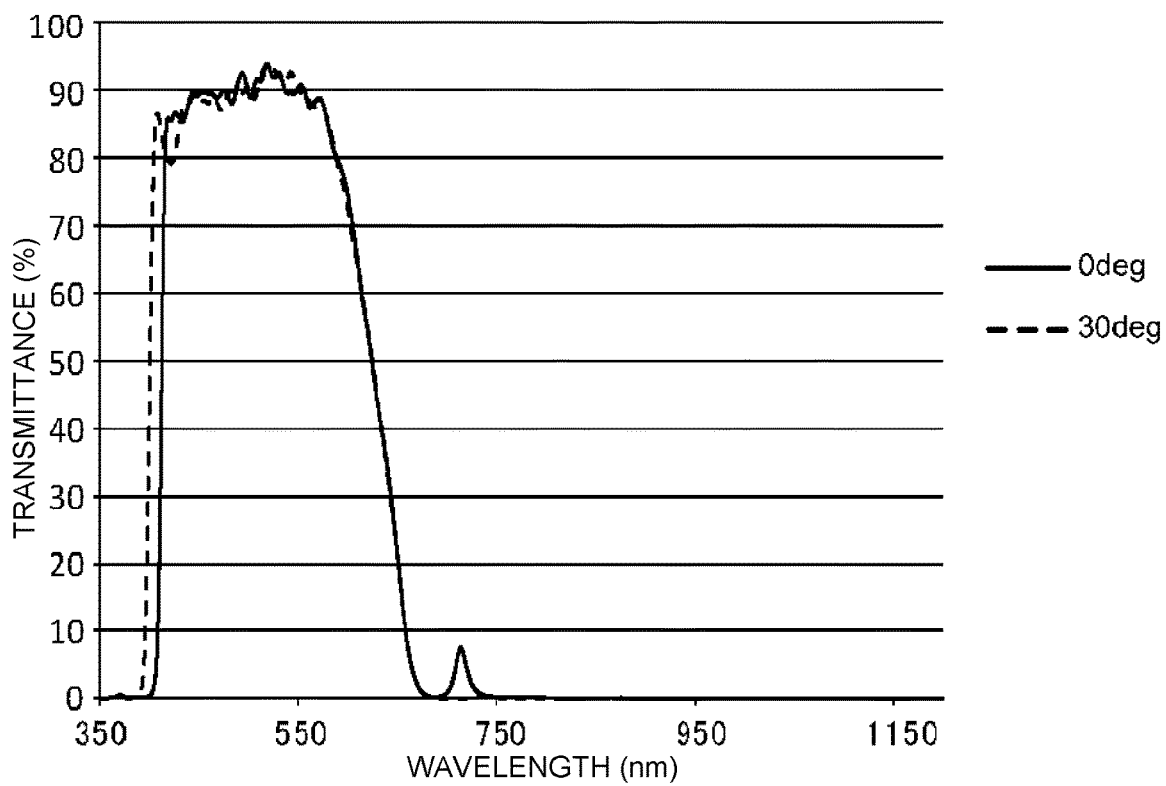
FIG. 4S is a view illustrating spectral transmittance curves of an optical filter obtained in an example.
Figure 4T:
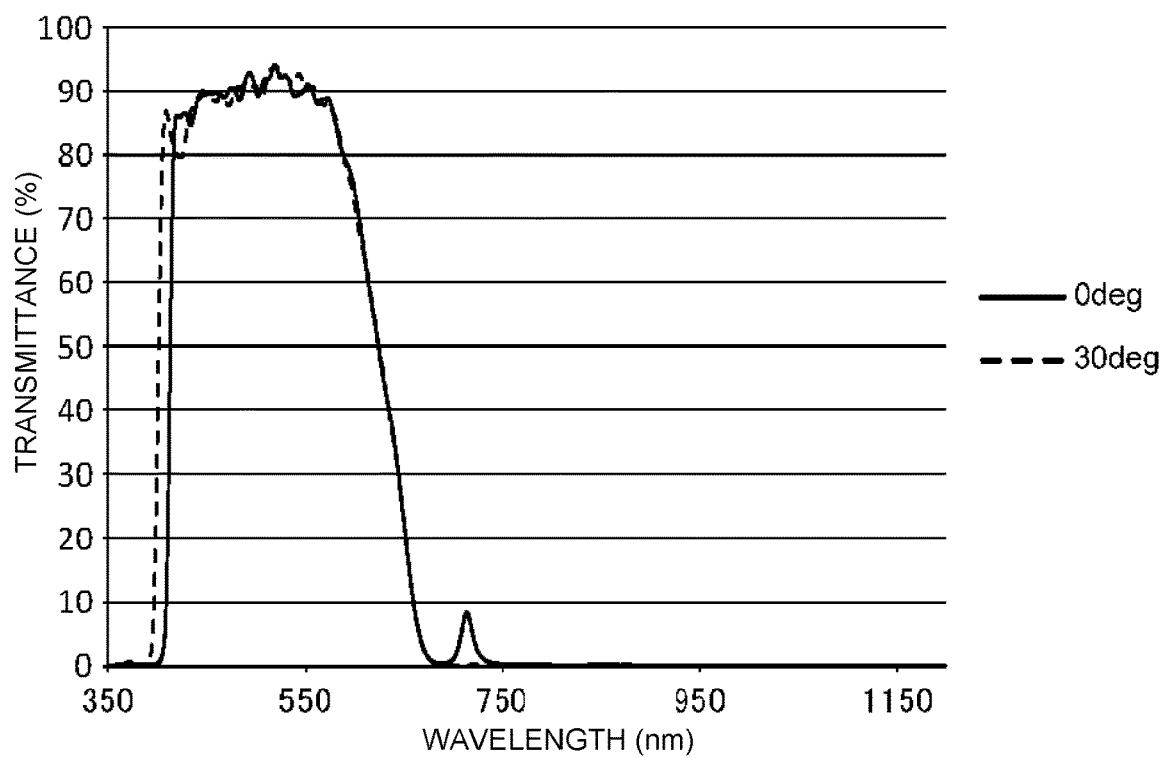
FIG. 4T is a view illustrating spectral transmittance curves of an optical filter obtained in an example.
Figure 4U:
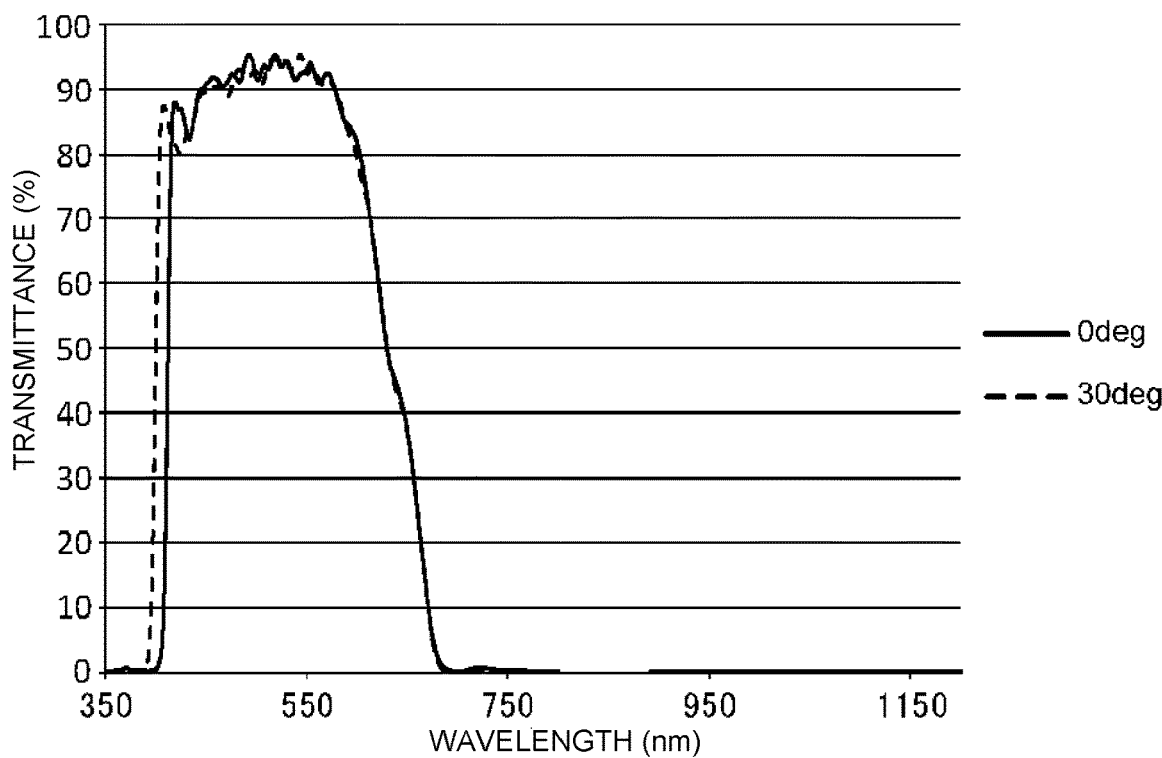
FIG. 4U is a view illustrating spectral transmittance curves of an optical filter obtained in an example.

Spectral transmittance curves (incident angles of 0° and 30°) were measured by using an ultraviolet-visible spectrophotometer (manufactured by Hitachi High Technologies Co., Ltd., U-4100 type) regarding the produced NIR filters (Example 1 to Example 22). The obtained spectral transmittance curves (incident angles of 0° and 300) are illustrated in FIG. 4A to FIG. 4U (respectively corresponding to Example 1 to Example 21).

Regarding each of the NIR filters of the respective examples, an average transmittance of light with a wavelength of 430 to 550 nm, a minimum transmittance of light with a wavelength of 430 to 550 nm, an average transmittance of light with a wavelength of 430 to 480 nm, an average transmittance of light with a wavelength of 350 to 395 nm, an average transmittance of light with a wavelength of 710 to 1100 nm, and an average shift amount of transmittance of light with a wavelength of 600 to 700 nm were calculated from measurement results. These results are listed in Table 4 and Table 5.

TABLE 4

| | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| Near-infrared-absorbing dye A | Type of dye | A1-1 | A1-2 | A1-3 | A1-4 | A1-5 | A1-7 | A1-8 | A1-9 | A1-10 | A1-11 | A1-12 |
| | Amount of dye * [part by mass] | | | | | | 10.9 | | | | | |
| Transparent resin | Type of resin | | | | | | Polyimide resin | | | | | |
| Absorption layer | Film thickness [μm] | | | | | | 1.0 | | | | | |
| Optical characteristics | Average transmittance [%](350-395 nm) | 0.18 | 0.18 | 0.18 | 0.18 | 0.17 | 0.18 | 0.17 | 0.17 | 0.18 | 0.17 | 0.17 |
| | Average transmittance [%](430-550 nm) | 91.7 | 91.9 | 92.4 | 91.8 | 91.4 | 91.7 | 93.6 | 91.5 | 94.2 | 92.9 | 93.8 |
| | Average transmittance [%](430-480 nm) | 90.0 | 90.0 | 91.1 | 89.9 | 89.1 | 90.0 | 93.5 | 90.6 | 93.9 | 92.7 | 93.9 |
| | Average transmittance [%](600-700 nm) | 51.0 | 54.0 | 51.7 | 51.4 | 52.4 | 52.3 | 50.3 | 55.4 | 52.8 | 46.9 | 48.1 |
| | Average transmittance [%](710-1100 nm) | 0.04 | 0.04 | 0.05 | 0.04 | 0.04 | 0.06 | 0.1 | 0.0 | 0.0 | 0.1 | 0.1 |
| | Minimum transmittance [%](430-550 nm) | 81.7 | 84.7 | 81.6 | 84.3 | 83.8 | 81.7 | 88.0 | 82.8 | 87.0 | 87.6 | 88.8 |
| | Average shift amount of transmittance [%/nm](600-700 nm) | 1.7 | 2.4 | 1.8 | 1.9 | 2.1 | 2.6 | 1.5 | 2.6 | 1.9 | 1.1 | 1.2 |

* Amount relative to 100 parts by mass of resin

TABLE 5

|  |  | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| Near-infrared-absorbing dye A | Type of dye | A1-13 | A1-14 | A1-15 | A1-16 | A1-17 | A1-18 | A1-19 | A4-1 | A4-2 | A4-3 | C-1 |
|  | Amount of dye * [part by mass] |  |  |  |  |  | 10.9 |  |  |  |  |  |
| Transparent resin | Type of resin | Polyimide resin | | | | | | | | | | |
| Absorption layer | Film thickness [μm] | | | | | | 1.0 | | | | | |
| Optical characteristics | Average transmittance [%](350-395 nm) | 0.18 | 0.18 | 0.18 | 0.18 | 0.18 | 0.18 | 0.18 | 0.16 | 0.18 | 0.18 | 0.17 |
|  | Average transmittance [%](430-550 nm) | 93.4 | 92.1 | 93.6 | 93.6 | 92.4 | 92.7 | 93.1 | 90.0 | 90.0 | 91.4 | 91.8 |
|  | Average transmittance [%](430-480 nm) | 92.5 | 90.8 | 92.7 | 92.8 | 91.3 | 91.6 | 92.0 | 88.7 | 88.7 | 89.2 | 88.7 |
|  | Average transmittance [%](600-700 nm) | 44.7 | 46.5 | 39.4 | 41.2 | 43.8 | 43.5 | 47.5 | 26.8 | 27.4 | 34.8 | 42.5 |
|  | Average transmittance [%](710-1100 nm) | 0.1 | 0.1 | 0.2 | 0.1 | 0.1 | 0.1 | 0.1 | 0.4 | 0.4 | 0.1 | 0.1 |
|  | Minimum transmittance [%](430-550 nm) | 83.9 | 82.3 | 84.9 | 84.8 | 82.7 | 83.1 | 82.2 | 85.3 | 84.5 | 82.2 | 80.1 |
|  | Average shift amount of transmittance [%/nm](600-700 nm) | 1.0 | 1.1 | 0.7 | 0.7 | 0.9 | 0.9 | 1.2 | 0.5 | 0.5 | 0.6 | 0.9 |

* Amount relative to 100 parts by mass of resin

As it can be seen from Table 4 and Table 5, all of the produced NIR filters of the examples (Example 1 to Example 21) satisfy the requirements (iii-1) to (iii-6), and in particular, have the optical filter characteristics having high transmittance of light with a wavelength of 430 to 550 nm. Note that the NIR filter of the comparative example (Example 22) satisfies the requirements (iii-1) to (iii-6), but all of the requirements (i-1) to (i-3) are not satisfied according to the measurement results of the dye in dichloromethane.

The near-infrared-absorbing dye according to the present disclosure has a good near-infrared blocking characteristic and excellent in transmittance of visible light, in particular, light with a wavelength of 430 to 550 nm, and thus it is useful for being applied to an optical filter and an imaging device where high precision color reproducibility is demanded.

What is claimed is:

1. A near-infrared-absorbing dye, having an absorption characteristic measured by dissolving the dye in dichloromethane satisfying requirements (i-1) to (i-3):
   (i-1) in an absorption spectrum at a wavelength of 400 to 800 nm, there is a maximum absorption wavelength $\lambda_{max}$ in a wavelength region of 670 nm or more;
   (i-2) the following relational expression is established between a maximum absorption constant $\varepsilon_A$ with respect to light with a wavelength of 430 to 550 urn and a maximum absorption constant $\varepsilon_{6B}$ with respect to light with a wavelength of 670 nm or more,
   $\varepsilon_B/\varepsilon_A \geq 65$; and
   (i-3) in a spectral transmittance curve, an average transmittance of light with a wavelength of 430 to 460 nm is 94.0% or more when a transmittance at the maximum absorption wavelength $\lambda_{max}$ is set to 1%.

2. The near-infrared-absorbing dye according to claim 1, wherein the absorption characteristic measured by dissolving the dye in dichloromethane satisfies a requirement (i-4):
   (i-4) in a spectral transmittance curve, when wavelengths with which transmittances become 80%, 10% on a shorter wavelength side than the maximum absorption wavelength $\lambda_{max}$ are respectively set to a wavelength $\lambda_{80}$ and a wavelength $\lambda_{10}$ when the transmittance at the maximum absorption wavelength $\lambda_{max}$ is set to 1%, a maximum value of a slope of the spectral transmittance curve between the wavelength $\lambda_{80}$ and the wavelength $\lambda_{10}$ is −0.5 [%/nm] or less.

3. The near-infrared-absorbing dye according to claim 1, wherein the absorption characteristic measured by dissolving the dye in dichloromethane satisfies a requirement (i-5):
   (i-5) in a spectral transmittance curve, a transmittance of light with a wavelength of 410 to 460 nm is 93.0% or more when the transmittance at the maximum absorption wavelength $\lambda_{max}$ is set to 1%.

4. The near-infrared-absorbing dye according to claim 1, wherein the absorption characteristic measured by dissolving the dye in dichloromethane satisfies a requirement (i-6):
   (i-6) in a spectral transmittance curve, a longest wavelength where a transmittance with respect to light with a wavelength of 460 nm or less becomes 97% is 457 nm or less when the transmittance at the maximum absorption wavelength $\lambda_{max}$ is set to 1%.

5. The near-infrared-absorbing dye according to claim 1, wherein the absorption characteristic measured by dissolving the dye in dichloromethane satisfies a requirement (i-7):
   (i-7) in a spectral transmittance curve, a difference between the wavelength $\lambda_{80}$ with which the transmittance becomes 80% on a shorter wavelength side than e maximum absorption wavelength $\lambda_{max}$ and the maximum absorption wavelength $\lambda_{max}$ is 78 nm or less when the transmittance at the maximum absorption wavelength $\lambda_{max}$ is set to 1%.

6. The near-infrared-absorbing dye according to claim 1, wherein in (i-3), the average transmittance of light with the wavelength of 430 to 460 nm is 95.0% or more.

7. The near-infrared-absorbing dye according to claim 1, which is formed of a squarylium-based compound and wherein the squarylium-based compound is a squarylium-based compound represented by Formula (AI):

[Chemical Formula 1]

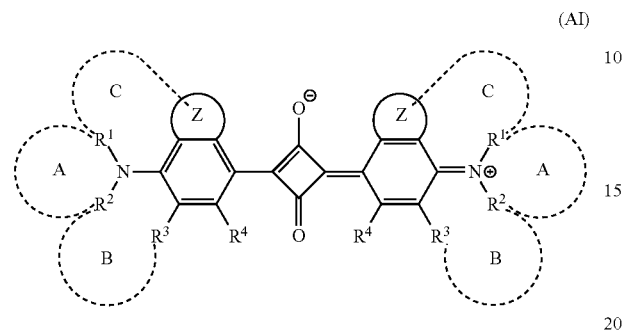

(AI)

in Formula (AI),
each of rings Z is independently a five-membered ring or a six-membered ring which may contain 0 to 3 pieces of heteroatoms in the ring and which may have a substituent,
$R^1$ and $R^2$, $R^2$ and $R^3$, and $R^1$ and a carbon atom or the heteroatom forming the ring Z may couple with each other and respectively form a hetero ring A; a hetero ring B, and a hetero ring C together with a nitrogen atom, when the hetero ring is not formed, $R^1$ and $R^2$ each independently represent a hydrogen atom, or a hydrocarbon group which may contain an unsaturated bond, a heteroatom, a saturated or unsaturated ring structure between carbon atoms and which may have a substituent, $R^3$ each independently represent an alkyl group or an alkoxy group which may contain a hydrogen atom, a halogen atom, a hydroxyl group, or a heteroatom between carbon atoms, and
$R^4$ each independently represent an alkyl group or an alkoxy group which may contain a hydrogen atom, a halogen atom, a hydroxyl group, or a heteroatom between carbon atoms.

8. The near-infrared-absorbing dye according to claim 7, wherein
the ring Z contains at least one nitrogen atom or sulfur atom as a heteroatom.

9. The near-infrared-absorbing dye according to claim 7, wherein
the ring Z is an aromatic hetero ring.

10. The near-infrared-absorbing dye according to claim 7, wherein
the rings Z each independently are a pyrrolidine ring, a piperidine ring, a piperazine ring, a pyrrole ring, a thiophene ring, an imidazole ring, a pyrazole ring; a thiazole ring; an isothiazole ring, an oxazole ring, an isoxazole ring, a pyridine ring, a pyrimidine ring, a pyridazine ring, a pyrazine ring, a triazine ring, or a triazole ring.

11. The near-infrared-absorbing dye according to claim 7, wherein
in Formula (AI), $R^1$ and $R^2$ each independently are a hydrogen atom, or a hydrocarbon group with a carbon number of 1 to 20 which may contain an unsaturated bond, a heteroatom, a saturated or unsaturated ring structure between carbon atoms, and which may have a substituent,
$R^3$ and $R^4$ each independently are an alkyl group or an alkoxy group with a carbon number of 1 to 20 which may contain a hydrogen atom, a halogen atom, or a heteroatom between carbon atoms.

12. The near-infrared-absorbing dye according to claim 7, wherein
in Formula (AI), $R^1$ and $R^2$ each independently are an alkyl group or an alkoxy group with a carbon number of 1 to 20 which may contain with a heteroatom between carbon atoms and which may have a substituent.

13. The near-infrared-absorbing dye according to claim 1, which is formed of a squarylium-based compound and, wherein the squarylium-based compound is a squarylium-based compound represented by Formula (AII):

[Chemical Formula 2]

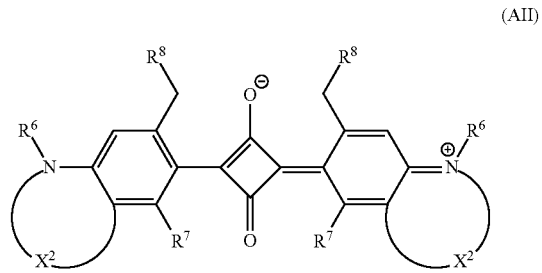

(AII)

in Formula (AII),
$R^6$ each independently represent a hydrogen atom, or a hydrocarbon group which may contain an unsaturated bond, a heteroatom, a saturated or unsaturated ring structure between carbon atoms and which may have a substituent,
$R^7$ each independently represent a hydrogen atom, a halogen atom, a hydroxyl group, or an alkyl group or an alkoxy group which may contain a heteroatom between carbon atoms,
$R^8$ each independently represent a halogen atom, a hydroxyl group, an alkoxy group with a carbon number of 1 to 12, an acyl group or an acyloxy group with a carbon number of 1 to 12, a perfluoroalkyl group with a carbon number of 1 to 12, or a —$SO_2R^9$ group (where $R^9$ represents an alkyl group with a carbon number of 1 to 12 which may have a substituent), and
$X^2$ each represent a bivalent hydrocarbon group which may contain an unsaturated bond, a heteroatom, a saturated or unsaturated ring structure between carbon atoms and which may have a substituent.

14. An optical filter, comprising:
an absorption layer which contains: the near-infrared-absorbing dye according to claim 1; and a resin.

15. The optical filter according to claim 14, wherein
an average transmittance of light with a wavelength of 430 to 550 nm is 90% or more, and a minimum transmittance of light with the wavelength of 430 to 550 nm is 75% or more in a spectral transmittance curve at an incident angle of 0°.

16. The optical filter according to claim 15, wherein
an average transmittance of light with a wavelength of 430 to 480 nm is 87% or more in a spectral transmittance curve at an incident angle of 0°.

17. The optical filter according to claim 16, wherein requirements (iii-3) to (iii-6) are satisfied:
- (iii-3) an average transmittance of light with a wavelength of 600 to 700 nm is 25% or more in a spectral transmittance curve at an incident angle of 0°;
- (iii-4) an average transmittance of light with a wavelength of 350 to 395 nm is 2% or less in a spectral transmittance curve at an incident angle of 0°;
- (iii-5) an average transmittance of light with a wavelength of 710 to 1100 nm is 2% or less in a spectral transmittance curve at an incident angle of 0°; and
- (iii-6) an average value of an absolute value of a difference between a transmittance of light with a wavelength of 600 to 700 nm in a spectral transmittance curve at an incident angle of 0° and a transmittance of light with the wavelength of 600 nm to 700 nm in a spectral transmittance curve at an incident angle of 30° is 7%/nm or less.

18. The optical filter according to claim 14, wherein the absorption layer is provided on a transparent substrate.

19. The optical filter according to claim 18, wherein the transparent substrate is a glass substrate.

20. The optical filter according to claim 19, wherein the transparent substrate is a near-infrared-absorbing glass substrate.

21. The optical filter according to claim 18, wherein the transparent substrate is formed of a resin.

22. The optical filter according to claim 14, wherein the absorption layer functions as a resin substrate.

23. An imaging device, comprising:
a solid-state image sensor;
an imaging lens; and
the optical filter according to claim 14.

24. A near-infrared-absorbing dye being formed of a squarylium-based compound represented by Formula (AI):

[Chemical Formula 3]

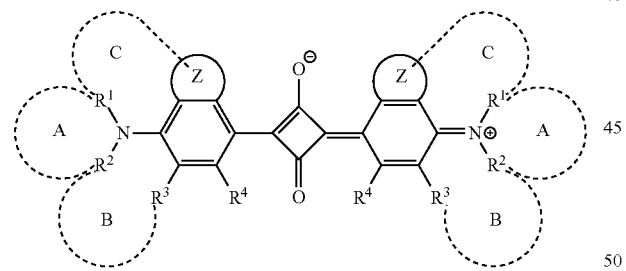

(AI)

in Formula (AI),
- each of rings Z is independently a five-membered ring or a six-membered ring which may contain 0 to 3 pieces of heteroatoms in the ring and which may have a substituent,
- $R^1$ and $R^2$, $R^2$ and $R^3$, and $R^1$ and a carbon atom or the heteroatom forming the ring Z may couple with each other and respectively form a hetero ring A, a hetero ring B, and a hetero ring C together with a nitrogen atom, and when the hetero ring is not formed, $R^1$ and $R^2$ each independently represent a hydrogen atom, or a hydrocarbon group which may contain an unsaturated bond, a heteroatom, a saturated or unsaturated ring structure between carbon atoms and which may have a substituent, $R^3$ each independently represent an alkyl group or an alkoxy group which may contain a hydrogen atom, a halogen atom, a hydroxyl group, or a heteroatom between carbon atoms, and
- $R^4$ each independently represent an alkyl group or an alkoxy group which may contain a hydrogen atom, a halogen atom, a hydroxyl group, or a heteroatom between carbon atoms.

25. The near-infrared-absorbing dye according to claim 24, wherein
the ring Z contains at least one nitrogen atom or sulfur atom as a heteroatom.

26. The ear-infrared-absorbing dye according to claim 24, wherein
the ring Z is an aromatic hetero ring.

27. The near-infrared-absorbing dye according to claim 24, wherein
the rings Z each independently are a pyrrolidine ring, a piperidine ring, a piperazine ring, a pyrrole ring, a thiophene ring, an imidazole ring, a pyrazole ring, a thiazole ring, an isothiazole ring, an oxazole ring, an isoxazole ring, a pyridine ring, a pyrimidine ring, a pyridazine ring, a pyrazine ring, a triazine ring, or a triazole ring.

28. A near-infrared-absorbing dye being formed of a squarylium-based compound represented by Formula (AII):

[Chemical Formula 4]

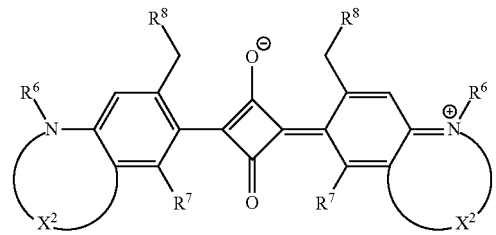

(AII)

in Formula (AII),
- $R^6$ each independently represent a hydrogen atom, or a hydrocarbon group which may contain an unsaturated bond, a heteroatom, a saturated or unsaturated ring structure between carbon atoms and which may have a substituent,
- $R^7$ each independently represent a hydrogen atom, a halogen atom, a hydroxyl group, or an alkyl group or an alkoxy group which may contain a heteroatom between carbon atoms,
- $R^8$ each independently represent a halogen atom, a hydroxyl group, an alkoxy group with a carbon number of 1 to 12, an acyl group or an acyloxy group with a carbon number of 1 to 12, a perfluoroalkyl group with a carbon number of 1 to 12, or a —$SO_2R^9$ group (where $R^9$ represents an alkyl group with a carbon number of 1 to 12 which may have a substituent), and
- $X^2$ each represent a bivalent hydrocarbon group which may contain an unsaturated bond, a heteroatom, a saturated or unsaturated ring structure between carbon atoms and which may have a substituent.

* * * * *